(12) United States Patent
Courtney, Jr. et al.

(10) Patent No.: US 12,137,953 B2
(45) Date of Patent: Nov. 12, 2024

(54) HUMERAL FIXATION PLATES

(71) Applicant: HOWMEDICA OSTEONICS CORP., Mahwah, NJ (US)

(72) Inventors: Robert Courtney, Jr., Pierceton, IN (US); William Matthew Kuester, Chaska, MN (US); Robert Benjamin Rice, Bloomington, MN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 0 days.

(21) Appl. No.: 17/869,011

(22) Filed: Jul. 20, 2022

(65) Prior Publication Data
US 2022/0354550 A1 Nov. 10, 2022

Related U.S. Application Data

(63) Continuation of application No. 16/649,956, filed as application No. PCT/US2018/055290 on Oct. 10, 2018, now Pat. No. 11,426,220.

(51) Int. Cl.
| A61B 17/80 | (2006.01) |
| A61B 17/17 | (2006.01) |
| A61B 17/84 | (2006.01) |

(52) U.S. Cl.
CPC ........ *A61B 17/808* (2013.01); *A61B 17/8057* (2013.01); *A61B 17/8061* (2013.01);
(Continued)

(58) Field of Classification Search
CPC .............. A61B 17/808; A61B 17/8061; A61B 17/1728; A61B 17/1739; A61B 17/1746;
(Continued)

(56) References Cited

U.S. PATENT DOCUMENTS

| 2,500,370 A | 3/1950 | McKibbin |
| 2,682,265 A | 6/1954 | Collison |
(Continued)

FOREIGN PATENT DOCUMENTS

| DE | 7115713 | 6/1975 |
| DE | 8533134.1 | 11/1985 |
(Continued)

OTHER PUBLICATIONS

"ACE Symmetry Titanium Upper Extremity Plates: Curves in All the Right Places", Ace Medical Company, 1996, in 5 pages.
(Continued)

*Primary Examiner* — Marcela I. Shirsat
(74) *Attorney, Agent, or Firm* — DUANE MORRIS LLP

(57) ABSTRACT

Provided is a slot anchor guide that includes a medial portion and a lateral portion, the medial portion includes a medial projection configured to span a slot of a fixation plate, where the slot anchor guide is configured to guide an anchor through a predetermined position of a slot of the fixation plate and to mate with the fixation plate to allow a surgeon to place the fixation plate on a bone face by manipulating the lateral portion. Also provided is a tuberosity fracture plate that includes a tuberosity end having a first portion configured to overlay a first tuberosity and a second portion opposite the first portion, a distal portion coupled with and extending away from the tuberosity portion.

9 Claims, 29 Drawing Sheets

(52) U.S. Cl.
CPC ........ *A61B 17/848* (2013.01); *A61B 17/1728* (2013.01); *A61B 17/1739* (2013.01); *A61B 17/1746* (2013.01); *A61B 17/1753* (2013.01); *A61B 17/1778* (2016.11); *Y10T 408/567* (2015.01); *Y10T 408/568* (2015.01)

(58) Field of Classification Search
CPC .............. A61B 17/175; A61B 17/1753; A61B 17/1778; Y10T 408/567; Y10T 408/568
USPC ............................................ 606/291, 96, 98
See application file for complete search history.

(56) References Cited

U.S. PATENT DOCUMENTS

| | | |
|---|---|---|
| 3,334,624 A | 8/1967 | Schneider et al. |
| 3,433,220 A | 3/1969 | Zickel |
| 3,709,218 A | 1/1973 | Halloran |
| 3,781,917 A | 1/1974 | Mathys |
| 3,842,825 A | 10/1974 | Wagner |
| 3,939,498 A | 2/1976 | Lee et al. |
| 3,973,278 A | 8/1976 | Shersher |
| 3,977,398 A | 8/1976 | Burstein |
| 4,011,863 A | 3/1977 | Zickel |
| 4,055,172 A | 10/1977 | Ender et al. |
| 4,091,806 A | 5/1978 | Aginsky |
| 4,101,985 A | 7/1978 | Baumann et al. |
| 4,103,683 A | 8/1978 | Neufeld |
| 4,135,507 A | 1/1979 | Harris |
| 4,169,470 A | 10/1979 | Ender et al. |
| 4,227,518 A | 10/1980 | Aginsky |
| 4,237,875 A | 12/1980 | Termanini |
| 4,274,754 A | 6/1981 | Cohen |
| 4,338,926 A | 7/1982 | Kummer et al. |
| 4,393,868 A | 7/1983 | Teague |
| 4,423,721 A | 1/1984 | Otte et al. |
| 4,446,857 A | 5/1984 | Otte et al. |
| 4,453,539 A | 6/1984 | Raftopoulos et al. |
| 4,467,793 A | 8/1984 | Ender et al. |
| 4,473,069 A | 9/1984 | Kolmert |
| 4,475,545 A | 10/1984 | Ender |
| 4,483,335 A | 11/1984 | Tornier |
| 4,493,317 A | 1/1985 | Klaue |
| 4,513,744 A | 4/1985 | Klaue |
| 4,522,202 A | 6/1985 | Otte et al. |
| 4,541,424 A | 9/1985 | Grosse et al. |
| 4,590,930 A | 5/1986 | Kurth et al. |
| 4,622,959 A | 11/1986 | Marcus et al. |
| 4,630,601 A | 12/1986 | Harder et al. |
| 4,667,663 A | 5/1987 | Miyata |
| 4,697,585 A | 10/1987 | Williams |
| 4,705,027 A | 11/1987 | Klaue |
| 4,712,541 A | 12/1987 | Harder et al. |
| 4,733,654 A | 3/1988 | Marino |
| 4,775,381 A | 10/1988 | Tari et al. |
| 4,781,181 A | 11/1988 | Tanguy |
| 4,794,919 A | 1/1989 | Nilsson |
| 4,805,607 A | 2/1989 | Engelhardt et al. |
| 4,846,162 A | 7/1989 | Moehring |
| 4,854,312 A | 8/1989 | Raftopoulos et al. |
| 4,858,602 A | 8/1989 | Seidel et al. |
| 4,875,474 A | 10/1989 | Border |
| 4,875,475 A | 10/1989 | Comte et al. |
| 4,877,019 A | 10/1989 | Vives |
| 4,911,153 A | 3/1990 | Boder |
| 4,943,291 A | 7/1990 | Tanguy |
| 4,944,764 A | 7/1990 | Stossel |
| 4,946,459 A | 8/1990 | Bradshaw et al. |
| 4,955,886 A | 9/1990 | Pawluk |
| 4,976,258 A | 12/1990 | Richter et al. |
| 4,976,714 A | 12/1990 | Aghion |
| 4,988,350 A | 1/1991 | Herzberg |
| 5,013,314 A | 5/1991 | Firica et al. |
| 5,035,697 A | 7/1991 | Frigg |
| 5,041,115 A | 8/1991 | Frigg et al. |
| 5,057,103 A | 10/1991 | Davis |
| 5,057,110 A | 10/1991 | Kranz et al. |
| 5,066,296 A | 11/1991 | Chapman et al. |
| 5,084,053 A | 1/1992 | Ender |
| 5,100,404 A | 3/1992 | Hayes |
| 5,122,146 A | 6/1992 | Chapman et al. |
| 5,135,527 A | 8/1992 | Ender |
| 5,167,666 A | 12/1992 | Mattheck et al. |
| 5,190,543 A | 3/1993 | Schlapfer |
| 5,197,966 A | 3/1993 | Sommerkamp |
| 5,201,735 A | 4/1993 | Chapman et al. |
| 5,211,645 A | 5/1993 | Baumgart et al. |
| 5,239,569 A | 8/1993 | Saleh et al. |
| 5,248,313 A | 9/1993 | Greene et al. |
| 5,263,955 A | 11/1993 | Baumgart et al. |
| 5,268,000 A | 12/1993 | Ottieri et al. |
| 5,281,224 A | 1/1994 | Faccioli et al. |
| 5,295,991 A | 3/1994 | Frigg |
| 5,334,192 A | 8/1994 | Behrens |
| 5,352,228 A | 10/1994 | Kummer et al. |
| 5,356,410 A | 10/1994 | Pennig |
| 5,397,328 A | 3/1995 | Behrens et al. |
| 5,403,321 A | 4/1995 | DiMarco |
| 5,411,503 A | 5/1995 | Hollstien et al. |
| 5,415,660 A | 5/1995 | Campbell et al. |
| 5,429,638 A | 7/1995 | Muschler et al. |
| 5,433,718 A | 7/1995 | Brinker |
| 5,441,500 A | 8/1995 | Seidel et al. |
| 5,443,466 A | 8/1995 | Shah |
| 5,458,654 A | 10/1995 | Tepic |
| 5,472,444 A | 12/1995 | Huebner et al. |
| 5,484,438 A | 1/1996 | Pennig |
| 5,499,986 A | 3/1996 | DiMarco |
| 5,536,269 A | 7/1996 | Spievack |
| 5,549,610 A | 8/1996 | Russell et al. |
| 5,569,262 A | 10/1996 | Carney |
| 5,573,536 A | 11/1996 | Grosse et al. |
| 5,578,035 A | 11/1996 | Lin |
| 5,586,985 A | 12/1996 | Putnam et al. |
| 5,618,286 A | 4/1997 | Brinker |
| 5,620,445 A | 4/1997 | Brosnahan et al. |
| 5,620,449 A | 4/1997 | Faccioli et al. |
| 5,626,579 A | 5/1997 | Muschler et al. |
| 5,643,258 A | 7/1997 | Robioneck et al. |
| 5,645,545 A | 7/1997 | Bryant |
| 5,653,709 A | 8/1997 | Frigg |
| 5,658,283 A | 8/1997 | Huebner |
| 5,658,287 A | 8/1997 | Hofmann et al. |
| 5,665,086 A | 9/1997 | Itoman et al. |
| 5,681,318 A | 10/1997 | Pennig et al. |
| 5,690,634 A | 11/1997 | Muller et al. |
| 5,697,930 A | 12/1997 | Itoman et al. |
| 5,697,934 A | 12/1997 | Huebner |
| 5,713,902 A | 2/1998 | Friedl |
| 5,718,704 A | 2/1998 | Medoff |
| 5,766,174 A | 6/1998 | Perry |
| 5,766,179 A | 6/1998 | Faccioli et al. |
| 5,766,180 A | 6/1998 | Winquist |
| 5,776,194 A | 7/1998 | Mikol et al. |
| 5,779,705 A | 7/1998 | Matthews |
| 5,853,413 A | 12/1998 | Carter et al. |
| 5,928,235 A | 7/1999 | Friedl |
| 5,941,878 A | 8/1999 | Medoff |
| 5,951,557 A | 9/1999 | Luter |
| 5,954,722 A | 9/1999 | Bono |
| 5,961,553 A | 10/1999 | Coty et al. |
| 5,968,047 A | 10/1999 | Reed |
| 5,976,134 A | 11/1999 | Huebner |
| 5,997,490 A | 12/1999 | McLeod et al. |
| 6,010,505 A | 1/2000 | Asche et al. |
| 6,010,506 A | 1/2000 | Gosney et al. |
| 6,019,761 A | 2/2000 | Gustilo |
| 6,022,349 A | 2/2000 | McLeod et al. |
| 6,027,506 A | 2/2000 | Faccioli et al. |
| 6,033,407 A | 3/2000 | Behrens |
| 6,039,739 A | 3/2000 | Simon |
| 6,056,755 A | 5/2000 | Horas et al. |
| 6,074,392 A | 6/2000 | Durham |
| 6,077,264 A | 6/2000 | Chemello |

(56) References Cited

U.S. PATENT DOCUMENTS

| | | |
|---|---|---|
| 6,080,159 A | 6/2000 | Vichard |
| 6,093,192 A | 7/2000 | Abel |
| 6,096,040 A | 8/2000 | Esser |
| 6,120,504 A | 9/2000 | Brumback et al. |
| 6,123,708 A | 9/2000 | Kilpela et al. |
| 6,123,709 A | 9/2000 | Jones |
| 6,126,661 A | 10/2000 | Faccioli et al. |
| 6,146,384 A | 11/2000 | Lee et al. |
| 6,168,628 B1 | 1/2001 | Huebner |
| 6,200,321 B1 | 3/2001 | Orbay et al. |
| 6,206,880 B1 | 3/2001 | Karladani |
| 6,221,073 B1 | 4/2001 | Weiss et al. |
| 6,221,074 B1 | 4/2001 | Cole et al. |
| D443,060 S | 5/2001 | Benirschke et al. |
| 6,224,601 B1 | 5/2001 | Friedl |
| 6,228,086 B1 | 5/2001 | Wahl et al. |
| 6,231,576 B1 | 5/2001 | Frigg et al. |
| 6,245,075 B1 | 6/2001 | Betz et al. |
| 6,248,109 B1 | 6/2001 | Stoffella |
| 6,261,289 B1 | 7/2001 | Levy |
| 6,270,499 B1 | 8/2001 | Leu et al. |
| 6,273,892 B1 | 8/2001 | Orbay et al. |
| 6,283,969 B1 | 9/2001 | Grusin et al. |
| 6,296,645 B1 | 10/2001 | Hover et al. |
| 6,319,253 B1 | 11/2001 | Ackeret et al. |
| 6,355,069 B1 | 3/2002 | DeCarlo, Jr. et al. |
| 6,358,250 B1 | 3/2002 | Orbay |
| 6,364,882 B1 | 4/2002 | Orbay |
| 6,379,359 B1 | 4/2002 | Dahners |
| 6,379,360 B1 | 4/2002 | Ackeret et al. |
| 6,383,185 B1 | 5/2002 | Baumgart |
| 6,387,098 B1 | 5/2002 | Cole et al. |
| 6,395,033 B1 | 5/2002 | Pepper |
| 6,402,753 B1 | 6/2002 | Cole et al. |
| 6,409,768 B1 | 6/2002 | Tepic et al. |
| 6,416,516 B1 | 7/2002 | Stauch et al. |
| 6,423,066 B1 | 7/2002 | Harder et al. |
| 6,440,135 B2 | 8/2002 | Orbay et al. |
| 6,443,954 B1 | 9/2002 | Bramlet et al. |
| 6,461,360 B1 | 10/2002 | Adam |
| 6,488,684 B2 | 12/2002 | Bramlet et al. |
| 6,508,819 B1 | 1/2003 | Orbay |
| 6,508,820 B2 | 1/2003 | Bales |
| 6,514,253 B1 | 2/2003 | Yao |
| 6,524,313 B1 | 2/2003 | Fassir et al. |
| 6,524,314 B1 | 2/2003 | Dean et al. |
| 6,527,775 B1 | 3/2003 | Warburton |
| 6,533,788 B1 | 3/2003 | Orbay |
| 6,547,791 B1 | 4/2003 | Buhren et al. |
| 6,554,833 B2 | 4/2003 | Levy et al. |
| 6,572,620 B1 | 6/2003 | Schon et al. |
| 6,579,294 B2 | 6/2003 | Robioneck |
| 6,607,531 B2 | 8/2003 | Frigg |
| 6,623,486 B1 | 9/2003 | Weaver et al. |
| 6,629,976 B1 | 10/2003 | Gnos et al. |
| 6,648,889 B2 | 11/2003 | Bramlet et al. |
| 6,652,529 B2 | 11/2003 | Swanson |
| 6,656,189 B1 | 12/2003 | Wilson et al. |
| 6,658,189 B2 | 12/2003 | Ajima et al. |
| 6,660,009 B1 | 12/2003 | Azar |
| 6,702,816 B2 | 3/2004 | Buhler |
| 6,702,823 B2 | 3/2004 | Iaia |
| 6,706,046 B2 | 3/2004 | Orbay et al. |
| 6,709,436 B1 | 3/2004 | Hover et al. |
| 6,712,820 B2 | 3/2004 | Orbay |
| 6,730,087 B1 | 5/2004 | Butsch |
| 6,730,090 B2 | 5/2004 | Orbay et al. |
| 6,736,818 B2 | 5/2004 | Perren et al. |
| 6,755,862 B2 | 6/2004 | Keynan |
| 6,767,351 B2 | 7/2004 | Orbay et al. |
| 6,786,908 B2 | 9/2004 | Hover et al. |
| 6,793,659 B2 | 9/2004 | Putnam |
| 6,796,984 B2 | 9/2004 | Soubeiran |
| 6,808,527 B2 | 10/2004 | Lower et al. |
| 6,866,665 B2 | 3/2005 | Orbay |
| 6,893,444 B2 | 5/2005 | Orbay |
| 6,926,720 B2 | 8/2005 | Castaneda |
| 7,018,380 B2 | 3/2006 | Cole et al. |
| 7,033,365 B2 | 4/2006 | Powell et al. |
| 7,041,104 B1 | 5/2006 | Cole et al. |
| 7,160,302 B2 | 1/2007 | Warburton |
| 7,175,633 B2 | 2/2007 | Roth et al. |
| 7,247,156 B2 | 7/2007 | Ekholm et al. |
| 7,410,488 B2 | 8/2008 | Janna et al. |
| 7,455,673 B2 | 11/2008 | Gotfried |
| 7,588,577 B2 | 9/2009 | Fencl et al. |
| 7,608,075 B2 | 10/2009 | Tornier |
| 7,655,029 B2 | 2/2010 | Niederberger et al. |
| 7,763,021 B2 | 7/2010 | Cole et al. |
| 7,763,023 B2 | 7/2010 | Gotfried |
| 7,909,825 B2 | 3/2011 | Saravia et al. |
| 7,914,532 B2 | 3/2011 | Shaver et al. |
| 8,142,432 B2 | 3/2012 | Matityahu |
| 8,157,802 B2 | 4/2012 | Elghazaly et al. |
| 8,162,950 B2 | 4/2012 | Digeser et al. |
| 8,303,590 B2 | 11/2012 | Elghazaly et al. |
| 8,394,103 B2 | 3/2013 | O'Reilly et al. |
| 8,435,238 B2 | 5/2013 | Dejardin |
| 8,460,294 B2 | 6/2013 | Overes |
| 8,486,072 B2 | 7/2013 | Haininger |
| 8,523,861 B2 | 9/2013 | Kiritsis |
| 8,523,862 B2 | 9/2013 | Murashko, Jr. |
| 8,523,919 B2 | 9/2013 | Huebner et al. |
| 8,641,741 B2 | 2/2014 | Murashko, Jr. et al. |
| 8,771,283 B2 | 7/2014 | Larsen et al. |
| 8,968,371 B2 | 3/2015 | Humphrey |
| 9,011,457 B2 | 4/2015 | Grady, Jr. et al. |
| 9,050,151 B2 | 6/2015 | Schilter |
| 9,089,375 B2 | 7/2015 | Smith et al. |
| 9,393,059 B2 | 7/2016 | Kiritsis |
| 9,597,128 B2 | 3/2017 | Boileau et al. |
| 9,662,153 B2 | 5/2017 | Larsen et al. |
| 11,065,042 B2 | 7/2021 | Garvey et al. |
| 2001/0011172 A1 | 8/2001 | Orbay et al. |
| 2002/0032446 A1 | 3/2002 | Orbay |
| 2002/0058948 A1 | 5/2002 | Arlettaz |
| 2002/0111629 A1 | 8/2002 | Phillips |
| 2002/0143337 A1 | 10/2002 | Orbay et al. |
| 2002/0143338 A1 | 10/2002 | Orbay et al. |
| 2002/0151897 A1 | 10/2002 | Zirkle, Jr. |
| 2002/0183753 A1 | 12/2002 | Manderson |
| 2003/0040748 A1* | 2/2003 | Aikins ............... A61B 17/92 |
| | | 606/70 |
| 2003/0050704 A1 | 3/2003 | Keynan |
| 2003/0055428 A1 | 3/2003 | Swanson |
| 2003/0069581 A1 | 4/2003 | Stinson et al. |
| 2003/0073999 A1 | 4/2003 | Putnam |
| 2003/0083660 A1 | 5/2003 | Orbay |
| 2003/0083661 A1 | 5/2003 | Orbay et al. |
| 2003/0105461 A1 | 6/2003 | Putnam |
| 2004/0049192 A1 | 3/2004 | Shimizu |
| 2004/0082955 A1 | 4/2004 | Zirkle, Jr. |
| 2004/0172026 A1 | 9/2004 | Ekholm et al. |
| 2005/0187550 A1 | 8/2005 | Grusin |
| 2005/0273103 A1 | 12/2005 | Wahl et al. |
| 2005/0277936 A1 | 12/2005 | Siravo et al. |
| 2006/0015101 A1 | 1/2006 | Warburton et al. |
| 2006/0015123 A1 | 1/2006 | Fencl et al. |
| 2006/0064106 A1 | 3/2006 | Fernandez |
| 2006/0069392 A1 | 3/2006 | Renzi Brivio et al. |
| 2006/0084997 A1 | 4/2006 | Dejardin |
| 2006/0084999 A1 | 4/2006 | Aschmann |
| 2006/0095039 A1 | 5/2006 | Mutchler |
| 2006/0098851 A1 | 5/2006 | Shoham et al. |
| 2006/0100623 A1 | 5/2006 | Pennig |
| 2006/0106384 A1 | 5/2006 | Reber et al. |
| 2006/0106385 A1 | 5/2006 | Pennig |
| 2006/0111717 A1 | 5/2006 | Saueressig et al. |
| 2006/0173457 A1 | 8/2006 | Tornier |
| 2006/0189987 A1 | 8/2006 | Orbay et al. |
| 2006/0200141 A1 | 9/2006 | Janna et al. |
| 2006/0200142 A1 | 9/2006 | Sohngen et al. |
| 2006/0200143 A1 | 9/2006 | Warburton |
| 2006/0200144 A1 | 9/2006 | Warburton |

(56) References Cited

U.S. PATENT DOCUMENTS

| | | |
|---|---|---|
| 2006/0235394 A1 | 10/2006 | Martin |
| 2006/0235402 A1 | 10/2006 | Celli et al. |
| 2006/0241605 A1 | 10/2006 | Schlienger et al. |
| 2007/0016203 A1 | 1/2007 | Schlienger et al. |
| 2007/0049938 A1 | 3/2007 | Wallace et al. |
| 2007/0049940 A1 | 3/2007 | Wallace et al. |
| 2007/0123873 A1 | 5/2007 | Czartoski et al. |
| 2007/0123874 A1 | 5/2007 | Czartoski et al. |
| 2007/0123875 A1 | 5/2007 | Czartoski et al. |
| 2007/0123876 A1 | 5/2007 | Czartoski et al. |
| 2007/0123878 A1 | 5/2007 | Shaver et al. |
| 2007/0156144 A1 | 7/2007 | Ulrich |
| 2007/0173834 A1 | 7/2007 | Thakkar |
| 2007/0173835 A1 | 7/2007 | Medoff |
| 2007/0173843 A1* | 7/2007 | Matityahu ............ A61B 17/80 606/281 |
| 2007/0219636 A1 | 9/2007 | Thakkar |
| 2007/0233104 A1 | 10/2007 | Metzinger |
| 2007/0255283 A1 | 11/2007 | Ekholm et al. |
| 2007/0265628 A1 | 11/2007 | Kraus et al. |
| 2007/0270848 A1 | 11/2007 | Lin |
| 2007/0276382 A1 | 11/2007 | Mikhail et al. |
| 2007/0276385 A1 | 11/2007 | Schlienger et al. |
| 2007/0288016 A1 | 12/2007 | Halder |
| 2007/0288017 A1 | 12/2007 | Kaup |
| 2007/0288019 A1 | 12/2007 | Schlienger et al. |
| 2007/0299447 A1 | 12/2007 | Watanabe et al. |
| 2008/0004623 A1 | 1/2008 | Ferrante et al. |
| 2008/0009869 A1 | 1/2008 | Schlienger et al. |
| 2008/0009873 A1 | 1/2008 | Yacoubian |
| 2008/0058813 A1 | 3/2008 | Gotfried |
| 2008/0058814 A1 | 3/2008 | Gotfried |
| 2008/0091203 A1 | 4/2008 | Warburton et al. |
| 2008/0119856 A1 | 5/2008 | Gotfried |
| 2008/0125818 A1 | 5/2008 | Sidebotham |
| 2008/0147066 A1 | 6/2008 | Longsworth et al. |
| 2008/0154264 A1 | 6/2008 | Wack et al. |
| 2008/0183171 A1 | 7/2008 | Elghazaly et al. |
| 2008/0183172 A1 | 7/2008 | Fritzinger |
| 2008/0188853 A1 | 8/2008 | Ferrante et al. |
| 2008/0195098 A1 | 8/2008 | Gotfried |
| 2008/0208261 A1 | 8/2008 | Medoff |
| 2008/0221574 A1 | 9/2008 | Cavallazzi et al. |
| 2008/0221577 A1 | 9/2008 | Elghazaly |
| 2008/0262496 A1 | 10/2008 | Schlienger et al. |
| 2008/0269751 A1 | 10/2008 | Matityahu |
| 2008/0281326 A1 | 11/2008 | Watanabe et al. |
| 2008/0287949 A1 | 11/2008 | Keith et al. |
| 2008/0294164 A1 | 11/2008 | Frank et al. |
| 2008/0300597 A1 | 12/2008 | Morgan et al. |
| 2009/0043307 A1 | 2/2009 | Faccioli et al. |
| 2009/0043310 A1 | 2/2009 | Rasmussen |
| 2009/0088752 A1 | 4/2009 | Metzinger et al. |
| 2009/0157077 A1 | 6/2009 | Larsen et al. |
| 2009/0157078 A1 | 6/2009 | Mikol |
| 2009/0157079 A1 | 6/2009 | Warburton et al. |
| 2009/0177240 A1 | 7/2009 | Perez |
| 2009/0182336 A1 | 7/2009 | Brenzel et al. |
| 2009/0209961 A1 | 8/2009 | Ferrante et al. |
| 2009/0248025 A1 | 10/2009 | Haidukewych et al. |
| 2009/0306666 A1 | 12/2009 | Czartoski et al. |
| 2009/0312760 A1* | 12/2009 | Forstein ............ A61B 17/1728 606/280 |
| 2009/0318981 A1 | 12/2009 | Kang |
| 2010/0179551 A1 | 7/2010 | Keller et al. |
| 2010/0179599 A1 | 7/2010 | Derouet et al. |
| 2010/0191240 A1 | 7/2010 | Prager et al. |
| 2010/0268229 A1 | 10/2010 | Siravo et al. |
| 2010/0318085 A1 | 12/2010 | Austin et al. |
| 2010/0331842 A1 | 12/2010 | Milbank |
| 2011/0046625 A1 | 2/2011 | Boileau et al. |
| 2011/0060337 A1 | 3/2011 | Ferrante et al. |
| 2011/0060373 A1 | 3/2011 | Russell et al. |
| 2011/0106080 A1 | 5/2011 | Schlienger et al. |
| 2011/0106086 A1 | 5/2011 | Laird |
| 2011/0137313 A1 | 6/2011 | Jensen et al. |
| 2011/0196369 A1 | 8/2011 | Osman |
| 2011/0224736 A1 | 9/2011 | Humphrey |
| 2011/0295254 A1 | 12/2011 | Brunnarius |
| 2012/0078252 A1 | 3/2012 | Huebner et al. |
| 2012/0078312 A1* | 3/2012 | Federspiel ............ A61B 17/808 606/281 |
| 2012/0109128 A1 | 5/2012 | Frigg |
| 2012/0116400 A1 | 5/2012 | Yang et al. |
| 2012/0123415 A1 | 5/2012 | Vienney et al. |
| 2012/0143192 A1 | 6/2012 | Watanabe et al. |
| 2012/0150187 A1 | 6/2012 | Gotfried |
| 2012/0157997 A1 | 6/2012 | Sohngen |
| 2012/0172875 A1 | 7/2012 | Coati et al. |
| 2012/0197255 A1 | 8/2012 | Elghazaly |
| 2012/0209268 A1 | 8/2012 | Overes |
| 2012/0226278 A1 | 9/2012 | Nardini et al. |
| 2012/0245642 A1 | 9/2012 | Giannoudis et al. |
| 2012/0245645 A1 | 9/2012 | Hanson et al. |
| 2013/0079829 A1 | 3/2013 | Globerman et al. |
| 2013/0274747 A1 | 10/2013 | Fagan et al. |
| 2013/0289626 A1 | 10/2013 | Murashko, Jr. |
| 2014/0194877 A1 | 7/2014 | Mangiardi |
| 2014/0243827 A1 | 8/2014 | Boileau et al. |
| 2015/0038968 A1 | 2/2015 | Vega et al. |
| 2015/0359576 A1 | 12/2015 | Ponce et al. |
| 2016/0022336 A1 | 1/2016 | Bateman |
| 2017/0265915 A1 | 9/2017 | Langdale et al. |
| 2018/0000496 A1 | 1/2018 | Langdale et al. |
| 2022/0142685 A1 | 5/2022 | Fluri et al. |
| 2022/0142691 A1 | 5/2022 | Smith |
| 2022/0202456 A1 | 6/2022 | Burki et al. |

FOREIGN PATENT DOCUMENTS

| | | |
|---|---|---|
| DE | 29916803 | 12/1999 |
| EP | 0091499 | 10/1983 |
| EP | 0118778 | 9/1984 |
| EP | 0355411 | 7/1989 |
| EP | 0491138 | 10/1991 |
| EP | 0462493 | 9/1994 |
| EP | 1095626 | 4/2001 |
| EP | 1330988 | 7/2003 |
| EP | 0947176 | 11/2004 |
| EP | 1685803 | 8/2006 |
| EP | 1759643 | 3/2007 |
| EP | 1779795 | 5/2007 |
| EP | 2231034 | 1/2013 |
| EP | 2548523 | 1/2013 |
| EP | 3 132 758 | 2/2017 |
| FR | 2647006 | 10/1990 |
| FR | 2668360 | 11/1990 |
| FR | 2586554 | 8/1995 |
| GB | 1428653 | 3/1976 |
| GB | 2290478 | 1/1996 |
| JP | 2274243 | 8/1990 |
| JP | 2001-286481 | 10/2001 |
| JP | 2002-528217 | 9/2002 |
| JP | 3957517 | 8/2007 |
| JP | 2011-506044 | 3/2011 |
| JP | 2013-223736 | 10/2013 |
| WO | WO 93/22978 | 11/1993 |
| WO | WO 97/018770 | 5/1997 |
| WO | WO 98/18397 | 5/1998 |
| WO | WO 00/25681 | 5/2000 |
| WO | WO 01/56452 | 1/2001 |
| WO | WO 03/037160 | 10/2002 |
| WO | WO 2006/091625 | 8/2006 |
| WO | WO 2007/035772 | 3/2007 |
| WO | WO 2009/079503 | 6/2009 |

OTHER PUBLICATIONS

"ACE Symmetry Titanium Upper Extremity Plates: New Product Release", Ace Medical Company, 1996, vol. 3, No. 3, in 8 pages.
"ACE Symmetry Titanium Upper Extremity Plates: Surgical Technique", Ace Medical Company, 1996, in 14 pages.

(56) References Cited

OTHER PUBLICATIONS

"The Alta Tibial/Humeral Rod Module for Reamed and Non-Reamed Procedures," Alta Modular Trauma System, 1992, 10 pages.
Barton, N.J., "Smith's Type I Fracture", Fractures of the Hand and Wrist, p. 254.
Damron, et al., "Biomechanical Analysis of Dorsal Plate Fixation in Proximal Phalangeal Fractures", Annals of Plastic Surgery, Apr. 1993, pp. 270-275.
Drobetz, et al., "Osteosynthesis of distal radial fractures with a volar locking screw plate system," International Orthopaedics, 2003, vol. 27, pp. 1-6.
Fitoussi, W.Y., et al., "Treatment of Displaced Intra-Articular Fractures of the Distal End of the Radius with Plates Article", JBJA Journal of Bone and Joint Surgery—American 1996-1998, Sep. 1997, vol. 79-A, No. 9, 17 pages.
"Humeral SuturePlate: Proximal Humeral Fracture Management System", Arthrex, Inc., 2012 in 8 pages.
"Intramedullary Fixation: Metaphysical/Diaphyseal Solutions," Zimmer, 2000, 6 pages.
"Intramedullary Nail for the Distal Radius," Aesculap Orthopaedics Targon DR, B-Braun, Oct. 2006, 28 pages.
Melone, C.P., "Distal Radius Fractures: Patterns of Articular Fragmentation", Orthopedic Clinics of North America, Apr. 1993, vol. 24, No. 2, pp. 239-253.
"The Next Generation in Nail Fixation: Symposium: Current Concepts in Femoral Nailing," Feb. 1993, vol. 26, No. 2, 35 pages.
Orbay, et al., "The Treatment of Unstable Distal Radius Fractures with Volar Fixation", Hand Surgery, Dec. 2000, vol. 5, No. 2, pp. 103-112.
Orbay, et al., "Volar Fixation for Dorsally Displaced Fractures of the Distal Radius: A Preliminary Report", The Journal of Hand Surgery, 2002, pp. 205-215.
"Proximal Humeral Nailing System: Operative Technique," Stryker Corporation, 2003, 20 pages.
"RAL Nail System: Titanium for Your Most Demanding Cases," ACUMED 00674, 13 pages.
Smith, et al., "Open Reduction and Internal Fixation of Volar Lip Fractures of the Distal Radius", Journal of Orthopaedic Trauma, 1988, vol. 2, No. 3, pp. 181-187.
"Synthes 3.5 mm LCP Proximal Humerus Plates: Technique Guide", Synthes, Inc., 2002, in 58 pages.
"TiMAX Pe.R.I. Small Fragment Upper Extremity", DePuy ACE, 1999 in 2 pages.
"Uniflex Humeral Nail System," Biomet Inc., 1991, 16 pages.
International Search Report and Written Opinion issued in PCT Application No. PCT/US2018/055290, dated Mar. 28, 2019, in 21 pages.

\* cited by examiner

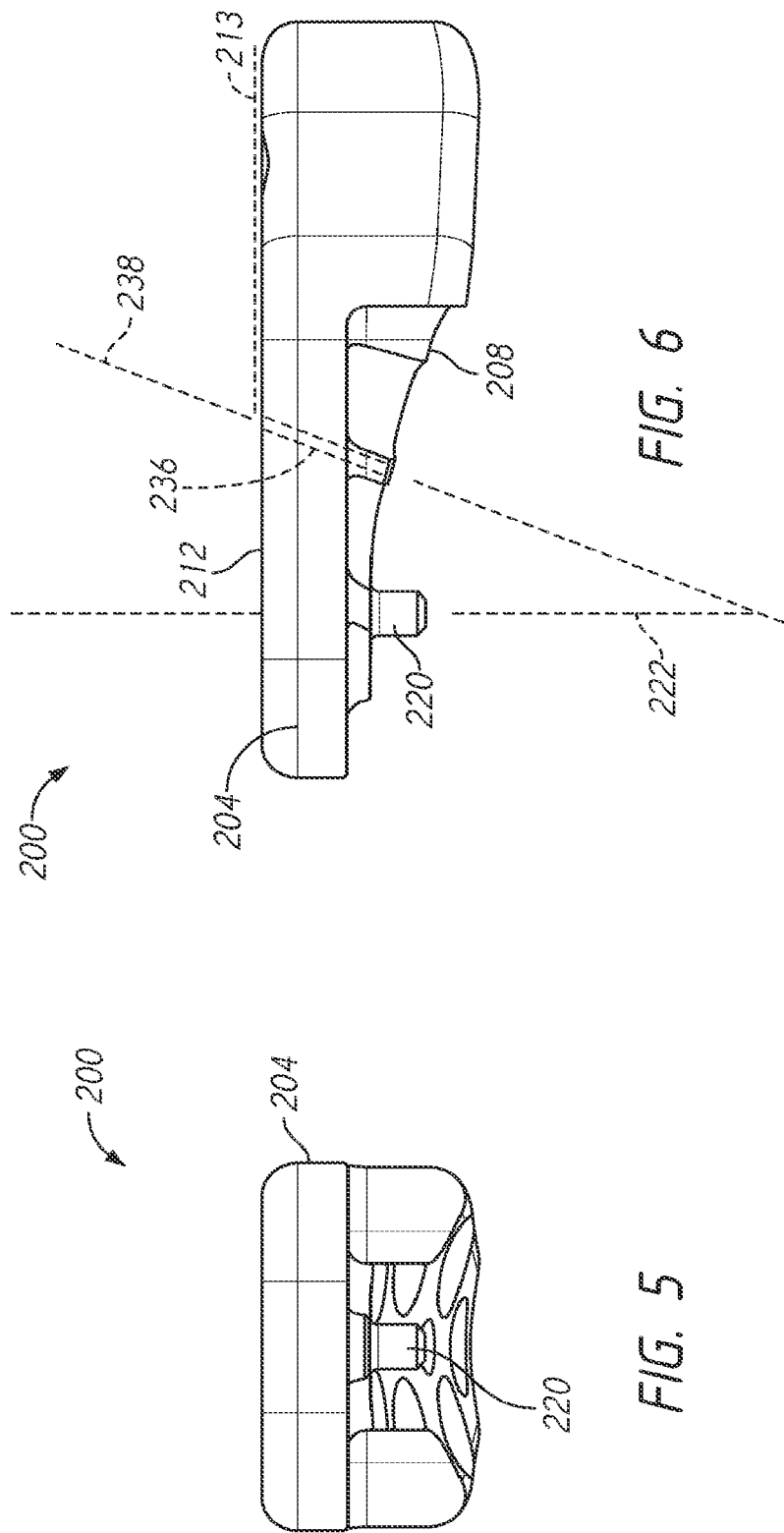

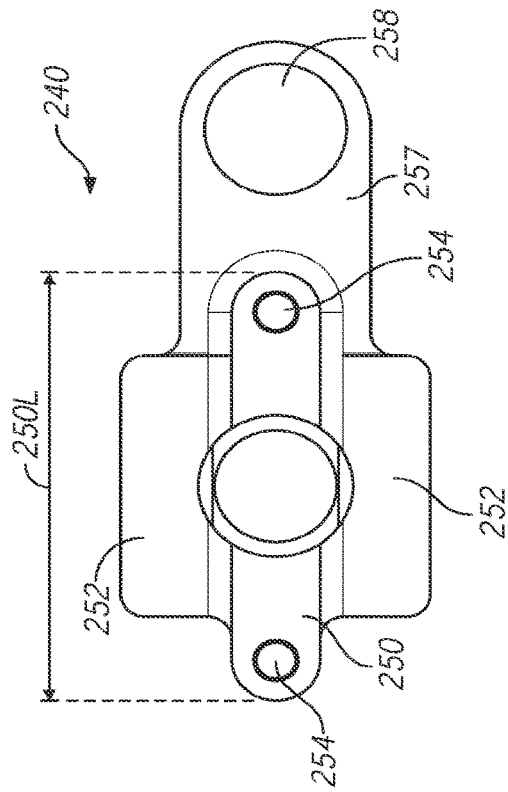
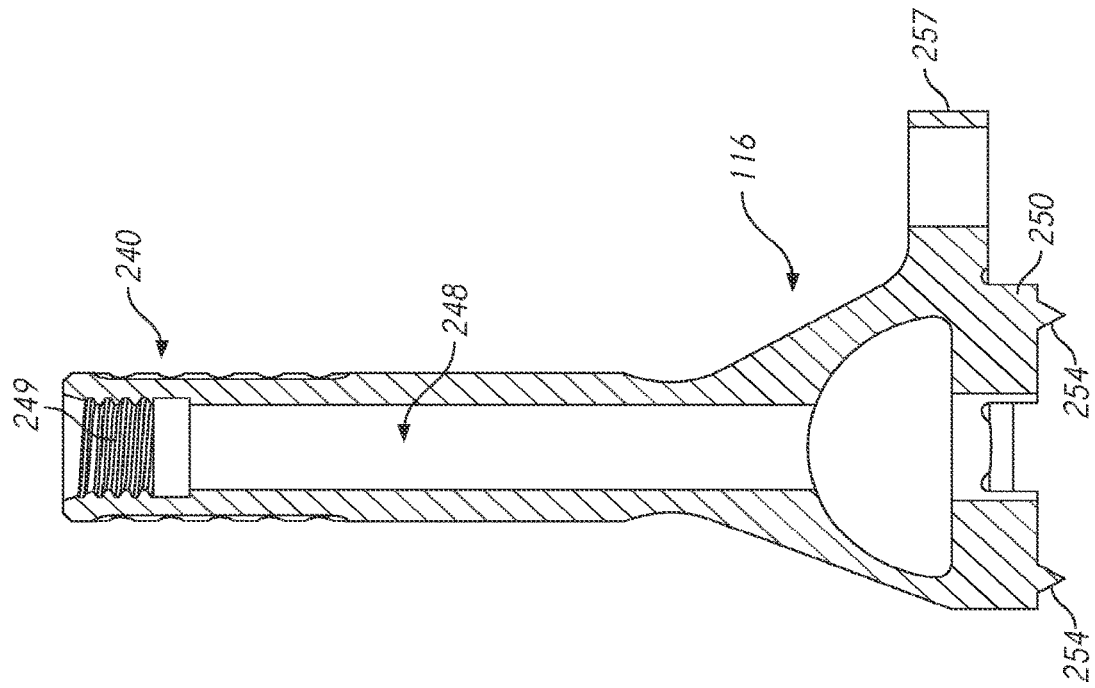
FIG. 7E
FIG. 7D

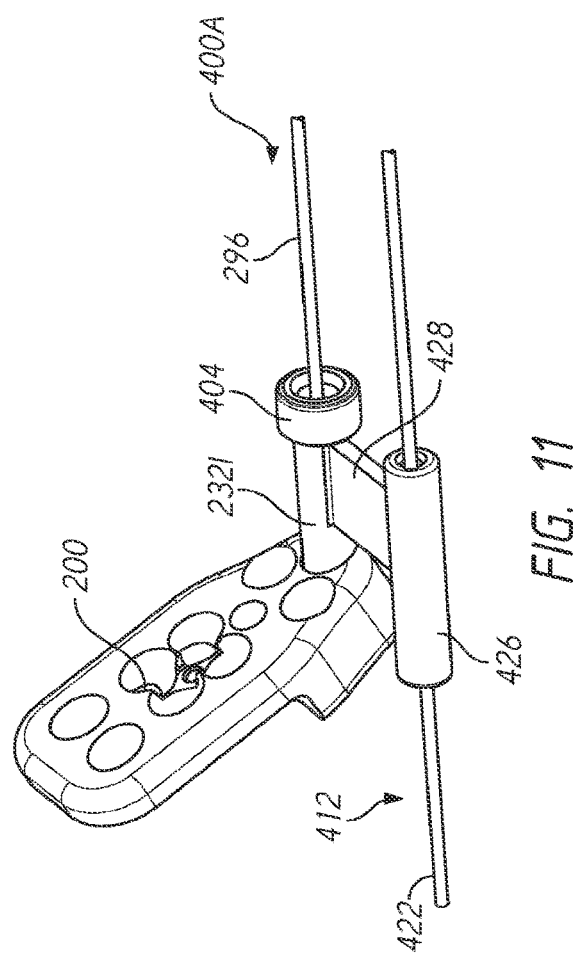
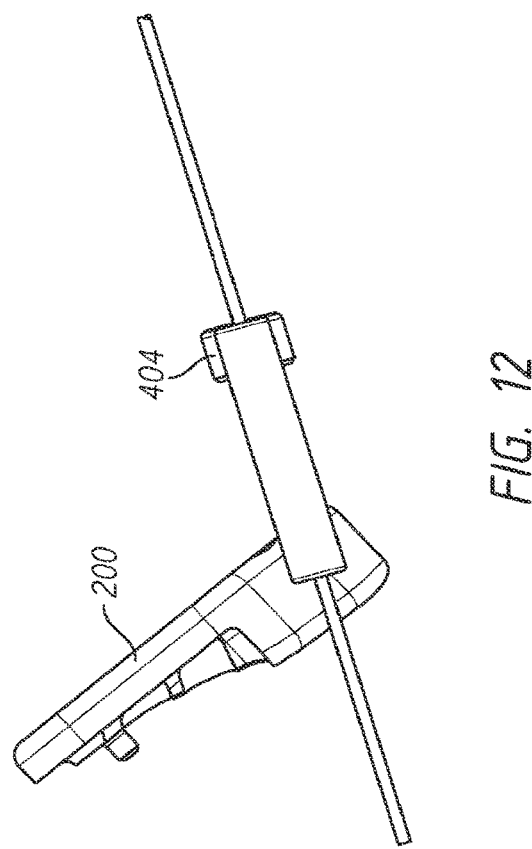
FIG. 11
FIG. 12

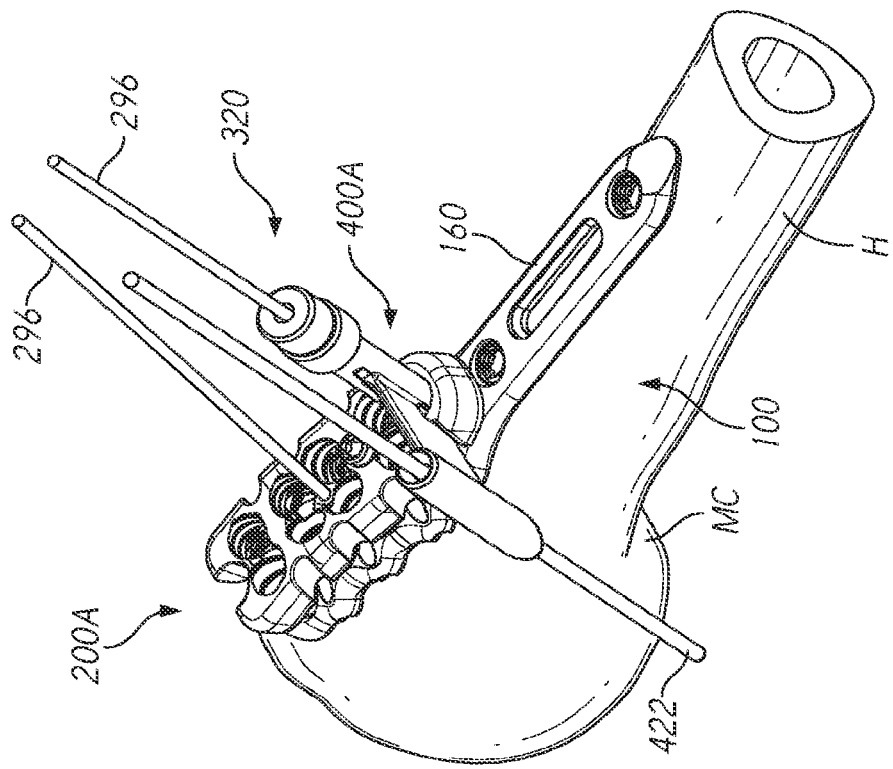
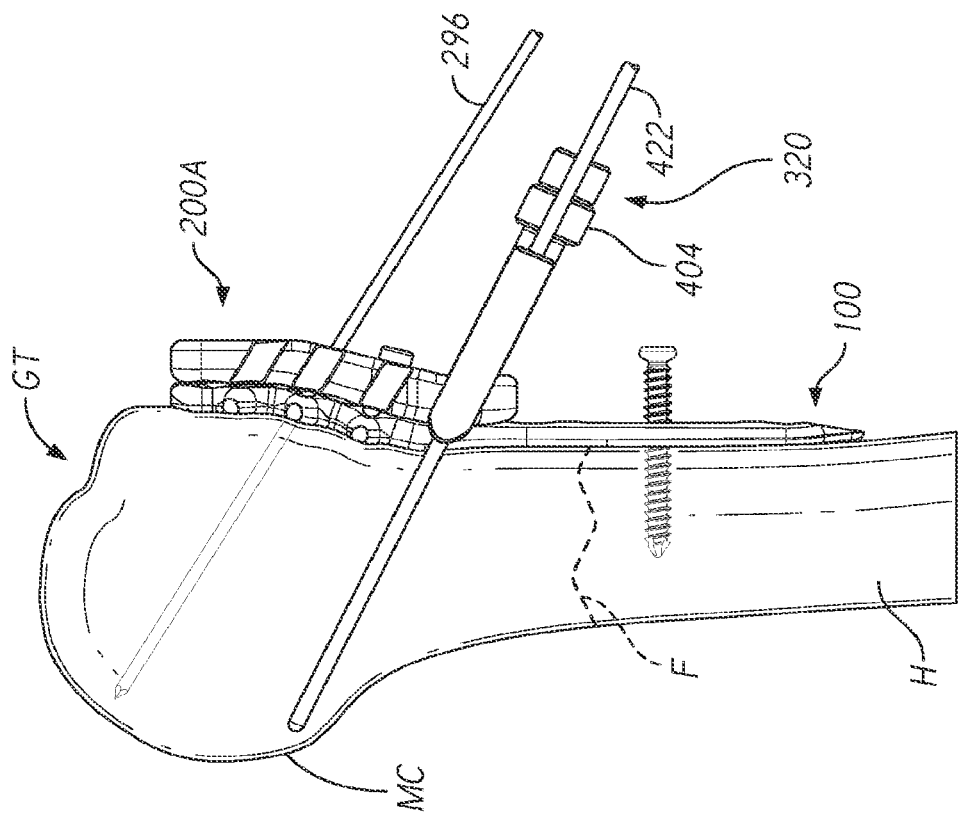
FIG. 14
FIG. 13

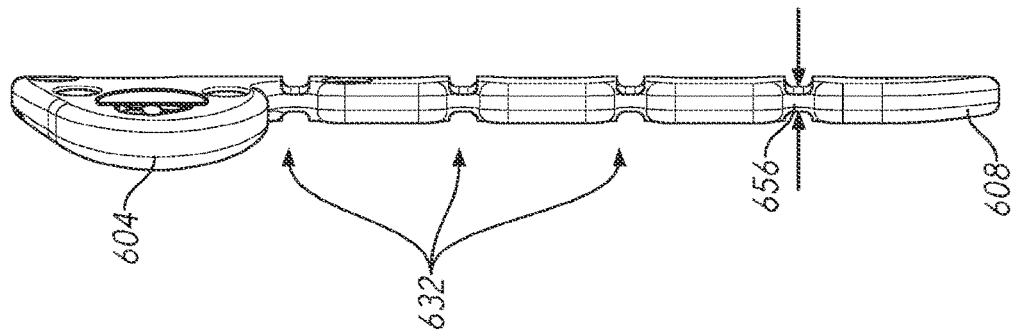
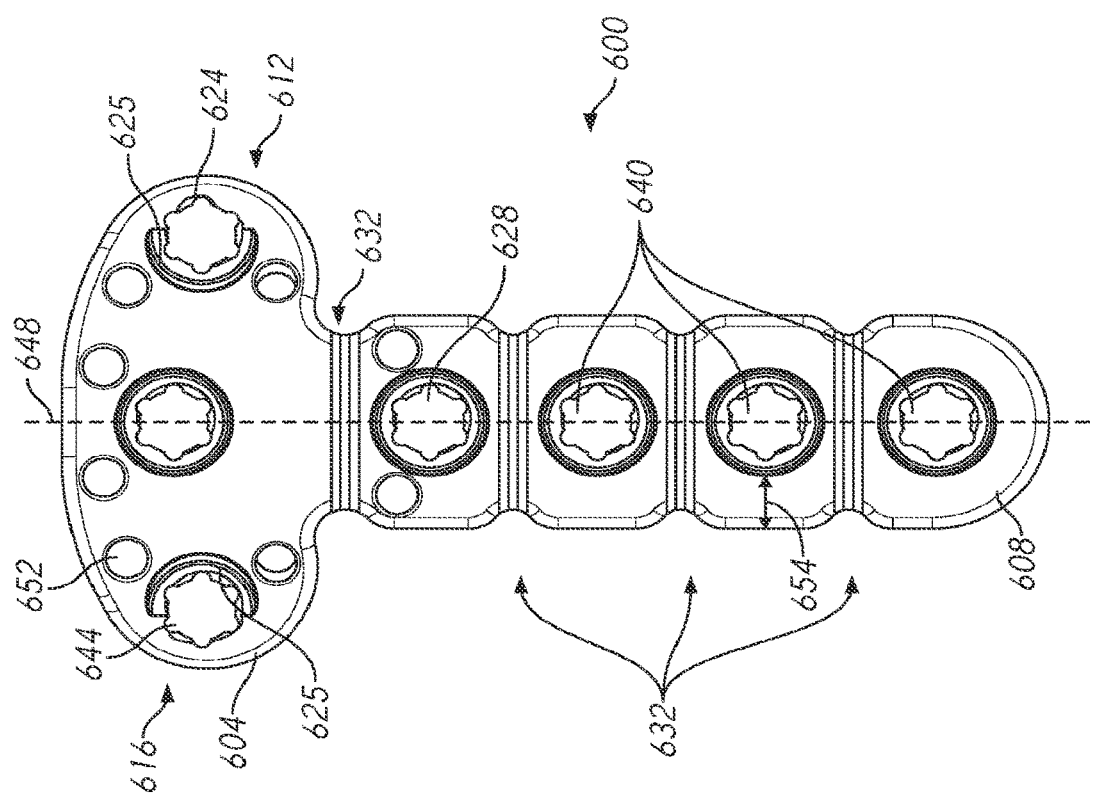
FIG. 30B
FIG. 30A

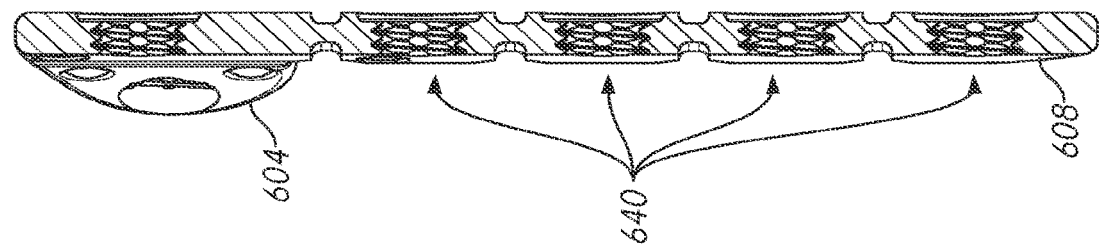
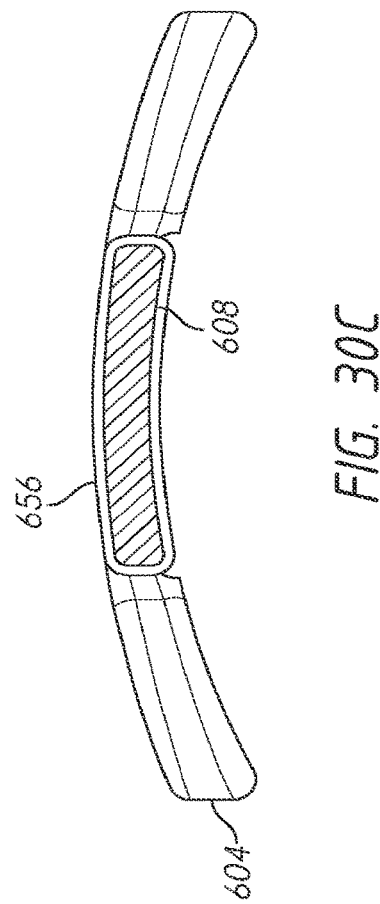

HUMERAL FIXATION PLATES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to guides for controlled insertion of fasteners into bone fracture plates, e.g., for the humerus, and for fracture repair and methods of using the same.

Description of the Related Art

Humeral fractures arise from serious injuries and other causes. One approach to repairing fracture involves attaching a fracture plate to an outside surface of the humerus to fix exposed sides of the facture onto or adjacent to one another to facilitate the process of fusing these exposed sides together. The fracture plate assures that the multiple pieces of the fractured bone remain in a prescribed position or orientation to each other and do not move relative to each other so that the fusion process is not continually disrupted and so that the bones do not migrate to and fuse in misaligned positions.

Humeral bone has several layers. An outer layer called the cortical layer is a relatively dense portion of the humerus that is most capable of bearing loads absent other bone considerations. Inward of the cortical layer is cancellous bone matter. This bone matter is less dense and is not as capable of bearing loads. A number of screws can be used to secure a fracture plate to the humerus. These screws should be lodged in the cortical bone or in a transition between cancellous and cortical bone to provide good fixation of the fracture plate to the bone, and thereby of the multiple pieces of the fractured humerus to each other.

Because fracture plates are typically coupled with the lateral side of the humerus and the screws are typically directed into the humeral head, it is important to control the final location of the tips of the screws.

SUMMARY OF THE INVENTION

It would be desirable to provide improved apparatuses and methods for securing a fracture plate to a humerus. It would be advantageous to provide a guide that can be used to direct fasteners into the humeral bone in a way that provides robust connection of the fasteners to strong hone, e.g., to cortical hone, of the humerus. In some applications the guides can be configured to provide a prescribed pattern of fasteners projecting from a fracture plate. The prescribed pattern can be controlled by a guide that is appropriate for the humerus, e.g., appropriate for the size and location (left, right) of the humerus. The prescribed pattern could be unique to a specific patient based on pre- or intra-operative imaging. The guides can enable a non-patient specific fracture plate to be used with humerus bones of different size and in some cases in patient specific method, e.g., resulting in proper placement of the fracture plate and of a plurality of fasteners.

In one embodiment, an anchor trajectory guide is provided that includes a body that has a medial side. The medial side is configured to be placed over a lateral side of a fixation plate. The anchor trajectory guide also includes a locator and a plurality of guide apertures. The locator is disposed on or through the medial side of the body. The locator is configured to mate with the fixation plate. The guide apertures are disposed through the body at positions corresponding to define anchor locations and orientations to provide good fixation in bone around a medial portion of a humerus.

In another embodiment an anatomical guide is provided. The anatomical guide is configured to be coupled with a sleeve and a visual guide member. The sleeve is configured to mate with a guide aperture of an anchor trajectory guide or with a fixation plate. The sleeve can have a lumen that is disposed therethrough. The lumen can be used to advance a K-wire or other pin through the anatomical guide. The visual guide member is configured to extend from the anchor trajectory guide or the fixation plate to an anterior side or a posterior side of the humerus.

In another embodiment a method is provided. In the method, a medial side of a fixation plate is placed on a lateral surface of a humerus. The fixation plate is placed in contact with the lateral surface. The fixation plate is coupled with the humerus spanning a fracture. A medial side of an anchor trajectory guide is coupled with a lateral side of the fixation plate. An anchor channel is formed in the humerus from the lateral side of the humerus toward an opposing cortical bone region. The anchor channel can be formed, through a guide aperture in the anchor trajectory guide and an anchor aperture in the fixation plate. An anchor is advanced through the anchor aperture and the anchor channel, which is formed in the bone, to secure the anchor and the fixation plate to the humerus. The anchor follows a trajectory defined by the anchor trajectory guide. A medial end of the anchor is embedded in or adjacent to the opposing cortical hone while a proximal end of the anchor is embedded in lateral cortex of the humerus. When the medial end is embedded adjacent to opposing cortical bone the medial end can be lodged in cancellous bone. When the medial end is embedded adjacent to opposing cortical bone the medial end can be lodged in a transitional bone matter between the cancellous bone and the cortical bone.

In another embodiment, a slot anchor guide is provided that includes a medial portion and a lateral portion. The medial portion has a medial projection configured to span a slot of a fixation plate. The slot anchor guide is configured to guide an anchor through a predetermined position of a slot of the fixation plate. The slot anchor guide is configured to mate with the fixation plate to allow a surgeon to place the fixation plate on a bone face by manipulating the lateral portion.

In another embodiment, a tuberosity fracture plate is provided. The tuberosity fracture plate has a tuberosity end, a distal portion, a first screw hole and a second screw hole. The tuberosity end has a first portion configured to overlay a first tuberosity and a second portion opposite the first portion. The distal portion is coupled with and extends away from the tuberosity portion. The first screw hole is disposed in the tuberosity end. The second screw hole is disposed in the distal portion. The tuberosity fracture plate has a bend zone disposed between the first screw hole and the second screw hole. The bend zone is configured to locate a bend in the tuberosity fracture plate between the first screw hole and the second screw hole upon application of a load to the tuberosity end, to the distal portion or to both the tuberosity end and the distal portion.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 5 is a view of a superior side of the anchor trajectory guide of FIG. 3;

FIG. 6 is a view of an anterior side of the anchor trajectory guide of FIG. 3;

FIG. 7D is a cross-sectional view of the slot anchor guide of FIG. 7B taken through section plane 7D-7D in FIG. 7C;

FIG. 7E is a medial side view of the slot anchor guide of FIG. 7B;

FIGS. 11 and 12 are examples of another medial calcar guide;

FIGS. 13 and 14 show variations methods of confirming the position of the fixation plate using the medial calcar guide of FIG. 10;

FIG. 30A is a perspective view of a tuberosity fracture plate.

FIG. 30B is a view of an anterior side of the tuberosity fracture plate of FIG. 30A;

FIG. 30C is a view of a superior side of the tuberosity fracture plate of FIG. 30A; and FIG. 30D is a cross sectional view of the tuberosity fracture plate of FIG. 30A.

DETAILED DESCRIPTION OF THE PREFERRED EMBODIMENT

This application is directed to a guide for attaching a fixation plate to a humerus of a patient and to plates that can be so attached. The guide could be used following a fracture. The fracture can be between the metaphysis and the diaphysis of the humerus or along a prominence of a proximal portion of a humerus, such as a tuberosity. Although the guides and methods are described in connection with the humerus the guides and methods can be used for other bones, such as any long bone fracture or for other orthopedic plate fixation procedures.

Figure 1A:
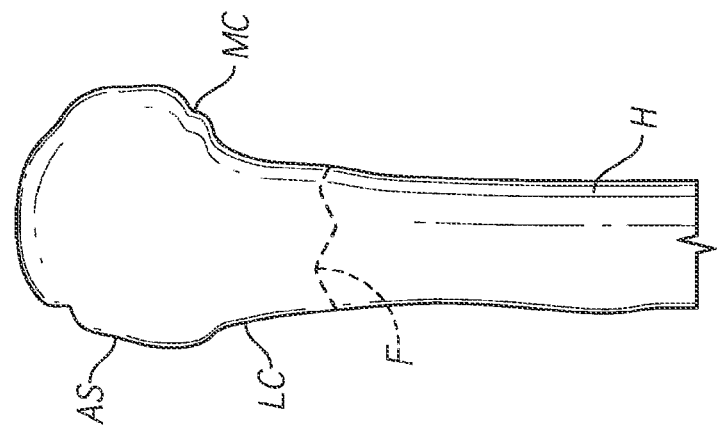
FIG. 1A is a schematic view of a proximal humerus with a two-piece fracture.
Figure 1:
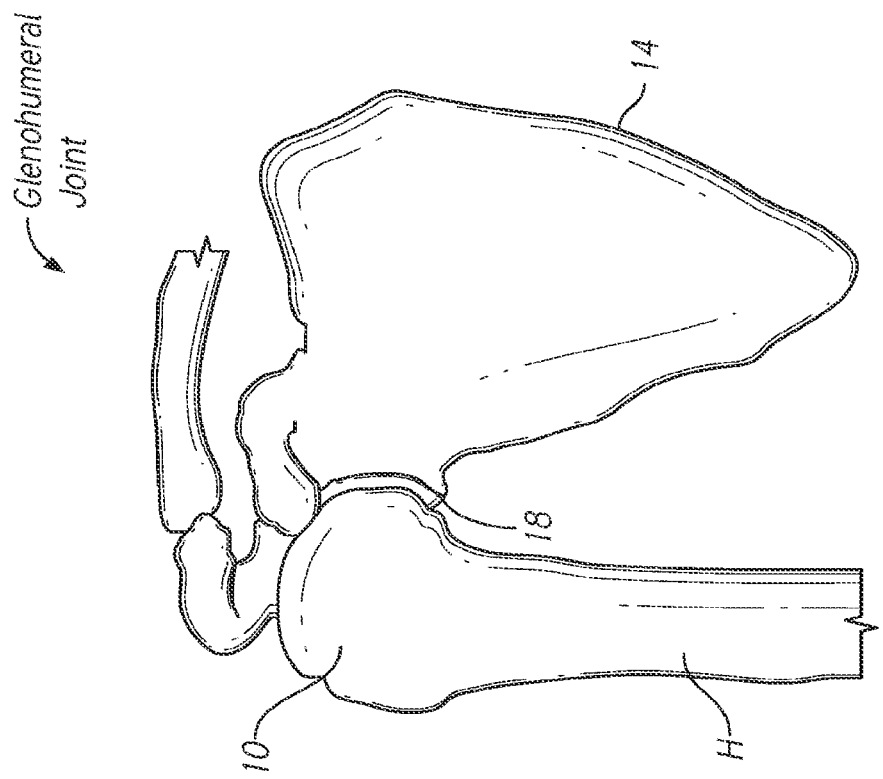
FIG. 1 is a schematic view of anatomy around the shoulder joint.

FIG. 1 shows anatomy of a glenohumeral joint. The joint is formed in part by a head 10 of a humerus H and a glenoid 18 of a scapula 14. The head 10 is a convex structure that is generally spherical. The glenoid 18 includes a concave articular surface upon which the head 10 moves. FIG. 1A shows that the humerus H has a medial side (right side in the view) and a lateral side (left side in the view). The medial calcar MC is located at the inferior edge of the head 10 on the medial side of the humerus. A lateral cortex LC extends along the lateral side of the bone generally opposite to the medial calcar MC. An anterior-superior region AS of the humerus H is located on the lateral side and superior to the distal-proximal location of the medial calcar MC.

As discussed above, the humerus has a proximal portion that is the portion of the humerus adjacent to the glenoid 18 and forming part of the shoulder joint. The proximal humerus is sometimes referred to herein as the superior humerus. Proximal and distal in this sense are shown on FIG. 1A with reference to the humerus. In this application a location that is distal to another location refers to being closer to an inferior or elbow-adjacent end of the humerus. A distal portion of the humerus is sometimes referred to herein as an inferior portion of the humerus.

FIG. 1A shows a fracture F which is one simple form of fracture that can be treated by the apparatuses and methods discussed below. In many cases the fracture F is accompanied by additional fractures around the humeral head 10. These additional fractures can be treated as well, as discussed further below.

Figure 1C:
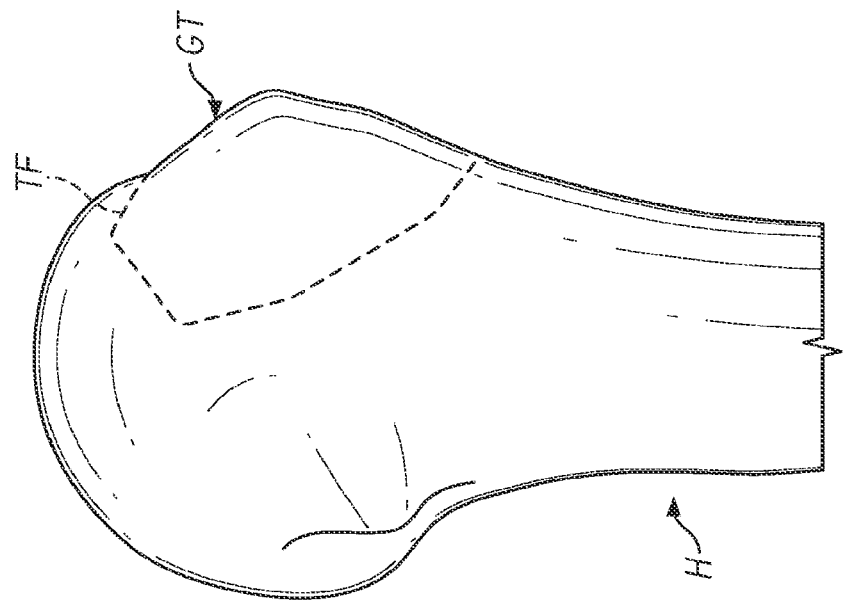
FIG. 1C is an antero-lateral view of the proximal portion of the humerus of FIG. 1B.
Figure 1B:
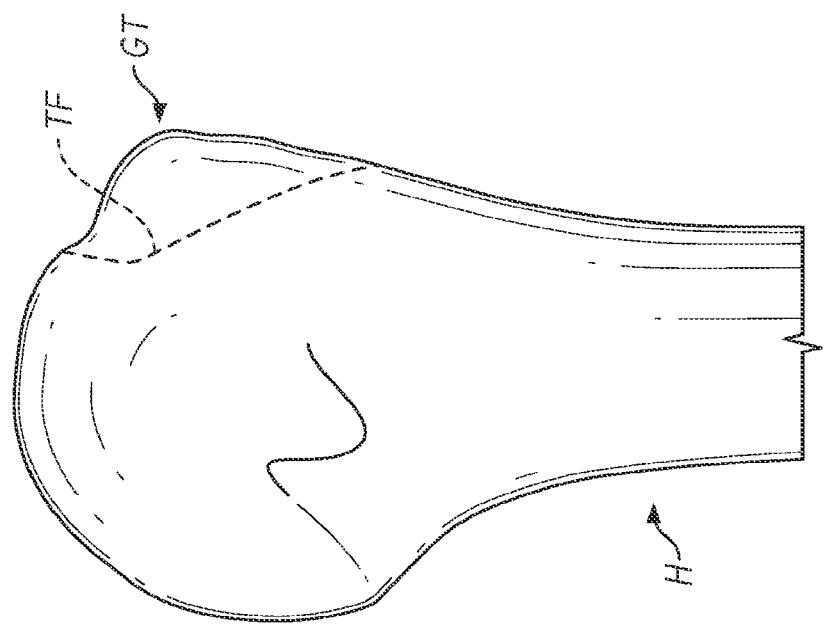
FIG. 1B is an anterior view of a proximal portion of a humerus with a tuberosity fracture.

FIGS. 1B and 1C show an example of a tuberosity fracture TF that can be treated as discussed below with a plate that is suitable for repairing the tuberosity fracture TF. The tuberosity fracture TF is of a greater tuberosity GT but could be of the lesser tuberosity LT or another prominence of a long bone.

I. Fixation Plate Assemblies

Figure 2:
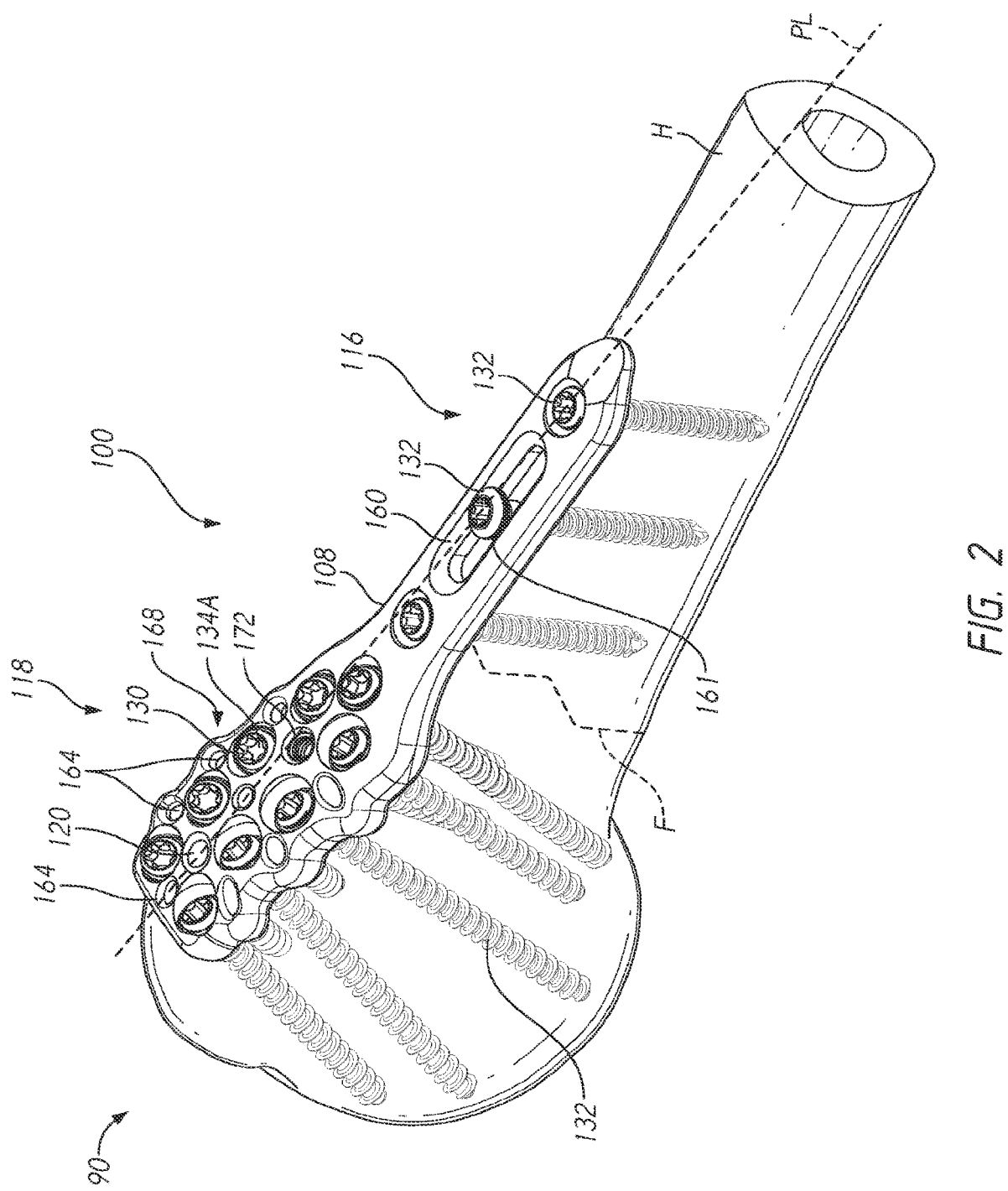
FIG. 2 is a perspective view of a fixation plate coupled to a proximal humerus by a plurality of screw anchors.

FIG. 2 shows how a fracture F in a humerus H can be treated using a fixation plate assembly 90. The fixation plate assembly 90 includes a fixation plate 100 and a plurality of polyaxial anchors 130 in one embodiment. The fixation plate 100 can have a lateral side 108 configured to face away from the humerus H and a medial side 112 (see FIG. 7) configured to face the humerus H. The medial side 112 can be in direct contact with a lateral surface IS of the humerus H in some applications. The fixation plate 100 preferably is configured to work well for an entire population of patients. The proximal-distal dimensions enable the fixation plate 100 to span a wide range of neck fractures. The anterior-posterior dimensions allow the fixation plate 100 to be placed on the lateral surface LS of a wide range of bone sizes.

The fixation plate 100 can include a distal portion 116 and a proximal portion 118. In some methods, the distal portion 116 is disposed between the humeral neck and the end of the humerus H forming a portion of the elbow joint. In some methods, the distal portion 116 is disposed between the fracture F and the end of the humerus H forming a portion of the elbow joint. In some methods the proximal portion 118 is positioned proximal of the humeral neck or of the fracture F. The proximal portion 118 can be configured to be secured to the lateral surface LS of the humerus H in the region of the head of the humerus H. For example, the proximal portion 118 can include an array of anchor apertures 134. The anchor apertures 134 can be disposed about the periphery of the proximal portion 118 of the fixation plate 100. In one embodiment, there are four anchor apertures 134 on an anterior side of the proximal portion 118 and there are an additional four anchor apertures 134 on a posterior side of the proximal portion 118 of the fixation plate 100. In some variations there can be more than four anchor apertures 134 on the anterior and posterior sides. In some variations there can be more anchor apertures 134 on the anterior than on the posterior side. In some variations there can be more anchor apertures 134 on the posterior than on the anterior side.

One or more or all of the anchor apertures 134 can be suited to mate with polyaxial anchors 130. The engagement between the polyaxial anchor 130 and the anchor aperture 134 allow the anchor to be directed along a range of directions rather than just being directed along a single axis as is provided with a more simple thread arrangement. As discussed further below, the fixation plate 100 enables a medial end 142 of the polyaxial anchors 130 to span across cancellous bone of the humerus H to engage an opposing cortical hone region CB. A lateral end 146 of the polyaxial anchors 130 is configured to engage cortical bone at or adjacent to the lateral surface LS of the humerus H. The lateral end 146 also has a head portion 134A that is configured to engage a corresponding one of the anchor apertures 134.

Figure 27:
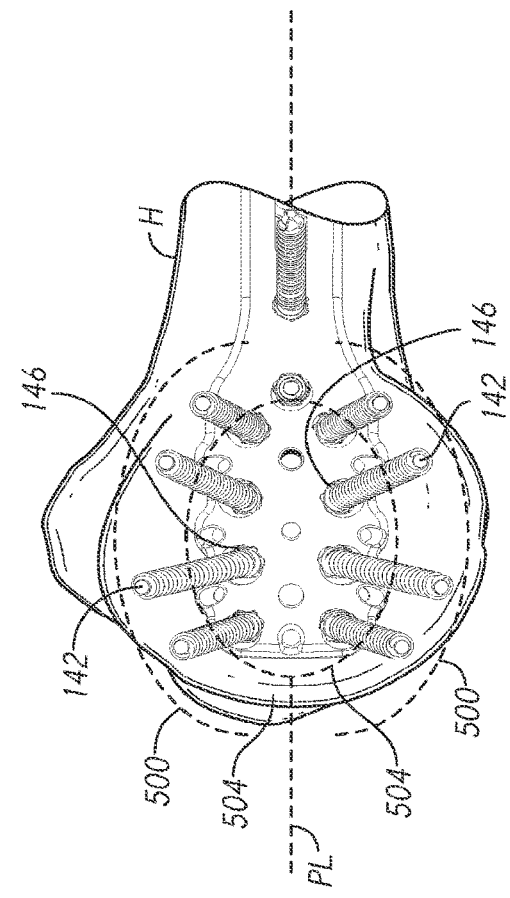

FIG. 2 and FIG. 27 show that when the fixation plate 100 is coupled with a humerus H the polyaxial anchors 130 are generally splayed out. In this specification two anchors are splayed when they are disposed in space along longitudinal axes that are not parallel to each other. FIGS. 2 and 27 show that the anchors 130 are generally splayed out with respect to a medial-lateral and proximal-distal plane PL of the humerus H. That is, a plurality of, e.g., four, polyaxial anchors 130 can be secured through an anterior portion of the fixation plate 100 to the lateral surface LS of the humerus H. Another plurality of, e.g., four, polyaxial anchors 130 can be secured to a posterior portion of the fixation plate 100 to the lateral surface LS of the humerus H. The polyaxial anchors 130 can be oriented such that medial ends 142 thereof are more anterior or more posterior than are lateral ends 146 thereof. Described another way, the lateral ends 146 can be located closer to the medial-lateral and proximal-distal plane PL than are the medial ends 142 thereof. FIG. 2 and FIG. 27 also show that the fixation plate 100 can be configured to engage some anchors along the medial-lateral and proximal-distal plane PL For example, one polyaxial anchor 130 can be disposed on the medial-lateral and proximal-distal plane PL in a central portion of the fixation plate 100. Also, one or a plurality of, e.g., two, polyaxial anchors 130 can be secured to anchor apertures 134 in the distal portion 116 of the fixation plate 100 and therethrough to a portion of the humerus H distal to the head 10 or distal to the fracture F.

Some advantageous methods discussed herein aid in initial placement of the fixation plate 100 such that the initial placement normally does not require repositioning and thus is normally the final placement. The fixation plate 100 includes a slot 160 in the distal portion 116 that facilitates some of these methods. The slot 160 can extend along a length of the distal portion 116. In some embodiments the slot 160 is aligned with a longitudinal axis of the fixation plate 100 and so can be positioned to symmetrically straddle the medial-lateral and proximal-distal plane PL. The slot 160 can have a smooth inner surface 161 to engage with a non-locking anchor 132 (see FIG. 2). The slot 160 allows the fixation plate 100 to move in a proximal-distal direction and also to rotate about the non-locking anchor 132 prior to placement of other anchors through the fixation plate 100.

The fixation plate 100 can have one or a plurality of suture apertures 164 disposed about the periphery thereof. The suture apertures 164 enable a surgeon to secure fracture portions to the fixation plate 100. In some cases fractured portions of the head can include the greater and/or the lesser tuberosities. These bone portions are usually attachment points for soft tissue, e.g., rotator cuff portions. The soft tissue tends to pull these fractured pieces medially. The suture apertures 164 can be used to pull these fracture pieces back laterally to engagement with the rest of the head 10 of the humerus H such that the humerus can heal properly. In the illustrated embodiment there are four suture apertures 164 on each of the anterior and posterior side of the fixation plate 100. Also, there can be one or two suture apertures 164 on the proximal end of the fixation plate 100. In some embodiments, the suture apertures 164 on the anterior side of the fixation plate 100 are oriented anteriorly. In some embodiments, the suture apertures 164 on the posterior side of the fixation plate 100 are oriented posteriorly. The suture apertures 164 can be oriented away from the center of the fixation plate 100.

Certain embodiments are configured to keep the fixation plate 100 on a small surface area. Accordingly, the fixation plate 100 can be located on the lateral surface LS and not extend around to the anterior surface or the posterior surface of the humerus H. In some cases, the fixation plate 100 includes scallops 168 that are located between the suture apertures 164. The scallops 168 reduce the anterior and posterior extent of the fixation plate 100, keeping the plate as low profile in the anterior and posterior directions.

The fixation plate 100 can be configured to mate with an anchor trajectory guide 200, which is discussed below in FIGS. 3-6. For example, the fixation plate 100 can have a locating aperture 120. The locating aperture 120 can extend from the lateral side 108 toward the medial side 112. The locating aperture 120 can extend from the lateral side 108 to an end portion within the thickness of the fixation plate 100, e.g., as a blind hole. The locating aperture 120 can extend entirely through the thickness of the fixation plate 100 from the lateral side 108 to the medial side 112. Other approaches can be provided to mate the anchor trajectory guide 200 with the fixation plate 100 can include providing a protrusion on the lateral side 108 of the fixation plate 100 that extends laterally toward and into the anchor trajectory guide 200. In some cases, the lateral side 108 has contours that mate in a positive-negative manner with a medial side 208 of the anchor trajectory guide 200. In this sense positive-negative manner refers to a concavity in one of the lateral and medial sides 108 208 being configured to be received in a convexity formed at a corresponding location of the other of the lateral and medial sides 108, 208.

The fixation plate 100 can also include a coupling aperture 172 that can used to further secure the fixation plate 100 to the anchor trajectory guide 200. The coupling aperture 172 can also be seen in FIG. 7F. The coupling aperture 172 can be a through-hole or a blind recess. The coupling aperture 172 can include threads to engage a screw that is advanced through the anchor trajectory guide 200 as discussed further below.

In some cases, it may be beneficial to form the fixation plate 100 as a patient specific device. For example the medial side 112 of the fixation plate 100 in the proximal portion 118 can be formed with a curvature matching the curvature of the head 10 of the humerus H of the specific patient being treated. Also, the location of a change in curvature or profile from the proximal portion 118 to the distal portion 116 can be selected to match the location of the transition from the long shaft portion of the humerus H to the head 10 thereof. Also, although the anterior-posterior coverage of the fixation plate 100 is generally kept as small as possible, the curvature in this direction on the medial side 112 of the fixation plate 100 can be configured to match that of the lateral surface LS of the humerus H. An anterior-posterior curvature of the medial side 112 in the proximal portion 118 can be different from, e.g., larger than, that of the distal portion 116 of the fixation plate 100.

A process for forming a patient specific version of the fixation plate 100 can include obtaining imaging of (e.g., pre- or intra-operative imaging) a humerus. The imaging can be that of the humerus H that is affected and to be treated. In certain fractures portions of the lateral surface LS are not altered by the fracture. For example, the fracture illustrated in FIG. 3 does not affect the lateral surface LS of the head 10 of the humerus H. So, the curvature thereof can be obtained even from an image of the fractured humerus H. Similarly the curvature of the humerus H distal the fracture F may be unaffected by the fracture. In other cases the fracture is such that the form of the lateral surface LS of the humerus H in the fracture state does not provide good information about the proper shape of the fixation plate 100. In such cases, imaging (either pre-operative or intra-operative) of the contralateral humerus H can provide a good approximation of patient specific features discussed above. Once the form of the fixation plate 100 is determined from the imaging the fixation plate 100 can be formed using additive manufacturing techniques, such as 3D printing, DMRS, and other similar techniques.

Figure 2A:
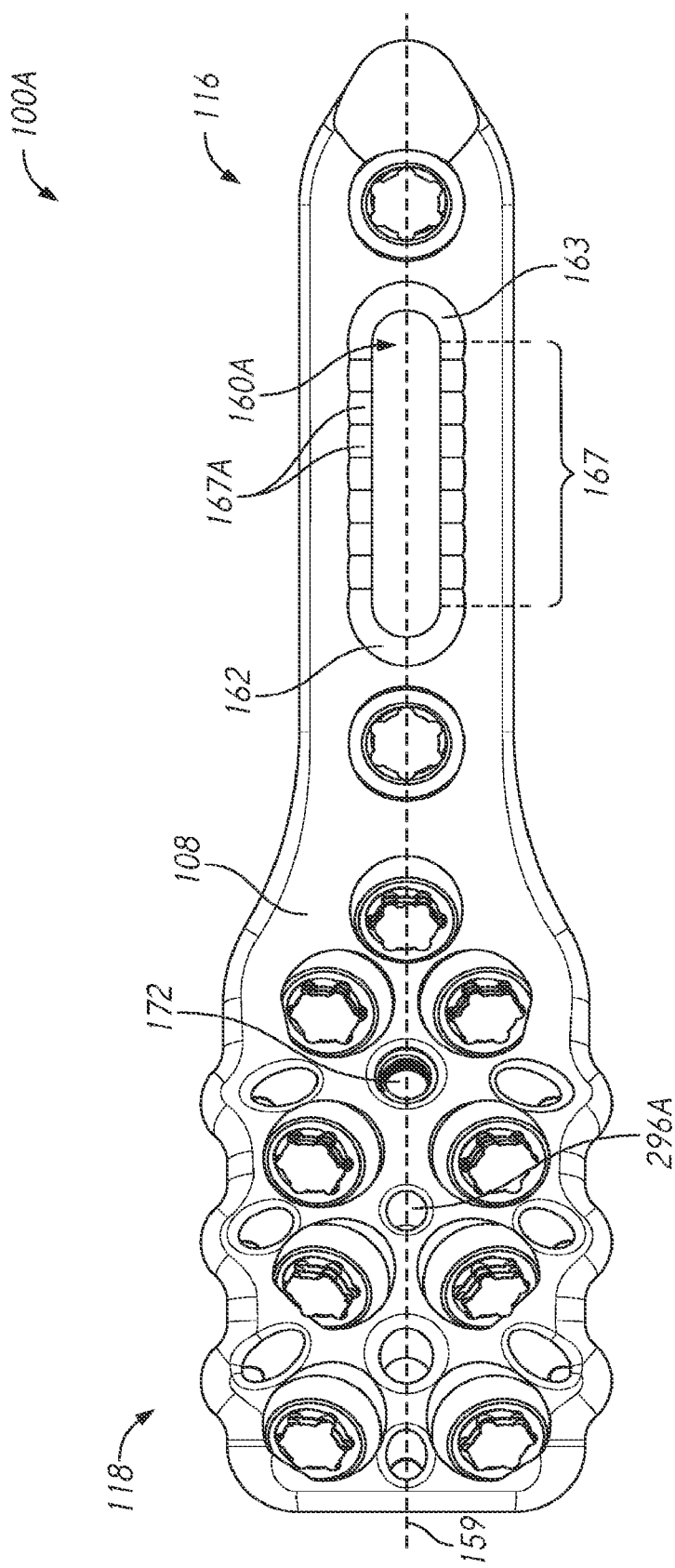
FIG. 2A is a view of a lateral side of another embodiment of a fixation plate.

FIG. 2A illustrates a humeral fixation plate 100A that is similar to the humeral fixation plate 100 except as described differently above or elsewhere herein. The disclosure of the humeral fixation plate 100 can supplement the disclosure of the humeral fixation plate 100A. The disclosure of the humeral fixation plate 100A can supplement the disclosure of the humeral fixation plate 100

The humeral fixation plate 100A includes a lateral side 108 and a medial side 112. The lateral side 108 is the portion of the humeral fixation plate 100A that faces away from the humerus H when the humeral fixation plate 100A is applied thereto. The medial side 112 is the portion of the humeral fixation plate 100A that contacts the humerus H when the humeral fixation plate 100A is applied thereto. The humeral fixation plate 100A has a thickness between the lateral side 108 and medial side 112 that can be uniform such that the plate is generally uniformly stiff along a longitudinal axis 159 thereof. For example, the humeral fixation plate 100A can respond to typical load in surgery by not preferentially bending at any particular location there. In a modified embodiment, the humeral fixation plate 100A can have a bend zone, e.g., a thinner region as discussed below in connection with the tuberosity fracture plate 600 such that the humeral fixation plate 100A can be shaped intra-operatively.

The humeral fixation plate 100A can have a distal portion 116 and a proximal portion 118. The proximal portion 118 generally can be configured to overlay a proximal portion of the humerus H when applied thereto. The distal portion 116 can be configured to extend distal of the metaphysis of the humerus H and can overlay a portion of a diaphysis of the humerus H when applied thereto. In some applications the distal portion 116 can be disposed across a fraction of the humerus H, e.g., as shown in FIGS. 1A and 2. The proximal portion 118 can be configured to be connected to a head portion of the humerus H. The proximal portion 118 can be wider in a direction transverse to the longitudinal axis 159 and to the thickness of the humeral fixation plate 100A than is the distal portion 116.

The humeral fixation plate 100A can have a slot 160A that is similar to the slot 160 except as described differently. The slot 160A can be disposed through the distal portion 116 from the lateral side 108 to the medial side 112 of the humeral fixation plate 100A. The slot 160A can extend along the longitudinal axis 159. The slot 160A can extend from a first end 162 to a second end 163 along the longitudinal axis 159. The first end 162 can be disposed adjacent to the proximal portion 118. The second end 163 can be disposed adjacent to the distal end of the humeral fixation plate 100A. The slot 160A enables the surgeon to adjust the position of the humeral fixation plate 100A relative to the humerus H along a proximal-distal (or inferior-superior) direction.

Figure 2C:
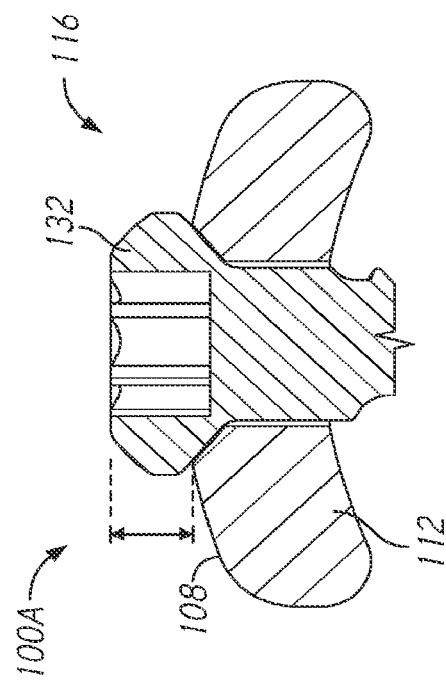
FIG. 2C is a cross-sectional view of the slot and screw of FIG. 2B taken through section plane 2C-2C in FIG. 2B.

The slot 160A can have a plurality of discrete position sites 167 that assist in the process of placing the humeral fixation plate 100A. The plurality of discrete position sites 167 are useful when the humeral fixation plate 100A is repositioned during the use thereof, as discussed further below. The plurality of discrete position sites 167 can include a plurality of concavities 167A. The concavities 167A can include scallop disposed along the length of the slot 160A. A non-locking anchor 132 can be placed in the slot 160A (see FIGS. 2B-C).

The slot 160A also can include a visual spacing indicator 169 disposed along the slot 160A. The visual spacing indicator 169 can include one or a plurality of lines 171. The lines 171 can be formed transverse to the longitudinal axis 159. The lines 171 can extend away from the slot 160A toward a perimeter of the distal portion 116. In one embodiment, each of the lines 171 extends from a central portion of one of the concavities 167A. The lines 171 can be provided on one side of the slot 160A or on both sides of the slot 160A.

The spacing between the lines 171 can be provided to assure that repositioning of the humeral fixation plate 100A is successful. For example, the spacing between the lines 171 can assure that a K-wire 296 placed through a positioning channel 296A of the humeral fixation plate 100A will not be in a same bone location after repositioning the plate 100A as when the K-wire 296 was initially placed through the positioning channel 296A of the plate 100A.

II. Anchor Trajectory Guides and Methods

As noted above it is desired to have the polyaxial anchors 130 extend through the humerus H such that the medial ends 142 thereof extend to and are lodged in opposing cortical bone region CB. The cortical bone region CB of the head 10 of the humerus H is an outer shell of the head. It is desired that the contact surface between the medial side 112 of the fixation plate 100 and the lateral surface LS of the humerus H be bounded by a smaller area than an area bounding all of the medial ends 142 of the polyaxial anchors 130. As noted above, the polyaxial anchors 130 generally are implanted in a splayed orientation to achieve this. Because the bone of the humerus H is irregular it is not a simple task to assure that the medial ends 142 of the polyaxial anchors 130 reach the opposing cortical bone region CB through the anchor apertures 134 of the fixation plate 100 while, in some applications, at the same time achieving a high degree of splaying. Furthermore, because patients are of different sizes, a proper splayed arrangement for a large patient may result in exposed screw tips on the medial side of the humerus which could even be exposed in the articular surface. This result would be disadvantageous as potentially resulting in scoring of or otherwise damaging the articular surface of the glenoid. The anchor trajectory guide 200 helps to solve these problems.

The anchor trajectory guide 200 includes a body 204 that has a medial side 208 and lateral side 212. The medial side 208 is a first side and the lateral side 212 is a second side. The medial side 208 is configured to mate with, e.g., to be in direct contact with, the lateral side 108 of the fixation plate 100 as discussed above and further below. The lateral side 212 is exposed when the anchor trajectory guide 200 is coupled with the fixation plate 100 such that access can be provided to a plurality apertures, including a plurality of guide apertures 232, a pin aperture 236, and a fastener aperture 237 (see FIG. 4). In one embodiment a plurality of, e.g., six, guide apertures 232 are provided in a proximal portion 218 of the anchor trajectory guide 200 and a plurality of, e.g., three, guide apertures 232 are provided in a distal portion 216 of the anchor trajectory guide 200. The guide apertures 232 can extend from a first opening on the medial side 208 to a second opening on the lateral side 212.

The proximal portion 218 of the anchor trajectory guide 200 is configured to be disposed over the proximal portion 118 of the fixation plate 100 when the fixation plate 100 and the anchor trajectory guide 200 are coupled together. At least the medial side 112 and in some cases both the medial side 112 and the lateral side 108 of the proximal portion 118 are arcuate in form. The fixation plate 100 preferably has a concavity on the medial side 112 such that the convexity of the humerus H can be received in or accommodated in the proximal portion 118 of the fixation plate 100. The concavity on the medial side 112 may be generic or patient specific. The distal portion 116 of the fixation plate 100 generally extends along the neck region and distal of the neck region of the humerus H and thus has less or no concavity in the proximal-distal direction. The distal portion 116 extends from an end of the proximal portion 118.

Due to the shape of the fixation plate 100 and the configuration of the anchor trajectory guide 200 to nest in or on the fixation plate 100, the proximal portion 218 is gradually thinner in the medial-lateral direction toward the proximal terminal end of the anchor trajectory guide 200. The proximal portion 218 is gradually thinner in the medial-lateral direction toward the distal terminal end of proximal portion 218. The reduction in thickness is due to the configuration of the anchor trajectory guide 200 to accommodate the arcuate shape of the lateral side 108 of the proximal portion 118 of the fixation plate 100. The thickness of distal portion 216 of the anchor trajectory guide 200 in the medial-lateral direction is less variable. The distal portion 216 can have a generally constant thickness in the medial-lateral direction between the distal end of proximal portion 218 and the distal terminal end of the anchor trajectory guide 200.

As is discussed in greater detail below, the guide apertures 232 are arranged to provide anchorage to cortical bone portions dispersed around the head 10 of the humerus H. For example, one or more, e.g., two, superior guide apertures 232S can be provided to direct creation of probe channel PC and thereby anchor channels toward a superior portion of the head 10. A plurality of, e.g., four, central guide apertures 232C can be provided in a central portion of the proximal portion 218 of the anchor trajectory guide 200. The central guide apertures 232C can be used to form probe channel PC and thereby anchor channels for directing anchors into cortical bone regions in a central portion of the head 10. Finally, a plurality of, e.g., three, inferior guide apertures 232I can be provided to enable formation of probe channel PC and thereby anchor channels that are directed form the lateral surface LS of the humerus H to the medial calcar MC thereof.

FIG. 6 shows that the pin aperture 236 can extend from the lateral side 212 to the medial side 208 along a longitudinal axis 238. The longitudinal axis 238 preferably is non perpendicular to the lateral side 212 but rather is disposed at an acute angle to the lateral side 212. For example, an angle of between 30 and 60 degrees, e.g., about 50 degrees can be provided between a longitudinal axis 213 of the lateral side 212 and the longitudinal axis 238.

The anchor trajectory guide 200 also includes a locator 220 provided on the medial side 208 that can be used to couple the anchor trajectory guide 200 to the fixation plate 100. The locator 220 can be configured as a protrusion with a fixed end disposed at or coupled with the medial side 208 and a free end disposed away from the medial side 208. The free end of the locator 220 can be disposed medially of the medial side 208. The free end of the locator 220 can be disposed along a longitudinal axis 222 of the locator 220 that extends through the free end of the locator and that intersects the lateral side 212. The longitudinal axis 222 of the locator 220 can be disposed perpendicular to the lateral side 212 in one embodiment. The longitudinal axis 222 of the locator 220 can be disposed non-parallel to the longitudinal axis 238. An angle of between 5 degrees and about 60 degrees, e.g., about 15 degrees, about 25 degrees or about 35 degrees can be provided between the longitudinal axis 222 of the locator 220 and the longitudinal axis 238 of the pin aperture 236.

The locator 220 and the fastener aperture 237 can work together to secure the anchor trajectory guide 200 to the fixation plate 100 as discussed further below. For example, after the locator 220 is received in the locating aperture 120 a screw or other fastener can be advanced through the fastener aperture 237 and into the coupling aperture 172. The coupling aperture 172 can be threaded to engage threads of the screw. A friction or interference fit could be used to couple the anchor trajectory guide 200 to the fixation plate 100 via the fastener aperture 237 and the coupling aperture 172.

Figure 3:
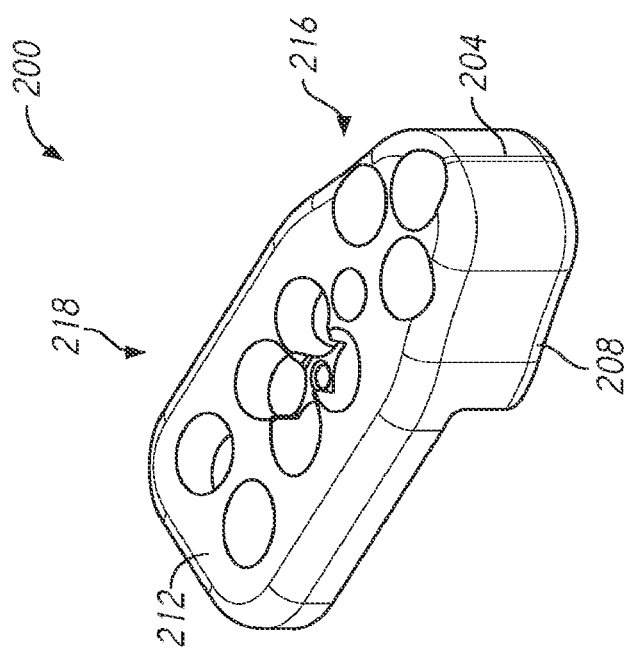
FIG. 3 is a perspective view of a lateral side of an anchor trajectory guide.
Figure 3A:
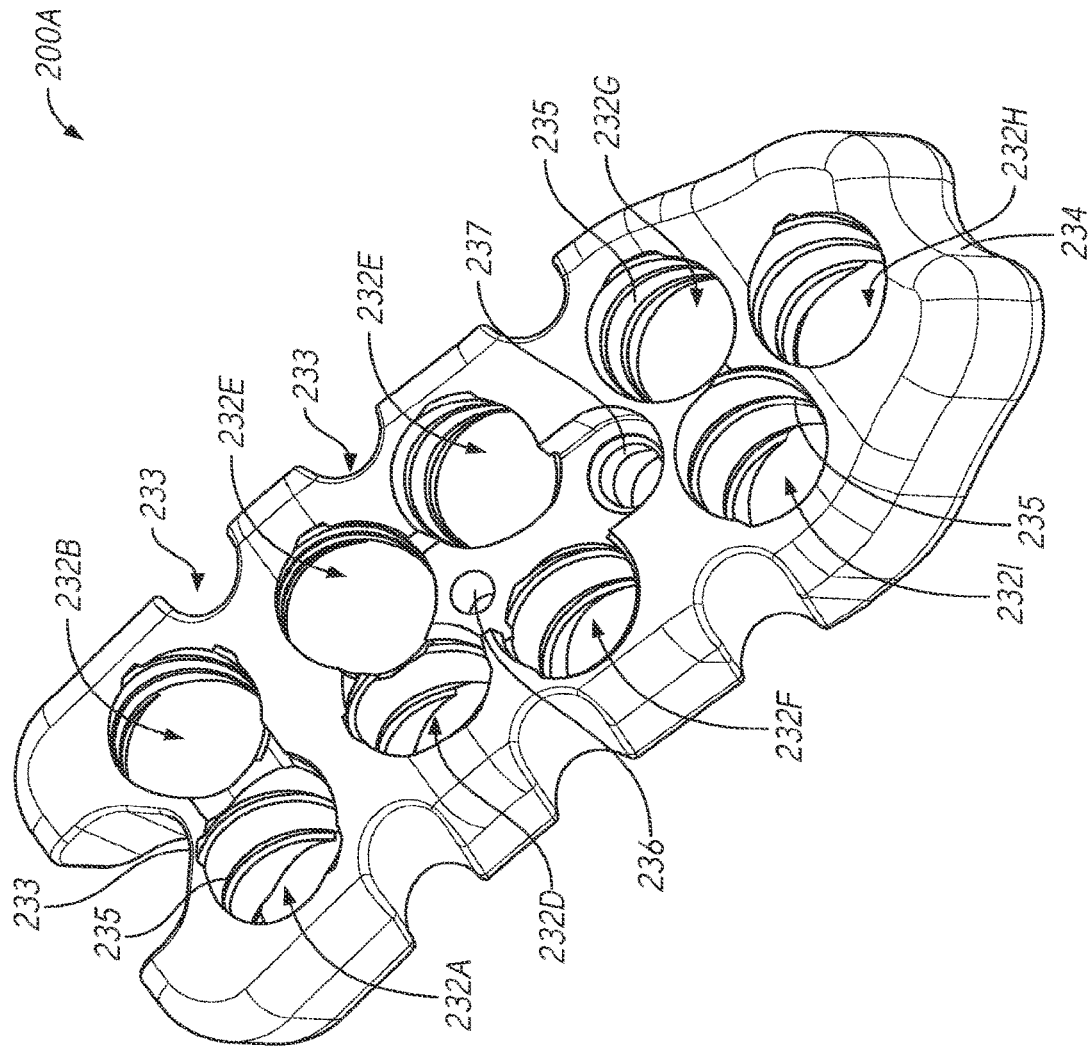
FIG. 3A is a perspective view of a lateral side of another example of an anchor trajectory guide.

FIG. 3A illustrates a anchor trajectory guide 200A that is a modified example or embodiment of the anchor trajectory guide 200. The anchor trajectory guide 200A can include any of the features of the anchor trajectory guide 200 and such descriptions will not be repeated here. Also, structurally compatible features of the anchor trajectory guide 200A can be incorporated into the anchor trajectory guide 200. The anchor trajectory guide 200A includes an perimeter along which a number of concavities are provided. The concavities include suture slots 233 that are disposed along an anterior side and a posterior side of the anchor trajectory guide 200A. In the image, the anterior side of the anchor trajectory guide 200A is generally to the left and the posterior side is generally to the right. The anchor trajectory guide 200A can also include a superior suture slot 233 disposed at a superior location of the anchor trajectory guide 200A. In one embodiment, the suture slots 233 align with the suture apertures 164 on the fixation plate 100. This allows the surgeon to perform any soft tissue or bone fragment suture anchoring to the fixation plate 100 without interference from the anchor trajectory guide 200A.

The anchor trajectory guide 200A can include the guide apertures 232 disposed in inferior, central and superior locations as discussed above in connection with the anchor trajectory guide 200. The guide apertures 232 can include an anterior superior guide aperture 232A and a posterior superior guide aperture 232B. The guide apertures 232 can include a plurality of, e.g., two, anterior central guide apertures 232D, a plurality of, e.g., two, posterior central guide apertures 232E. The guide apertures 232 can include an inferior guide aperture 232H. The inferior terminal end of the anchor trajectory guide 200 can be configured to receive a portion of another guide. For example, the anchor trajectory guide 200A can include a guide groove 234 disposed in the inferior terminal end.

One or more, e.g. all of the guide apertures 232 can include structures for mating with guide sleeves, which are discussed below. The guide apertures 232 of the anchor trajectory guide 200A can include internal threads 235 disposed through the length of the guide apertures 232. The threads 235 are configured such that the direction of advancing an anchor 130 therethrough is fixed and the threading axis is suitable for the size of the humerus being repaired. In contrast the axis of advancing the poly axial anchors 130 through the fixation plate 100 can vary. This can be made possible by any suitable structure in the polyaxial apertures 134 of the plate 100. The threads 235 can retain their configuration as the anchors 130 are being advanced therethrough. The apertures 134 can allow the anchors 130 to be advanced in a range of directions therethrough. For example, the apertures 134 can have a limited number of thread features (e.g., three or less, two or less, or just one arcuate thread) from the medial to the lateral side of the plate 100. Threads through the apertures 134 can be soft enough to allow cross-threading when the anchors 130 are advanced to modify an initial trajectory defined by the threads. The threads through the apertures 134 can comprise helical or annular arc segments that can be threaded in different directions or axes. Threads through the apertures 134 could also be eliminated by providing an inner surface of the apertures 134 that can yield as the anchor 130 is being advanced along a selected trajectory. These polyaxial apertures features can be imposed on the apertures 134 of the fixation plate 100 by the configuration of the threads 235 of the anchor trajectory guide 200 or the guide 200A or of other variants disclosed herein. The guide apertures 232 can have tapered configurations, slots, or other structures for mating with the sleeves, as discussed further below.

III. Fixation Plates, Methods, and Kits

Figure 7:
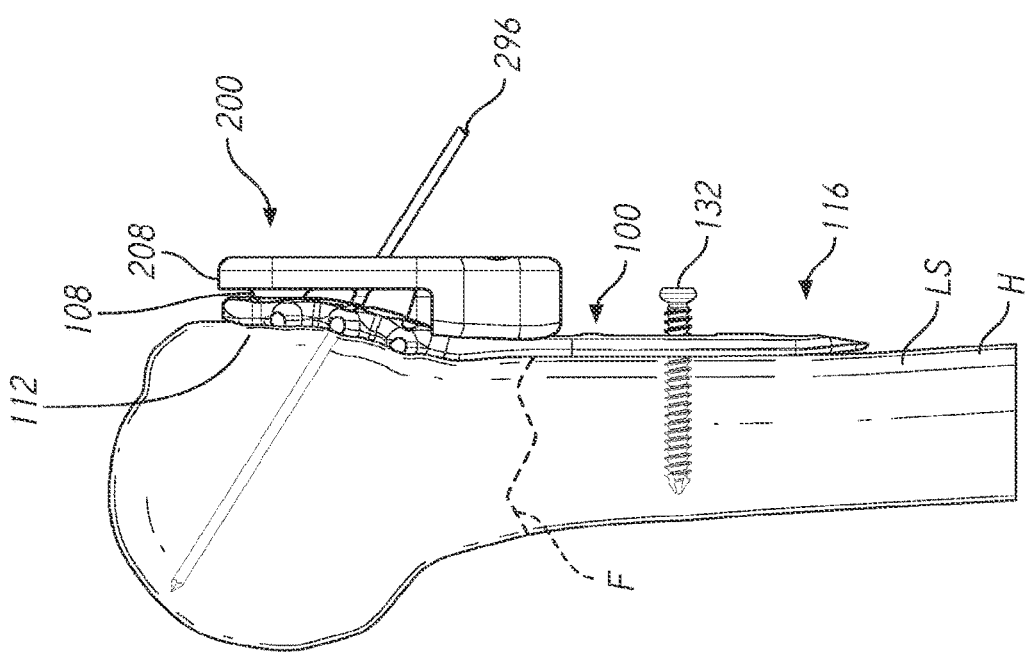
FIG. 7 is an anterior view of a humerus with a fixation plate and an anchor trajectory guide coupled thereto illustrating part of a method of connecting the fixation plate to the humerus.

FIGS. 7-26 illustrate various fixation plate methods. FIG. 7 shows that in one technique the fixation plate 100 is initially placed in contact with the lateral surface LS of the humerus H. A medial side 112 of the fixation plate 100 can be placed on the lateral surface LS of the humerus H. In so placing the fixation plate 100, the distal portion 116 can be aligned with the lateral surface LS distal of the fracture F, which will usually be distal of the neck of the humerus H. Thereafter a non-locking anchor 132 can be placed in the slot 160 (see FIG. 2) of the fixation plate 100 in the distal portion 116. The non-locking anchor 132 can be placed approximately in the center of the slot 160 or can be guided to the center (or another initial position) by a slot anchor guide assembly 239 including a slot anchor guide 240 as shown in one embodiment in FIGS. 7A-7E. The slot anchor guide assembly 239 also includes a drill sleeve 260. The drill sleeve 260 can be configured to control advancement of a drill but also can be used to couple the slot anchor guide 240 to the fixation plate 100 as discussed further below.

Figure 7A:
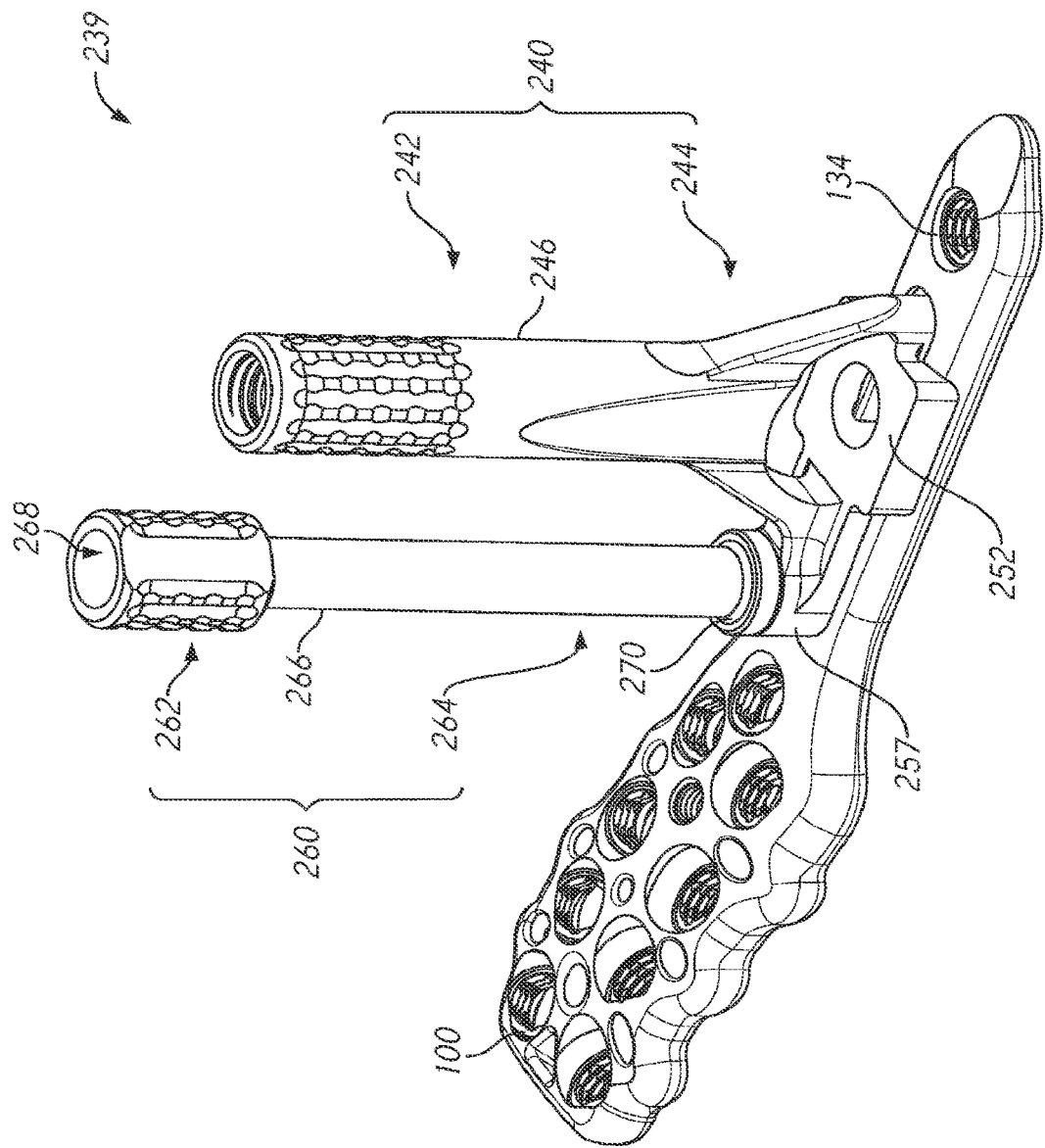
FIG. 7A is a perspective view of a slot anchor guide assembly according to one example.
Figure 7C:
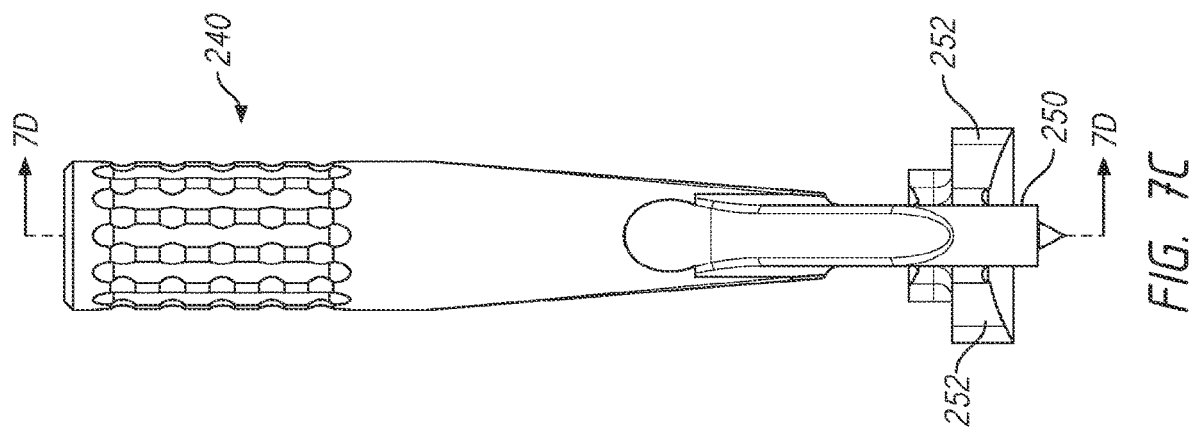
FIG. 7C is a superior or inferior side view of the slot anchor guide of FIG. 7B.
Figure 7B:
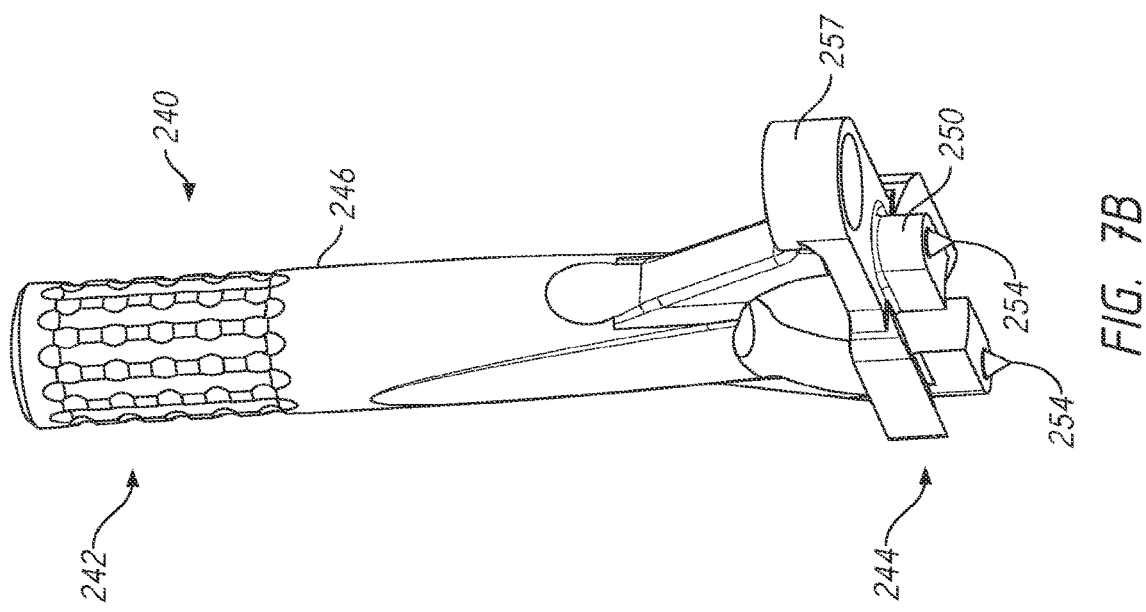
FIG. 7B is a medial side perspective view of a slot anchor guide of the slot anchor guide assembly of FIG. 7A.
Figure 7F:
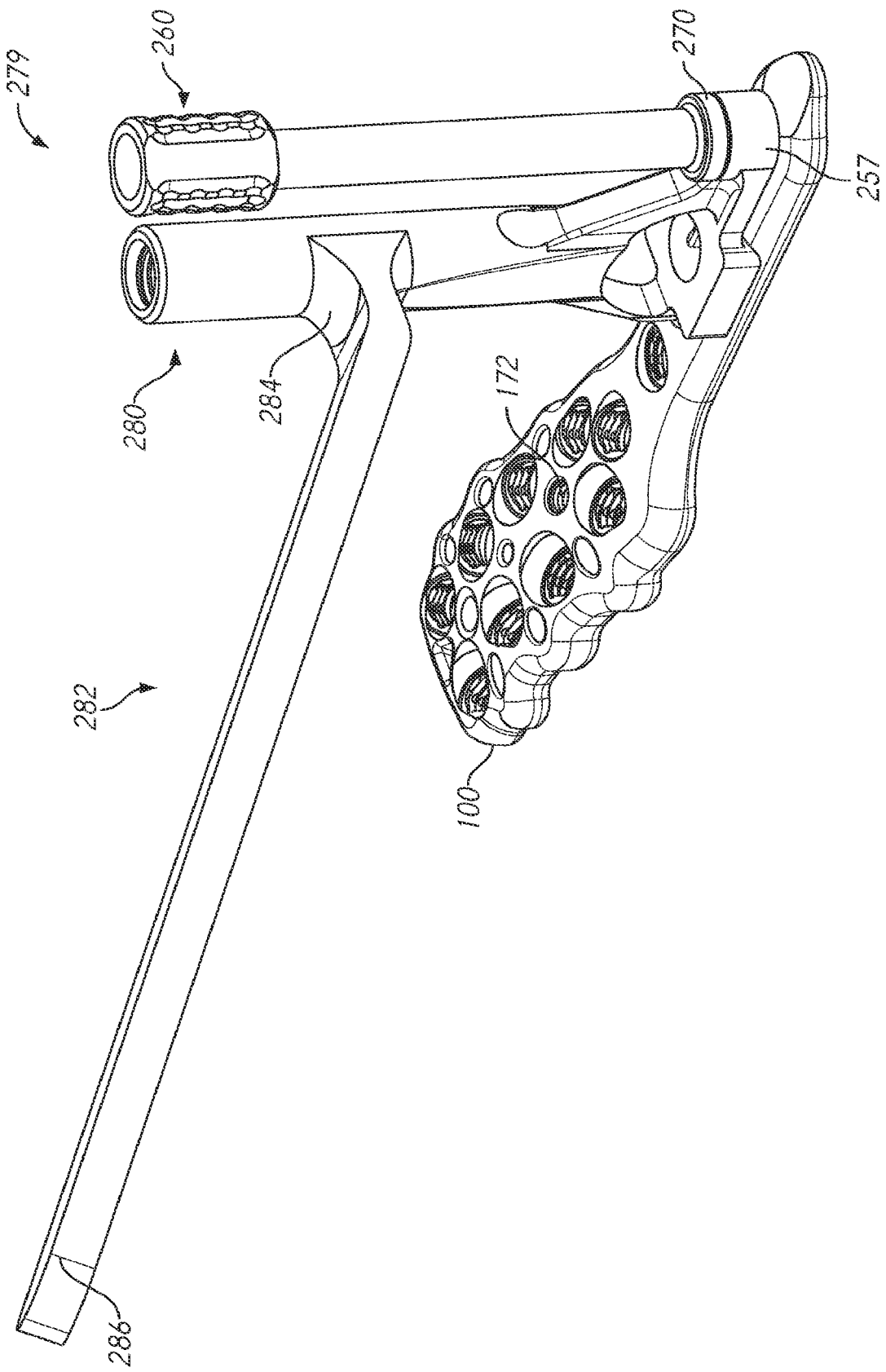
FIG. 7F is a perspective view of a slot anchor guide assembly according to another example.

The slot anchor guide 240 includes a lateral portion 242 and a medial portion 244. The lateral portion 242 is the portion that is farther away from the lateral surface LS of the humerus H when the slot anchor guide assembly 239 is coupled with the humerus. The medial portion 244 is the portion that is closer to the lateral surface IS of the humerus H when the slot anchor guide assembly 239 is coupled with the humerus. The lateral portion 242 includes an elongate cylinder 246 that projects between the terminal lateral end of the slot anchor guide 240 and the medial portion 244. The elongate cylinder 246 can be configured with a ribbed outer surface along a portion thereof to help the surgeon grasp the slot anchor guide 240. FIG. 7F shows that in another embodiment a slot anchor guide 280 can be configured with a handle 282 as discussed further below. The lateral portion 242 also can include a lumen 248 (see FIG. 7D) disposed therethrough. The lumen 248 can be accessed at a terminal lateral end of the slot anchor guide 240. The lumen 248 can extend through the lateral portion 242 adjacent to the medial portion 244.

The medial portion 244 can include a medial projection 250. The medial projection 250 can be configured to mate with the slot 160. For example, if the slot is oval shaped the medial projection 250 can have the same oval shape. The inferior-superior extent 250L of the medial projection 250 can be slightly smaller than the inferior-superior extent of the slot 160. As a result, the medial projection 250 can slip into the slot 160. The slot anchor guide 240 is coupled with the fixation plate 100 using a threaded interface of the drill sleeve 260, as discussed further below. In other embodiments the slot anchor guide 240 can be configured for positioning the fixation plate 100. The medial projection 250 can be made to have a small amount of interference fit with the slot 160 so that the fixation plate 100 can be held on the slot anchor guide 240 as the surgeon moves the slot anchor guide 240 around. This can reduce the amount of direct handling of the fixation plate 100 that is needed during the procedure.

The medial portion 244 can also include one or more anterior-posterior projections 252. The anterior-posterior projections 252 are configured to nest over the portions of the fixation plate 100 that are disposed anterior and posterior of the slot 160. Although the drill sleeve 260 can be used to engage the slot anchor guide 240 to the fixation plate 100 by a threaded interface, in one embodiment the anterior-posterior projections 252 have a smaller radius of curvature than does the slot 160 in the anterior and posterior directions on the anterior and posterior sides of the slot 160 and/or mating ridges on these surfaces can be provided for the anterior-posterior projection 252 to grip the fixation plate 100. The anterior-posterior projections 252 can flex to grip the fixation plate 100 in the area anterior and posterior of the slot 160.

The slot anchor guide 240 also can include one or more cleats 254. The cleats 254 provide for at least a temporary footing or connection to the lateral surface LS of the humerus H. The cleats 254 can be configured as short spikes that project medially of the medial projection 250. The cleats 254 can be configured to project medially of the medial side 112 of the fixation plate 100 when the slot anchor guide assembly 239 is assembled. When the combination of the fixation plate 100 and the slot anchor guide 240 are brought into initial contact with the lateral surface LS of the humerus H the cleats 254 can be pressed into the cortical bone on the lateral surface LS which will hold the fixation plate 100 in place as the surgeon holds the slot anchor guide 240.

The lumen 248 can be configured to couple with a guide sleeve, such as any of those disclosed herein. For example, the lumen 248 can have threads 249 disposed adjacent to the terminal lateral end of the lateral portion 242. When a guide sleeve is disposed in the lumen 248 and mated with the threads 249 a medial end of the sleeve can be disposed adjacent to the lateral surface IS of the humerus H to provide access for a non-locking anchor 132 advanced through the sleeve.

As discussed above, the slot anchor guide assembly 239 can be coupled together using the drill sleeve 260. The drill sleeve 260 can have a lateral portion 262, a medial portion 264, and a lumen 268 disposed through the lateral and medial portions 262, 264 through an elongate cylinder 266. The medial portion 264 can include a transverse projection 270. The transverse projection 270 can include a short cylindrical shoulder that is configured to mate with a superior-inferior projection 257. The transverse projection 270 can have a planar side that contacts a planar lateral side of the superior-inferior projection 257. FIG. 7A shows the superior-inferior projection 257 in a superior orientation relative to the fixation plate 100. As discussed above, the anchor trajectory guide 200 and the anchor trajectory guide 200A can be configured with a guide groove 234. The guide groove 234 can be configured to receive the curved free end of the superior-inferior projection 257 so that the slot anchor guide 240 and the anchor trajectory guides 200, 200A can nest together in an assembly. The slot anchor guide 240 can also be oriented 180 degrees from the orientation in FIG. 7A with the superior-inferior projection 257 aligned with and coupled to the inferior-most anchor aperture 134. In either orientation a medial end of the drill sleeve 260 can be coupled to one of the anchor aperture 134 in the fixation plate 100 by way of threads disposed on an outside surface of the drill sleeve 260. The medial end of the drill sleeve 260 can be advanced through an anchor hole 258 in the slot anchor guide 240 until threads thereon mate with threads in the anchor aperture 134. Thereafter the lateral portion 242 and/or the lateral portion 262 can be used to manipulate any or all of the slot anchor guide assembly 239.

FIG. 7F illustrate a slot anchor guide assembly 279 that is similar to the slot anchor guide assembly 239 except as described differently below. The slot anchor guide assembly 279 includes a slot anchor guide 280 and the drill sleeve 260. The slot anchor guide 280 includes a handle 282. The handle 282 has a fixed end 284 that is coupled with and extends from one side of a cylindrical body in a lateral portion of the slot anchor guide 280. The handle 282 extends longitudinally between a free end 286 and the fixed end 284. The handle 282 is configured to enable the surgeon to move the slot anchor guide 280 and thereby the fixation plate 100.

FIG. 7F shows the slot anchor guide assembly 279 coupled with the fixation plate 100 in an opposite orientation to that of FIG. 7A. The superior-inferior projection 257 of the slot anchor guide 280 is oriented inferiorly. The anchor hole 258 in the superior-inferior projection 257 is aligned with the distal or inferior-most anchor aperture 134 in the fixation plate 100. Thereafter, the drill sleeve 260 is aligned with and advanced through the superior-anchor hole 258 and into the anchor aperture 134. Threads on the medial portion 264 of the drill sleeve 260 are advanced into the threads in the anchor aperture 134 until the transverse projection 270 comes into contact with the lateral side of the superior-inferior projection 257.

Both the superior and the inferior orientations of the slot anchor guides 240, 280 allow the anchor trajectory guide 200 to be coupled with the fixation plate 100 at the same time as the guides 240, 280. The orientation of FIG. 2F advantageously provides more clearance between the inferior end of the anchor trajectory guide 200 and the slot anchor guides 240, 280.

In one method the anchor trajectory guide 200 is coupled with the fixation plate 100. For example, the medial side 208 of the anchor trajectory guide 200 can be placed up against the lateral side 108 of the fixation plate 100. The locator 220 anchor trajectory guide 200 can be aligned with the corresponding locating aperture 120 of the fixation plate 100 and inserted into the aperture. FIG. 7 shows that the profile of the medial side 208 is matched to the profile of the lateral side 108 of the fixation plate 100. As such the fixation plate 100 can nest into the concavity of the medial side 208 in the proximal portion 218 of the anchor trajectory guide 200.

Although the locator 220 holds the position of the anchor trajectory guide 200 on the fixation plate 100 a more complete coupling of the anchor trajectory guide 200 can be provided. A screw can be advanced through the fastener aperture 237 and into the coupling aperture 172 as discussed above to provide a secure connection that will persist through the procedure. In another approach, the fixation plate 100 can be secured by advancing a K-wire 296 through the pin aperture 236. Because the pin aperture 236 and the locator 220 converge toward the bone and are on diverging axes away from the bone, e.g., the longitudinal axis 222 and the longitudinal axis 238 are converging toward other another toward the bone, the anchor trajectory guide 200 is held in place relative to the fixation plate 100. The fixed position of the anchor trajectory guide 200 relative to the fixation plate 100 allows probe channel PC and corresponding anchor channels to be reliably formed in the correct locations. Prior to forming such channels, however, the location of the fixation plate 100 and the size of the anchor trajectory guide 200 can be confirmed.

Figure 2B:
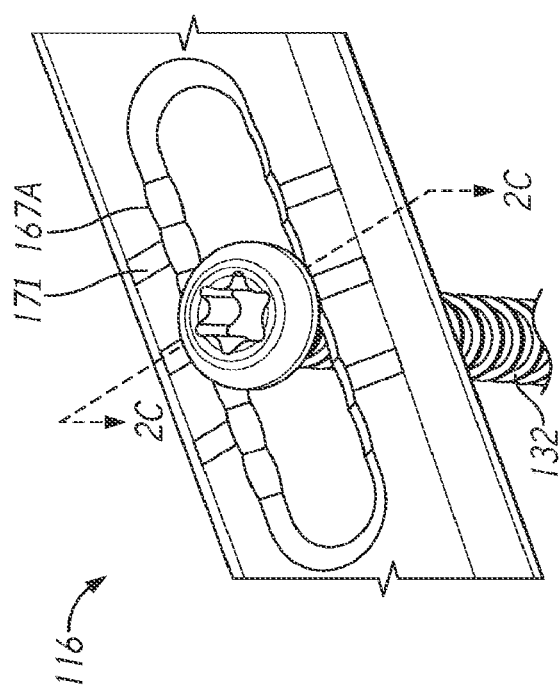
FIG. 2B show a part of a method of connecting another embodiment of a fixation plate to the proximal humerus.
Figure 4:
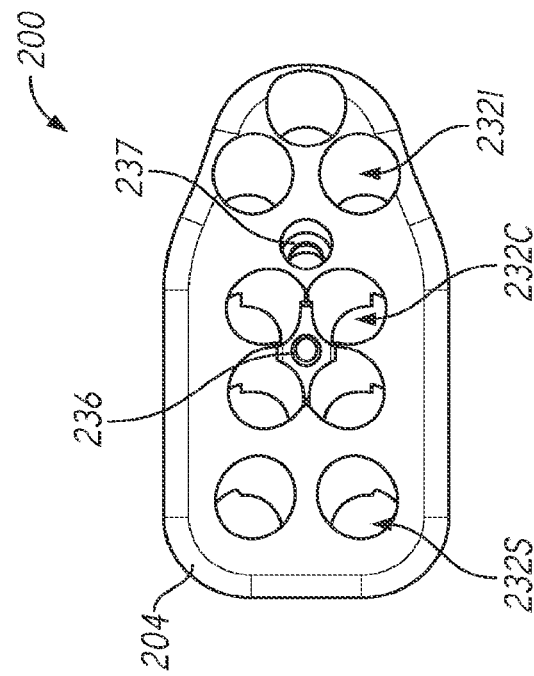
FIG. 4 is a view of a lateral side of the anchor trajectory guide of FIG. 3.
Figure 8:
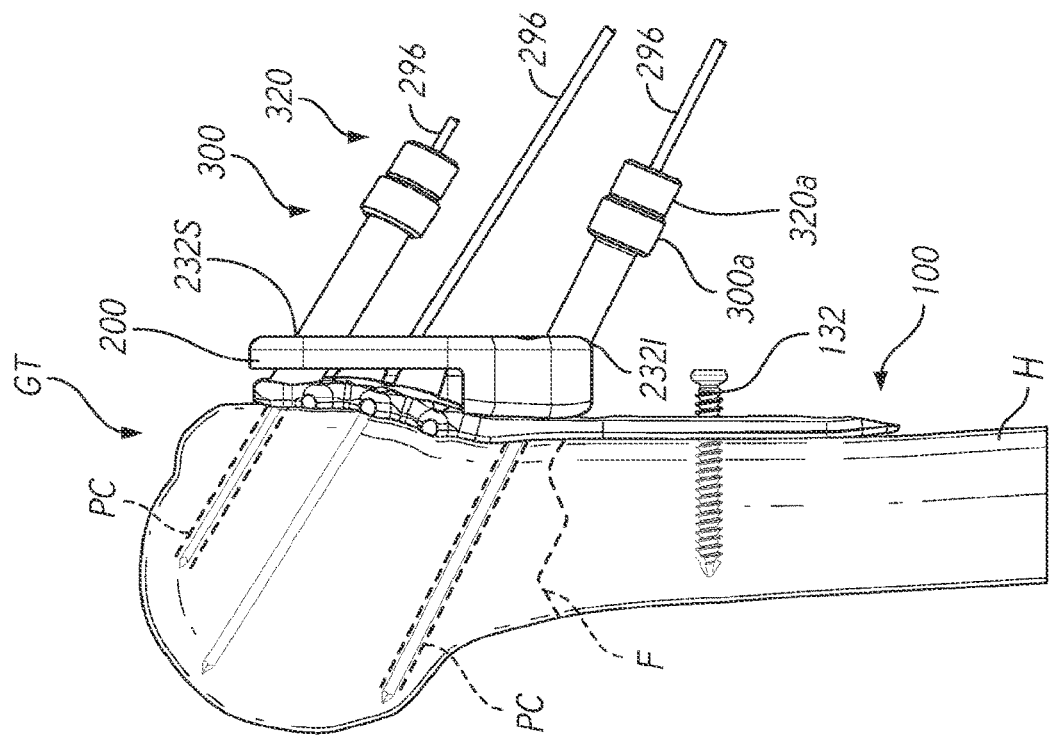
FIG. 8 shows a part of a method of connecting the fixation plate to the humerus following the part of the method illustrated in FIG. 7 in which K-wires are placed through anchor sleeves and K-wire sleeves mated with medial calcar and anterior superior access apertures.

FIG. 8 shows that once the anchor trajectory guide 200 is secured to the fixation plate 100 and the non-locking anchor 132 is advanced into the bone through the slot 160. The slot 160 advantageously allows distal-proximal motion of the fixation plate 100 after the non-locking anchor 132 is placed but before the plate is fully fixed to the humerus H. If either of the slot anchor guides 240, 280 is used to place the fixation plate 100 initially such guides 240, 280 can be removed allowing for inferior-superior adjustment of the fixation plate 100 relative to the lateral surface IS of the humerus H. The humeral fixation plate 100A facilitates a convenient method of confirming the inferior-superior position of the humeral fixation plate 100A. The K-wire 296 is advanced through an aperture in a guide 200, 200A and further through the positioning channel 296A at a first position of the non-locking anchor 132 along the slot 160A. As shown in FIG. 2B the non-locking anchor 132 can be advanced until a head portion thereof is in contact with one of the plurality of discrete position sites 167, e.g., with one of the concavities 167A. The K-wire 296 can be removed from the humerus H. The position of the humeral fixation plate 100A can be evaluated. If the position is not as desired, the non-locking anchor 132 can be retracted sufficiently to out of engagement with the discrete position site 167 in which it was initially positioned. The humeral fixation plate 100A can be shifted relative to the non-locking anchor 132 to a plurality of discrete position sites 167 proximal or distal of the initial site, e.g., to a concavity 167A proximal or distal to the initial concavity. The non-locking anchor 132 can be advanced into the concavity 167A at the new position. Then, the K-wire 296 can be advanced through the guide 200, 200A into the humerus H through the positioning channel 296A. The spacing between two adjacent concavities of the concavities 167A can be enough to assure that the K-wire 296 is not in the same position, e.g., in the channel that was formed in the humerus H in the first insertion. For example, the spacing between plurality of discrete position sites 167 can be one-half the diameter of the K-wire 296, e.g., about 1 mm in one embodiment. In other embodiment, the spacing is less or greater. For example, the spacing can be about 2 mm, about 3 mm or about 4 mm in various modified embodiments. The visual spacing indicator 169, e.g., the lines 171, can be positioned at each or at alternating concavities 167A. The spacing indicator 169. e.g., the lines 171, can be at greater intervals, e.g., every third or fourth concavity. In one method, after advancing the K-wire 296 through the aperture positioning channel 296A at a first position of the slot 160A relative to the anchor non-locking anchor 132, the K-wire is removed from the humerus H. The position of the humeral fixation plate 100A is shifted proximally or distally (e.g., inferiorly or superiorly) to a second position of the slot relative to the anchor 132. The second position is spaced from the first position by an amount greater than the one-half of or the diameter of the K-wire 296. The second position is provided by advancing the non-locking anchor 132 into a discrete position site of the plurality of discrete position sites 167 spaced along the slot 160A from the initial site of the plurality of discrete position sites 167. The slot 160A enables the non-locking anchor 132 to be retracted out to the concavities 167A without having to remove the non-locking anchor 132 from the humerus H when shifting among these and other positions that are defined along the slot 160A.

The plurality of discrete position sites 167 and the visual spacing indicator 169 enhance the usefulness of the humeral fixation plate 100A by allowing the surgeon to be certain that second and subsequent positions are spaced apart from an initial position. By providing this guidance, the surgeon can more quickly, accurately and confidently proceed through the stages of methods involving the humeral fixation plate 100A.

If the inferior-superior position is initially confirmed, K-wires can be advanced into the head 10 of the humerus H. A first K-wire 296 can be advanced toward the medial calcar MC region. Thereafter the appropriate size anchor trajectory guide 200 can be confirmed by advancing a second K-wire 296 into a superior anterior guide aperture 232S. With these K-wires 296 placed, the size of the anchor trajectory guide 200 can be confirmed. For example, if the proximal end of the anchor trajectory guide 200 is a prescribed distance, e.g., 10 mm, from a proximal aspect of the head 10 then the sire of the anchor trajectory guide 200 is appropriate. The proximal aspect from which the distance to the anchor trajectory guide 200 is measured can be the greater tuberosity OT. If the proximal end of the anchor trajectory guide 200 is less than about 10 mm from the proximal aspect of the head 10 then a smaller anchor trajectory guide 200 can be selected. If the proximal end of the anchor trajectory guide 200 is more than about 10 mm from the proximal aspect of the head 10 then a larger anchor trajectory guide 200 can be selected.

In another embodiment, the size of the head 10 of the humerus H can be estimated by providing a scale on a K-wire 296 to be inserted into the pin aperture 236 in the center of the anchor trajectory guide 200 after the non-locking anchor 132 has secured the fixation plate 100 to the humerus H. The trajectory of the K-wire 296 is aligned with the center of the articular surface of the head 10. The scale can include markings that indicate the length of the K-wire 296 inserted into pin aperture 236, across the cancellous portion of the head 10 into contact with the cortical bone region CB. From this dimension, the size of the anchor trajectory guide 200 to be used can be determined. In some cases the K-wire 296 can indicate a size (small, medium, large, etc.) of the anchor trajectory guide 200 to be used. The K-wire 296 can indicate both a dimension and a size in some embodiments.

Figure 9:
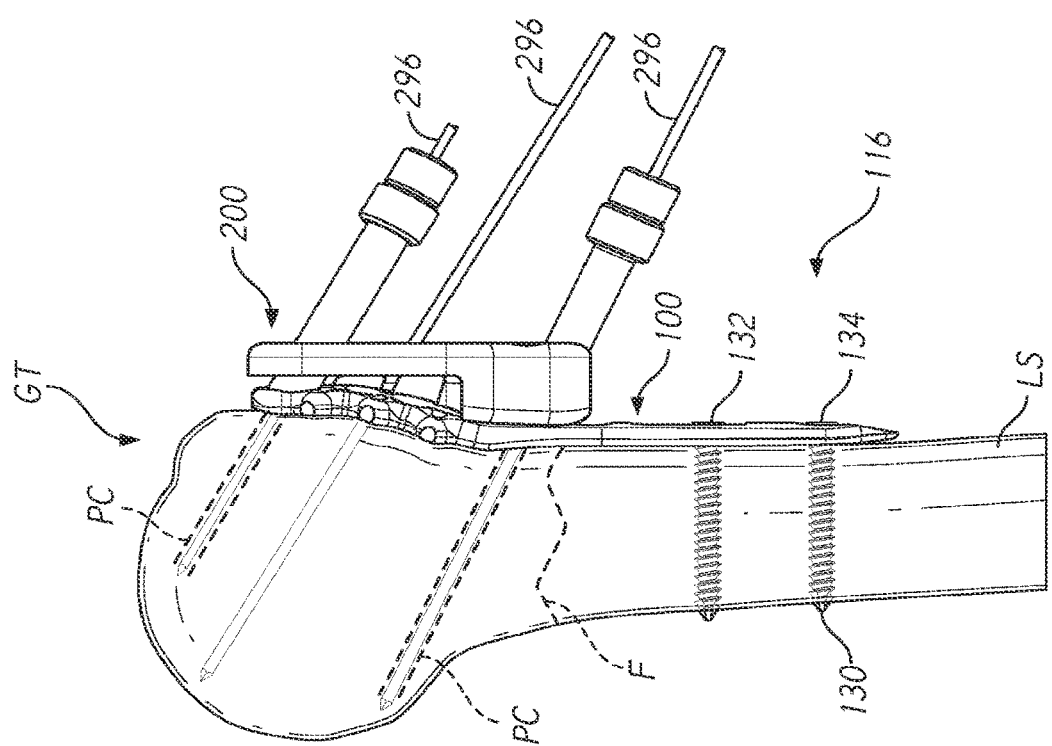
FIG. 9 shows a part of a method of connecting the fixation plate to the humerus following the part of the method illustrated in FIG. 8 in which the fixation plate and the guide are secured in a selected position.

After the size and placement of the anchor trajectory guide 200 are confirmed the fixation plate 100 can be secured to the humerus H to prevent movement therebetween. FIG. 9 shows that securing the fixation plate 100 to the humerus H can be achieved by inserting a polyaxial anchor 130 into an anchor aperture 134 in the distal portion 116 of the fixation plate 100. The method can then proceed to forming probe channels PC and thereafter to implanting anchors as discussed further below.

FIGS. 8-18 show that guide sleeves can be used in the formation of an inferior probe channel PC. A sleeve 300 can be mated to the anchor trajectory guide 200. In one technique, a medial end of the sleeve 300 can be inserted into one of the inferior guide apertures 232I and advanced from the lateral side 212 toward the medial side 208 of the anchor trajectory guide 200. The sleeve 300 can be seated in the anchor trajectory guide 200 by engaging threads on the outside surface of the sleeve 300 with internal threads in the inferior guide aperture 232I. For example, the anchor trajectory guide 200 can have, as illustrated above in FIG. 3A in connection with the anchor trajectory guide 200A, internal threads 235 disposed in an anterior inferior guide aperture 232F and in a posterior inferior guide aperture 232O that can be engaged by threads on the exterior surface of the sleeve 300. In other embodiments the sleeve 300 can be mated with a slip fit inside the inferior guide aperture 232I or any of the other guide apertures 232. Once the sleeve 300 is seated it can be an outer sleeve to receive other structures and devices. An inner sleeve 320 can be inserted into the sleeve 300. The inner sleeve 320 can be inserted by advancing a medial end of the inner sleeve 320 into a lateral end of the sleeve 300 until flanges or hubs 300a, 320a at the lateral ends of the sleeve 300 and of the inner sleeve 320 are coupled, e.g., are adjacent to or abutting each other. The inner sleeve 320 can be seated in or mated to the sleeve 300 by engaging threads on an outside surface of the inner sleeve 320 with internal thread disposed in the inside of the sleeve 300. The inner sleeve 320 can be configured to direct a K-wire 296 through the anchor trajectory guide 200 along a guide axis that is pre-defined to an axis in the humerus H to begin the formation of the probe channel PC in a desired location as shown in FIG. 8. The inner sleeve 320 can have an inner diameter that is closely matched to an outer diameter of the K-wire 296 such that the trajectory of the K-wire 296 is controlled by the location and orientation of the inferior guide aperture 232I indirectly, which controls the position and orientation of the sleeves 300,320.

After the inner sleeve 320 has been mated with the sleeve 300 and the sleeve 300 has been mated with the anchor trajectory guide 200 the K-wire 296 can be advanced into the humerus H through the cortical bone at the lateral surface IS and into the cancellous bone within the cortical bone. The trajectory of the K-wire 296 is pre-defined by the location and orientation of the mating of the fixation plate 100 with the humerus H and by the orientation of the guide apertures 232 as described above. Advancing the K-wire 296 into the humerus H defines the direction along with the probe channel PC will be formed.

FIG. 8 also shows a K-wire 296 can be inserted into a superior portion of the head 10 of the humerus H through the superior guide apertures 232S. Inserting the K-wire 296 through the superior guide apertures 232S can include mating sleeve 300 with the superior guide apertures 232S and inserting the inner sleeve 320 into the sleeve 300. For example, the anchor trajectory guide 200 can have, as illustrated above in FIG. 3A in connection with the anchor trajectory guide 200A, internal threads 235 disposed in an anterior superior guide aperture 232A and a posterior superior guide aperture 232B that can be engaged by threads on the exterior surface of the sleeve 300. As noted above the position of the fixation plate 100 and the anchor trajectory guide 200 are confirmed following insertion of the inferior and superior guide apertures. If the position is confirmed insertion of the K-wires 296 through the superior guide apertures 232S defines the trajectory of the probe channel PC to be formed later the procedure.

FIG. 9 shows that in some techniques the fixation plate 100 is secured to the humerus H by inserting the polyaxial anchor 130 through the fixation plate 100 as discussed above. The distal portion 116 can include a polyaxial aperture 134 disposed distally of the slot 160. The polyaxial aperture 104 at this location is advantageous for providing enhanced security of the fixation plate 100 because it is farthest from the proximal portion 118 through which one or a plurality, e.g., two as illustrated in FIG. 9, K-wires 296 can be advanced. FIGS. 2 and 9 shows a configuration in which the non-locking anchor 132 is fully advanced in the slot 160 (See FIG. 2) and the polyaxial anchor 130 is fully advanced into the distal polyaxial aperture 134 to immobilize the fixation plate 100 against the lateral surface LS of the humerus H.

Figure 10:
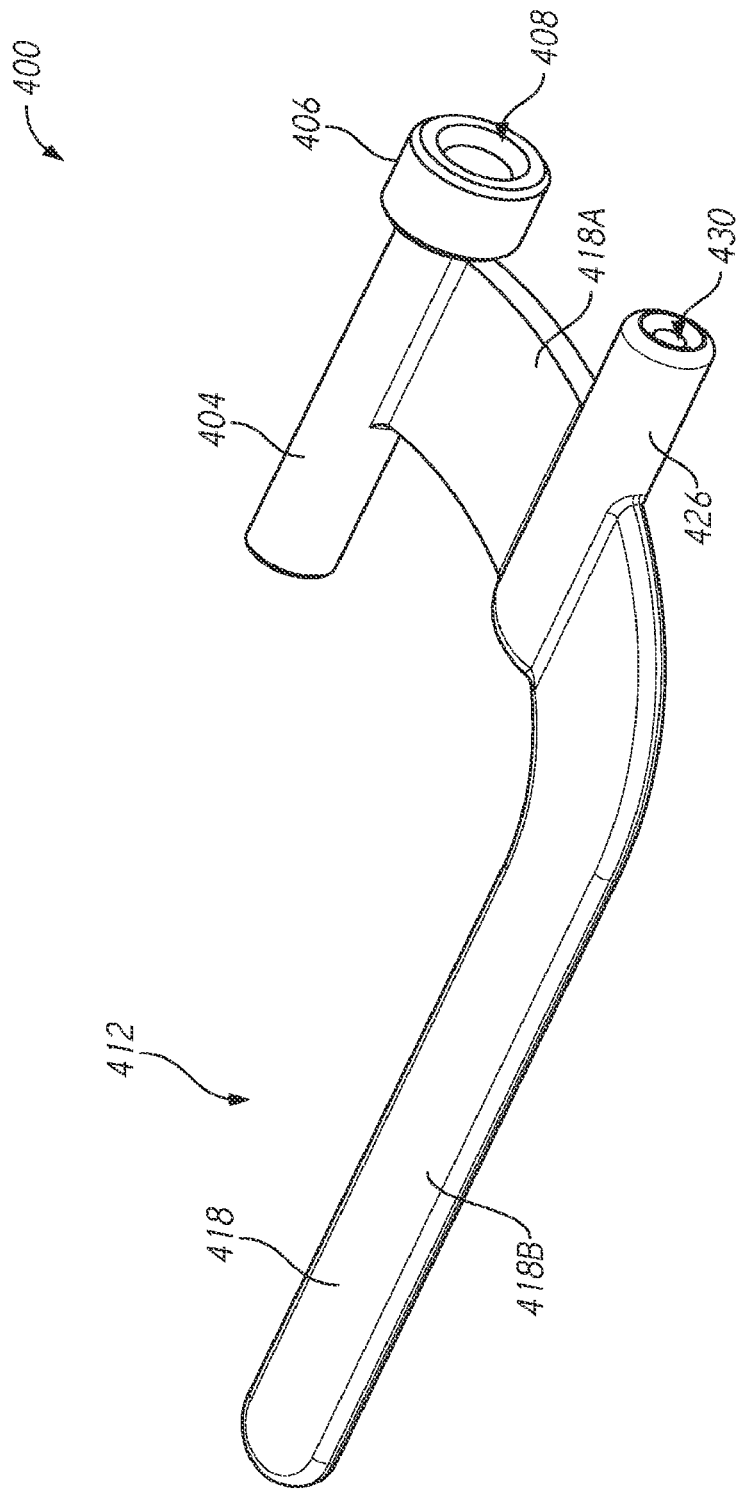
FIG. 10 is a perspective view of one example of a medial calcar guide.

FIGS. 10-16A illustrate additional approaches to orient the anchor trajectory guide 200 and the fixation plate 100 on the humerus H. FIG. 10 shows an anatomical alignment guide 400 that can be mated to the anchor trajectory guide 200. The anatomical alignment guide 400 can include a sleeve 404 that is configured to mate with one of the guide apertures 232, e.g., one of the inferior guide apertures 232L. The sleeve 404 includes a lumen 408 that extends from a lateral side of the sleeve 404, e.g., from a flange or hub 406, to a medial side thereof. The lumen 408 is configured to slideably receive a K-wire 296 as discussed below. The anatomical alignment guide 400 also includes a visual alignment member 412 disposed away from the sleeve 404. The visual alignment member 412 can include an arcuate member 418 that is coupled at a first end with a lateral end of the sleeve 404. The arcuate member 418 can extend in a first portion 418A away from the sleeve 404, e.g., in a direction substantially perpendicular to the orientation of the lumen 408. The first portion 418A can extend sufficiently from the sleeve 404 to provide clearance between the head 10 of the humerus H and a second portion 418B of the arcuate member 418 that extends from the first portion 418B when the anchor trajectory guide 200 is coupled with the fixation plate 100 and thereby with the lateral surface LS of the humerus H. The second portion 418B can be substantially parallel to the sleeve 404 in one embodiment. The arcuate member 418 is configured in the second portion 418B to extend sufficiently to be positioned or aligned with, e.g., in front of, pre-defined anatomy to which the K-wire 296 disposed through the sleeve 404 is to be aligned. As discussed further below, the arcuate member 418 is configured to extend away from the sleeve 404 to a position in front of (either on the anterior or posterior side of the humerus H) so as to be between the surgeon's eye and the an anatomical landmark. Thus the arcuate member 418 can provide a visual alignment device for visually aligning the anatomical alignment guide 400 with the landmark. When so aligned the surgeon knows that a K-wire 296 placed through the lumen 408 and through the inferior guide apertures 232I extends in a direction toward the landmark, e.g., toward the medial calcar. FIGS. 13-16A illustrate this method with the anatomic alignment guide 400 and with an anatomic alignment guide 400A discussed further below. The guide 400A is similar to the guide 400 except as described differently below.

In the flow of the methods discussed above, FIGS. 13 and 14 are alterative techniques to that shown in FIGS. 7-9. FIG. 13 shows the fixation plate 100 mated with the lateral surface LS of the humerus H. The anchor trajectory guide 200A is mated with the lateral side 108 of the fixation plate 100. The anchor trajectory guide 200 could be used, as is illustrated in some of the figures. One K-wire 296 is placed through the pin aperture 236 into the head 10 of the humerus H. The anatomical alignment guide 400A is mated with the anchor trajectory guide 200A. For example, the sleeve 404 can be inserted into the inferior guide aperture 232H. In one example, the connection between the sleeve 404 and the inferior guide aperture 232H can be a slip fit, although other connections are possible as well. The fixation plate 100 can be mated to the humerus H by the non-locking anchor 132 inserted into the slot 160, which permits the fixation plate 100 to be moved proximally and distally on the humerus H. The movement of the fixation plate 100 can be until the anatomical alignment guide 400A is aligned with a pre-defined anatomical landmark, such as the medial calcar MC. Aligning the anatomical alignment guide 400A with the medial calcar MC can include viewing the anterior surface of the head 10 of the humerus H head on and moving the assembled fixation plate 100, anchor trajectory guide 200A, and anatomical alignment guide 400 proximally or distally until the second portion 418B of the arcuate member 418 is aligned with the medial calcar MC. In the case of the guide 400A, the guide 400A can be moved proximally and distally until a K-wire 422 is aligned to the medial calcar MC Following alignment of the arcuate member 418 or the K-wire 422 with the medial calcar MC one or both of the K-wires 296 can be placed through the anchor trajectory guide 200 or the guide 200A. A superior K-wire 296 can be placed through the pin aperture 236 in the anchor trajectory guide 200 or the guide 200A. An inferior K-wire 296 can be placed through the inferior guide aperture 232I to which the anatomical alignment guide 400 or the guide 400A is mated. The K-wire 296 can be inserted through the sleeve 404 or through the inner sleeve 320 disposed in the sleeve 404. As illustrated above in FIG. 3A the anchor trajectory guide 200A shows that anterior inferior guide aperture 232F and the posterior inferior guide aperture 232O have internal threads 235 disposed therein that can be engaged by threads on the exterior surface of the inner sleeve 320. In some embodiments, the size of the anchor trajectory guide 200 or the guide 200A is confirmed by measuring a distance from a proximal landmark such as the greater tuberosity to the proximal edge of the anchor trajectory guide 200 or the guide 200A. A distance of about 10 mm indicates proper sizing of the anchor trajectory guide 200 or the guide 200A. A smaller distance between the proximal landmark and the proximal edge of the anchor trajectory guide 200 or the guide 200A suggests a smaller humerus for which a smaller anchor trajectory guide 200 or guide 200A is appropriate. A larger distance between the proximal landmark and the proximal edge of the anchor trajectory guide 200 or the guide 200A suggests a larger humerus for which a larger anchor trajectory guide 200 or guide 200A is appropriate.

Other methods of sizing the anchor trajectory guide 200 or guide 200A can include placing K-wires 296 in an inferior guide aperture 232I and in a superior guide aperture 232S. When the K-wire 296 is properly placed using the anatomical alignment guide 400 or the guide 400A, e.g., extending to the medial calcar MC the position of the K-wire 296 in the inferior guide aperture 232I can be confirmed to not be too far proximally suggesting that the anchor trajectory guide 200 or the guide 200A is too large and not too far distally suggesting that the anchor trajectory guide 200 or the guide 200A is too small. As noted above, the size of the humerus H can also be assessed by the depth into the head 10 that a K-wire 296 inserted into the pin aperture 236 extends. Other methods for sizing the anchor trajectory guide 200 or guide 200A can include measuring an external dimension of the head 10 of the humerus H or analyzing imaging data (pre-operative or intra-operative).

Figure 16:
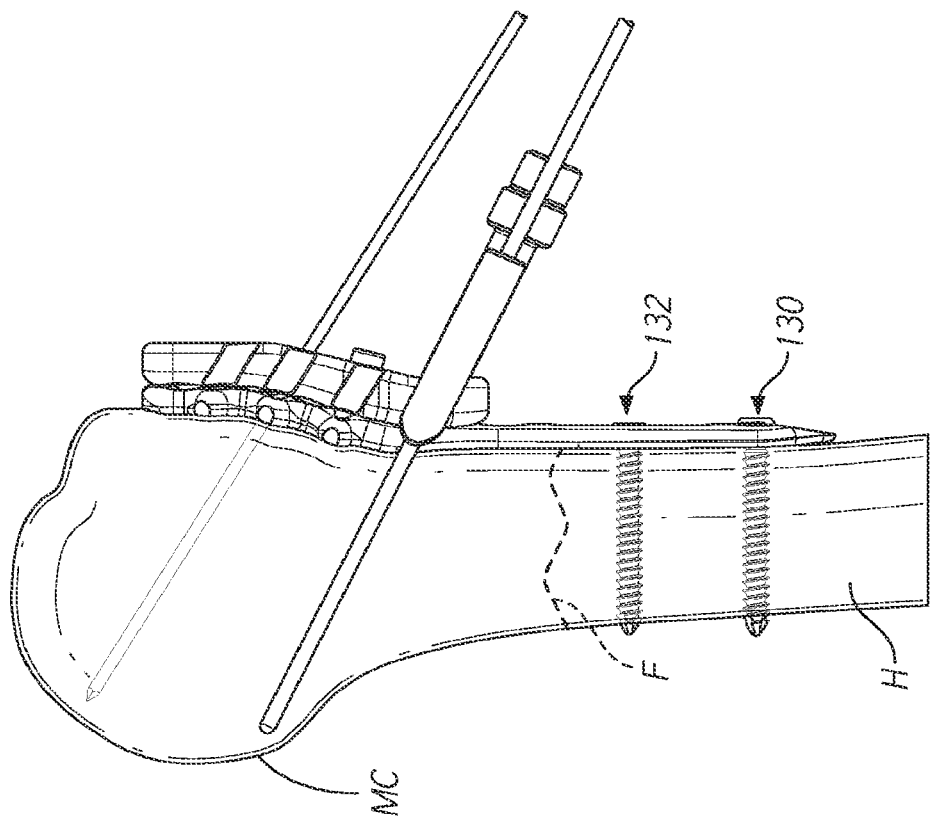
FIGS. 15, 16, and 16A show a part of a method of connecting the fixation plate to the humerus following the part of the method illustrated in FIGS. 13 and 14, the fixation plate and the guide are secured in a selected position and in which access is provided for an anchor to be advanced to the humerus through the medial calcar guide.
Figure 15:
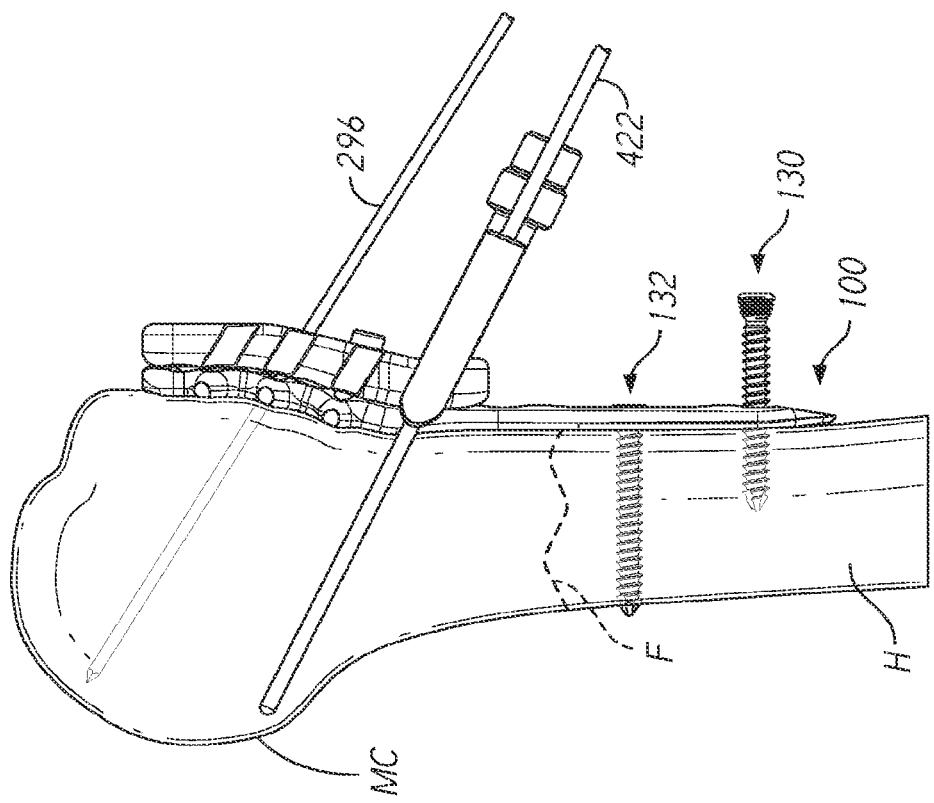
Figure 16A:
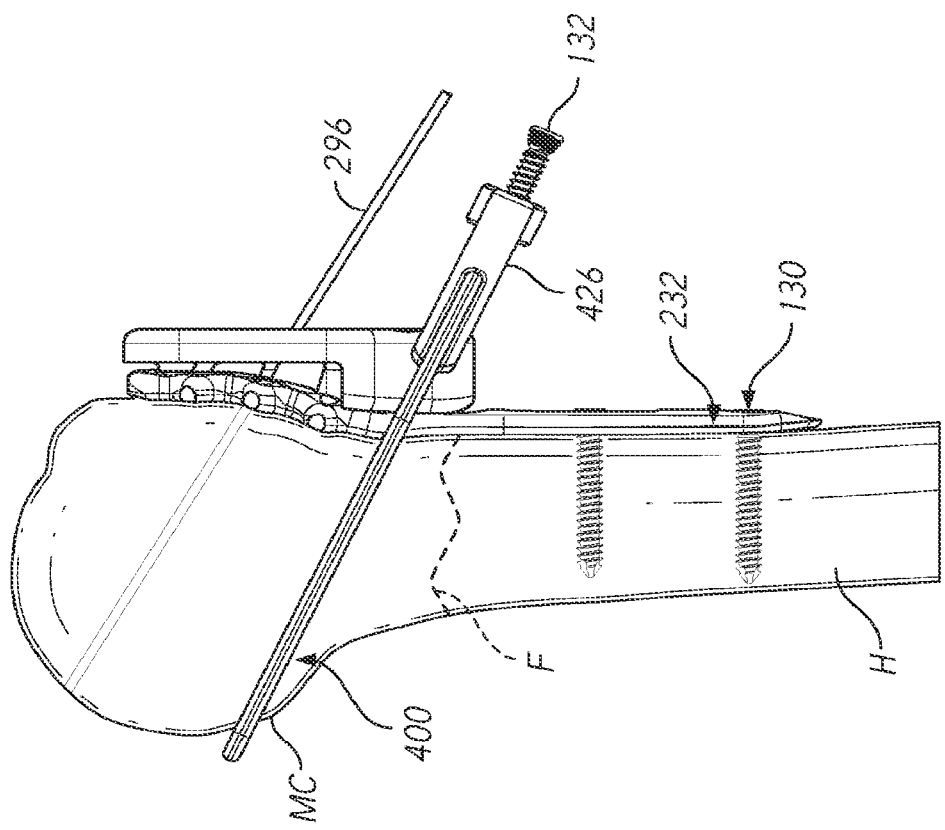

FIG. 16 shows an alternate method in which after the K-wires 296 have been placed a polyaxial anchor 130 can be advanced through the fixation plate 100 through the guide aperture 232 disposed in the distal portion 216 of the anchor trajectory guide 200 or guide 200A. The combination of the polyaxial anchor 130 and the non-locking anchor 132 in the slot 160 secures the fixation plate 100 to the lateral surface LS of the humerus H. This provides a fully secure position for the remaining portions of the procedure. After the fixation plate 100 is fixed to the lateral surface LS distal of the fracture F, a first polyaxial anchor 130 can be secured to the head 10 of the humerus H through the anatomical alignment guide 400 as shown in FIG. 16A or through the guide 400A. Placing the polyaxial anchor 130 through the anatomical alignment guide 400 or the guide 400A can be directly into the small channel formed by the K-wire 296 or can be following further bone preparation discussed below. If a polyaxial anchor 130 is placed through the anatomical alignment guide 400 or the guide 400A, following such placement the anatomical alignment guide 400 or guide 400A can be removed from the anchor trajectory guide 200 or the guide 200A.

FIGS. 10 and 16A show that one variation of the anatomical alignment guide 400 provides a secondary sleeve 426 in addition to the arcuate member 418. The secondary sleeve 426 is disposed between the sleeve 404 and the arcuate member 418. Like the arcuate member 418, the secondary sleeve 426 is disposed anteriorly of the anterior face of the humerus H when the sleeve 404 is mated with the inferior guide aperture 232L In being so placed, the secondary sleeve 426 can receive a K-wire 296 which can slide medially until the K-wire 296 is in front of a relevant landmark, e.g., the medial calcar. The secondary sleeve 426 can be used when the arcuate member 418 is not in a good position for visualizing the landmark of interest. In some variations, the secondary sleeve 426 and the arcuate member 418 extend along planes or longitudinal axes that are not aligned. This enables the arcuate member 418 to be configured to visually align with one anatomical landmark, e.g., the medial calcar MC, and the secondary sleeve 426 to be configured to visually align with a different anatomical landmark.

FIGS. 11 and 12 illustrate the anatomical alignment guide 400A in more detail. The anatomical alignment guide 400A is a streamlined form of visual alignment aid. The anatomical alignment guide 400A has a sleeve 404 as is described above. Coupled with and disposed to the side of the sleeve 404 is a secondary sleeve 426. The secondary sleeve 426 is located at a free end of a transverse projection 428 of the anatomical alignment guide 400A. The transverse projection 428 can have a first end couple with the sleeve 404 and a second end disposed away from the sleeve 404 and coupled with the secondary sleeve 426. The secondary sleeve 426 can be disposed to the side of (and in use generally anteriorly of) the sleeve 404 and at the end of the free end of the transverse projection 428. FIG. 12 shows that the secondary sleeve 426 of the anatomical alignment guide 400A is disposed entirely to the side of the medial side 208 of the anchor trajectory guide 200. This allows the secondary sleeve 426 to be medial of the fixation plate 100 and of the lateral surface LS of the humerus H when applied to the patient. This allows the anatomical alignment guide 400A to be out of the field of view of the head 10 of the humerus H during portions of the method, as illustrated by FIG. 13. The anatomical alignment guide 400A is thus lower profile than the anatomical alignment guide 400 so that the anatomical alignment guide 400A is less obstructive when mated with the lateral surface IS of the humerus H by way of the anchor trajectory guide 200 and the fixation plate 100.

The secondary sleeve 426 of the anatomical alignment guide 400A is configured to be coupled with a wire 422. The wire 422 can be inserted through a lumen in the secondary sleeve 426. Preferably the transverse projection 428 is long enough that when the sleeve 404 is mated with the inferior guide apertures 232I the wire 422 can be inserted through the secondary sleeve 426 at a location spaced anterior of an anterior side or posterior of a posterior side of the head 10 of the humerus H. Thus, the wire 422 can be advanced through the secondary sleeve 426 without entering the humerus H but rather being disposed away from and alongside the bone.

In use, the wire 422 can be inserted into the secondary sleeve 426 along-side the head 10 of the humerus H, as shown in FIGS. 13-16. The fixation plate 100 and the anchor trajectory guide 200 can be aligned to the bone (e.g., by sliding slot 160 along the non-locking anchor 132) until the wire 422 is aligned with a selected anatomical landmark or locations, such as with the medial calcar MC (see FIGS. 13-16). The transverse projection 428 is configured such that the sleeve 404 and the secondary sleeve 426 are aligned and the longitudinal axes of the lumens formed therethrough also are aligned. As such, the K-wire 296 can be inserted into the sleeve 404 and into the lateral surface LS of the humerus H with confidence that the K-wire 296 will be directed to the medial calcar MC when the wire 422 is directed along the side of the head 10 of the humerus H toward the medial calcar MC.

The anatomical alignment guide 400A also provides a simple visual confirmation at least on the anterior side thereof. A lateral length of the wire 422 should cover up and prevent a viewer from seeing a lateral length of the K-wire 296 disposed through the lumen 408 of the sleeve 404 when the alignment of the fixation plate 100 and anchor trajectory guide 200A or 200 is proper, as seen in comparing FIGS. 13 and 14. In other words, a viewer seeing the wire 422 head-on should only see one wire and should not see the K-wire 296 disposed immediately posterior or behind the wire 422.

The anatomical alignment guides 400, 400A provide convenient way to confirm the fixation plate 100 is properly aligned to the lateral surface LS of the humerus H can be fully secured by inserting the polyaxial anchor 130 into the distal guide aperture 232.

Figure 17A:
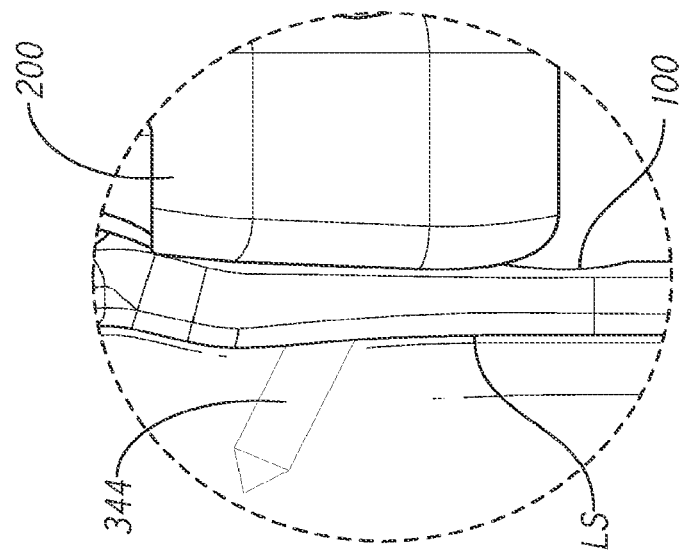
FIGS. 17 and 17A show a part of a method of connecting the fixation plate to the humerus following the parts of the method illustrated in FIGS. 9 and 13 in which an access opening is formed through the lateral cortex of the humerus.
Figure 17:
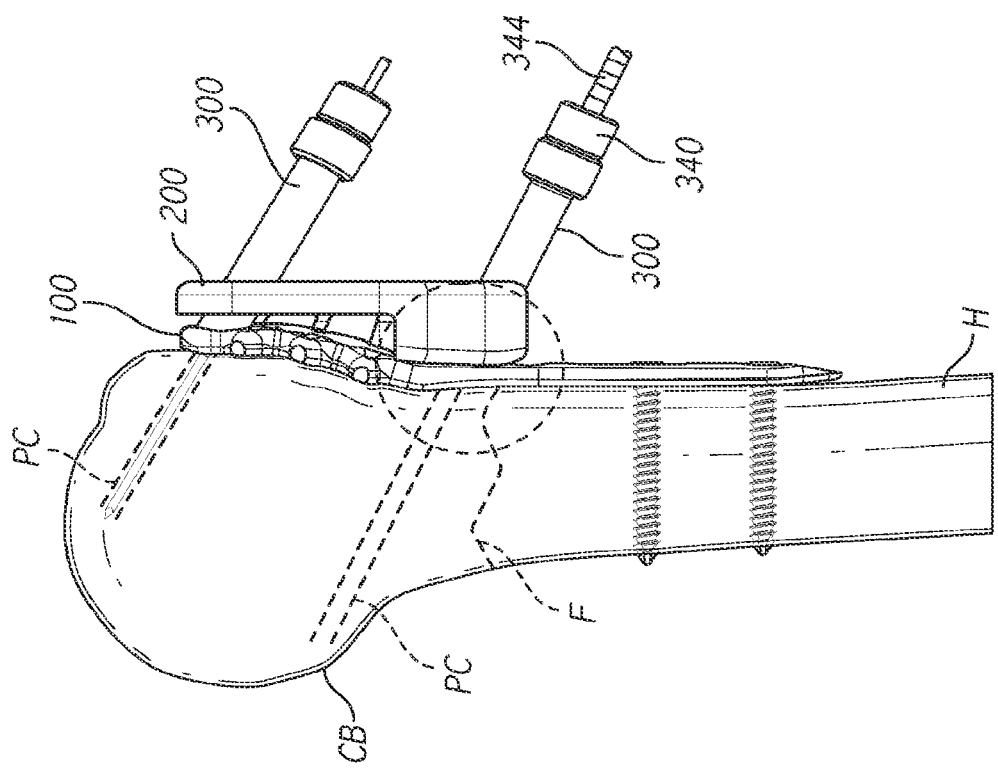

FIGS. 17 and 17A show a portion of a method that can follow any of the alignment techniques discussed above to form the probe channels PC through the properly sized anchor trajectory guide 200 or guide 200A. In one step, the inner sleeve 320 disposed in the inferior guide aperture 232I can be exchanged for an inner sleeve 340 that is configured to receive a drill hit 344. In some cases, the drill hit 344 can be configured with the same diameter as the K-wire 296 so this exchange is not necessary in all cases. In many circumstances, the drill hit 344 has a larger diameter than the diameter of the K-wire 296. In some instances, the drill bit 344 can be directly inserted into the sleeve 300 such that the inner sleeve 320 configured for the K-wire 296 can simply be removed and the drill bit 344 can be advanced directly through the sleeve 300. Where the inner sleeve 340 configured for the drill bit 344 is need, the inner sleeve 340 can be advanced such that the medial end thereof is advanced into an aperture at the lateral end of the sleeve 300. The inner sleeve 340 can be docked with the sleeve 300 in any suitable manner, e.g., using a threaded connection, slip fit or friction fit. Thereafter, the drill bit 344 can be advanced into the humerus H through the lateral surface LS thereof as shown in FIG. 17A. The drill bit 344 can have a smooth and tapered tip that can be configured to initially enter the lateral surface LS enlarging the hole therethrough formed by the K-wire 296. A length of the drill bit 344 between the tapered tip and the opposite end of the drill bit 344 can be threaded to enlarge the small passage formed by the K-wire 296 between the lateral surface LS and the cortical bone region CB opposite the lateral surface LS on the medial side of the head 10 in some techniques. In other embodiments the drill bit 344 is used to enlarge the opening through the lateral surface IS of the humerus H but not to enlarge the passage formed by the K-wire 296 all the way to the cortical bone region CB.

Figure 19:
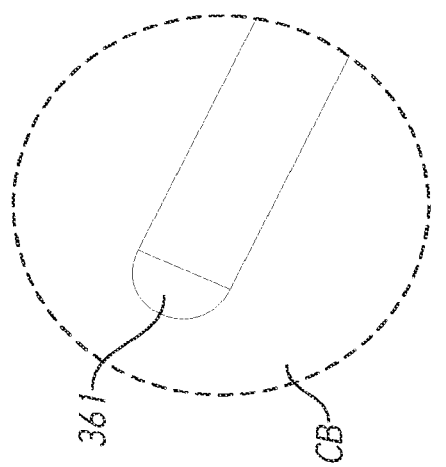
FIGS. 18-19 show a part of a method of connecting the fixation plate to the humerus following the part of the method illustrated in FIGS. 17 and 17A in which an anchor length is determined through the lateral cortex access opening.
Figure 18:
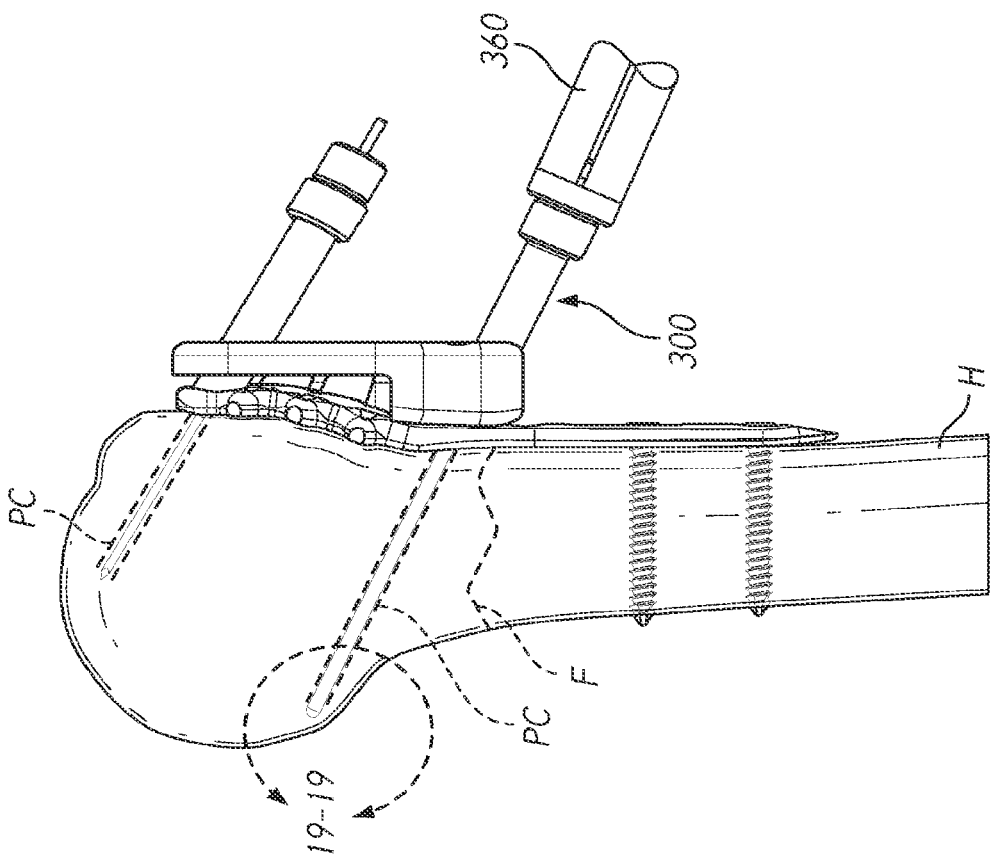

FIGS. 18 and 19 show that after the drill bit 344 is removed the inner sleeve 340 can be exchanged for a probe 360. The probe 360 can be configured to perform multiple functions. The probe 360 can provides a basis for choosing an appropriate polyaxial anchor 130 from a plurality of anchors, e.g., for choosing the polyaxial anchor 130 that has a length that will result in a medial portion of the polyaxial anchor 130 being embedded in the cortical bone region CB and a lateral portion of the polyaxial anchor 130 engaging one of the locating apertures 120 of the fixation plate 100. FIG. 18 shows that the probe 360 can be inserted into the lateral end of the sleeve 300 and the probe 360 can dock with the sleeve 300. When the probe 360 is docked with the sleeve 300, an inner member of the probe 360 can be inserted all the way across the head 10 to the cortical bone region CB. At that point, the indicia 362 at the lateral end of the probe 360 indicate which of the polyaxial anchor 130 is suitable for the particular locating aperture 120.

Another function of the probe 360 can be to enlarge the channel formed by the K-wire 296 from the lateral surface LS of the humerus H to the cortical bone region CB to fully form the probe channel PC. FIG. 19 shows that a blunt tip 361 can be provided that is well suited for pushing through the cancellous hone matter within the head 10 of the humerus H to formed the probe channel PC. The blunt tip 361 preferably is rounded to displace but not attach to tissue that is engaged thereby.

Figure 20:
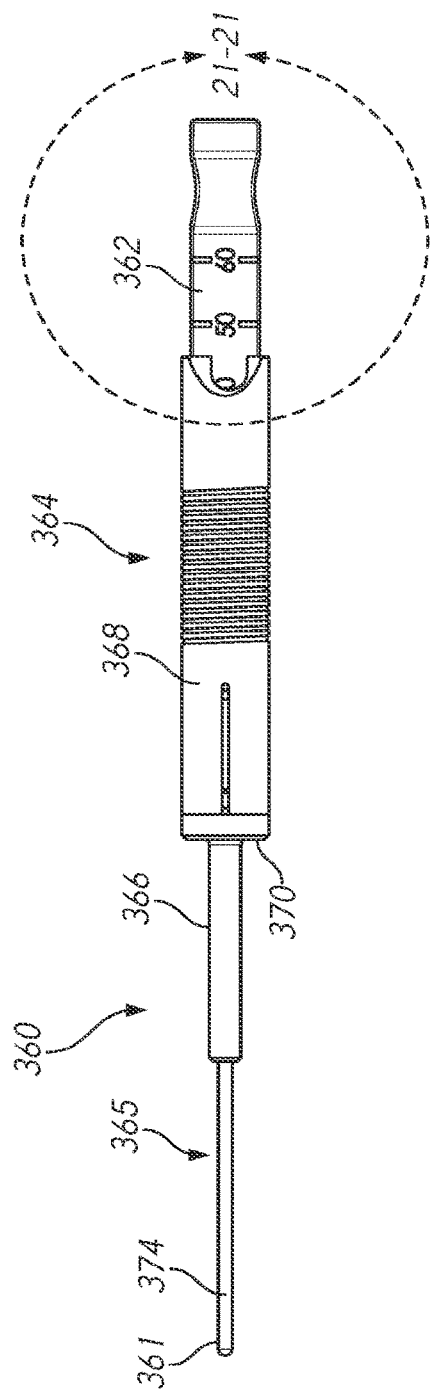
FIG. 20 shows an example of a humeral anchor length gauge that can be used to determine an anchor length in the method part illustrated in FIGS. 18-19.
Figure 21:
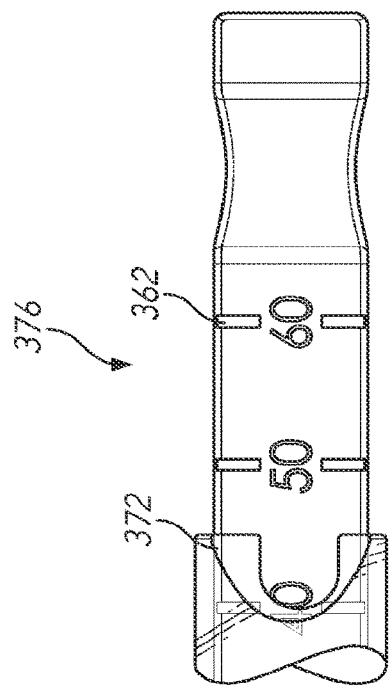
FIG. 21 illustrates one example of visual indicia that can be provided at the segment 21-21 shown in FIG. 20 to determine an anchor length in the method part illustrated in FIGS. 18-19.

FIGS. 20-21 show one embodiment of the probe 360 in more detail. The probe 360 includes an outer member 364 and an inner member 365. The outer member 364 includes a medial portion 366 and a lateral portion 368. The medial portion 366 includes a slender cylindrical portion with a lumen formed therein. The lateral portion 368 includes an outer surface that can have ribs for gripping by the surgeon and an inner lumen formed therein. A shoulder 370 can be formed between the medial portion 366 and the lateral portion 368. The shoulder 370 can be used in docking the probe 360 to the sleeve 300. For example, the probe 360 can be inserted into the sleeve 300 until the shoulder 370 abuts a lateral surface of the probe 360. The lateral portion 368 can have an aperture 372 at a lateral end thereof.

The inner member 365 can have a cylindrical medial portion 374 and a graduated lateral portion 376. The cylindrical medial portion 374 can be configured to slide within the lumen of the medial portion 366. The cylindrical medial portion 374 can be rigid to push cancellous matter aside to form the probe channel PC in some embodiments and can be configured with the blunt (e.g. rounded) tip 361 that can be atraumatic (e.g., configured not to hook or otherwise attach to bone matter). The tip 361 is configured to be inserted into the bone to enlarge the channel formed by the K-wire 296 to form the probe channel PC. When the tip 361 contacts the cortical bone region CB opposite the lateral surface LS the probe channel PC has been formed. The graduated lateral portion 376 can be configured to move into or out of the lateral portion 368 of the probe 360. The graduated lateral portion 376 can include the indicia 362 formed along a side surface thereof. The indicia 362 can include numbers indicating the length of the medial portion 374 spanning the cancellous bone to the cortical bone region CB. The same length can inform the choice of a polyaxial anchor 130 to be used in the particular probe channel PC. The indicia 362 can include any other marking that conveys to the surgeon which of a plurality of different length polyaxial anchor 130 to select (e.g., small, medium, and large).

Figure 23:
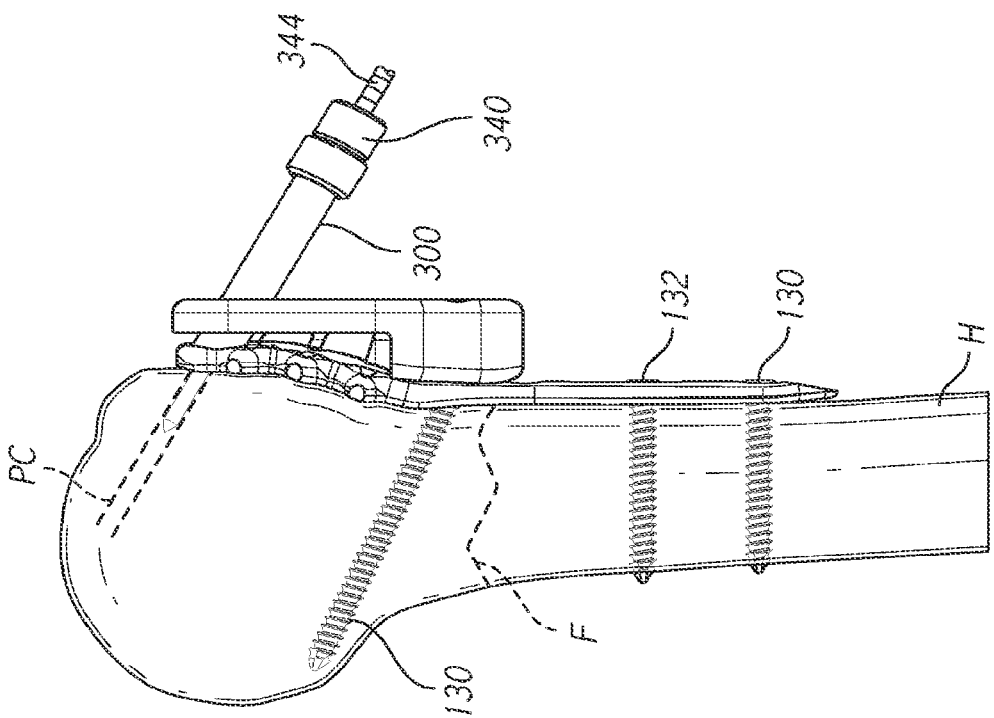
FIG. 23 shows a part of a method of connecting the fixation plate to the humerus following the part of the methods illustrated in FIG. 22 in which an anterior-superior lateral cortex access opening is formed.
Figure 22:
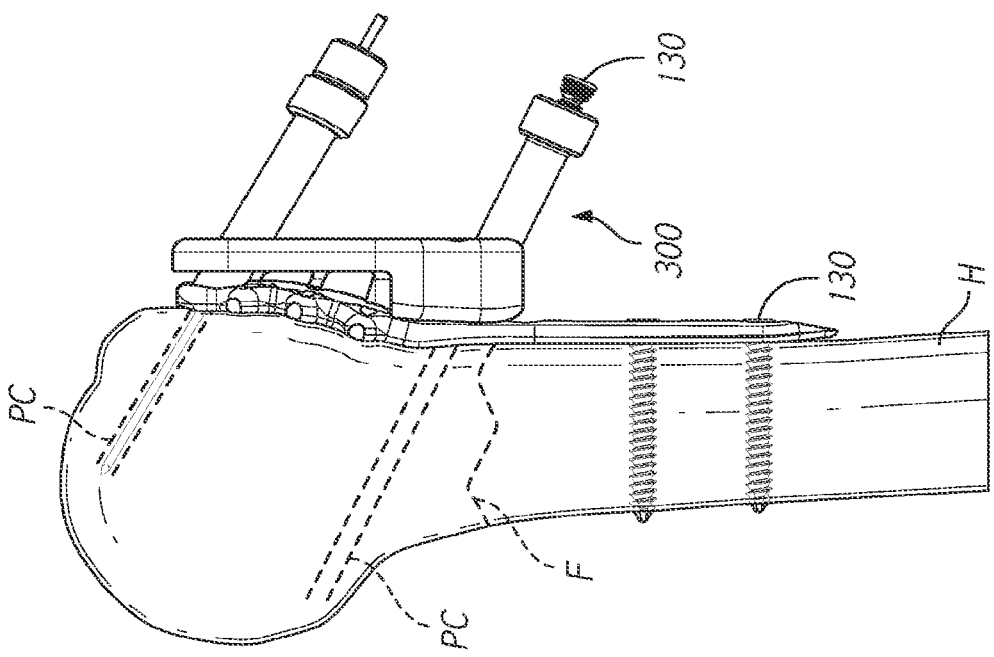
FIG. 22 shows a part of a method of connecting the fixation plate to the humerus following the part of the methods illustrated in FIGS. 18-19 in which an anchor of selected length is advanced through the lateral cortex access opening.

FIG. 22 shows that in a technique after the size of the polyaxial anchor 130 to be used is selected, the appropriately sized polyaxial anchor 130 can be inserted into the sleeve 300 and advanced into the probe channel PC through one of the inferior guide apertures 232I. After the polyaxial anchor 130 is fully inserted the medial tip of the polyaxial anchor 130 is lodged in the opposing cortical bone region CB and the lateral end is engaged with one of the distal locating apertures 120 of the fixation plate 100, as shown in FIG. 23. Using the probe 360 ensures that the medial end of the polyaxial anchor 130 when fully advanced does not breach the cortical bone on the medial side of the humerus H. e.g., is not exposed on the articular surface of the humerus H. This is important because it prevents the polyaxial anchor 130 from contacting the articular surface at or on the glenoid of the scapula as discussed above.

FIG. 23 also shows that a technique can continue with using the drill bit 344 to facilitate enlarging an opening through the lateral surface LS of the humerus H formed by a K-wire 296 to enable the probe 360 to be used to aid in selection of an appropriately sized polyaxial anchor 130 and/or to form a probe channel PC through the head 10 of the humerus H. The drill bit 344 is advanced through the superior guide apertures 232S guided by the sleeve 300 and the inner sleeve 320.

Figure 25:
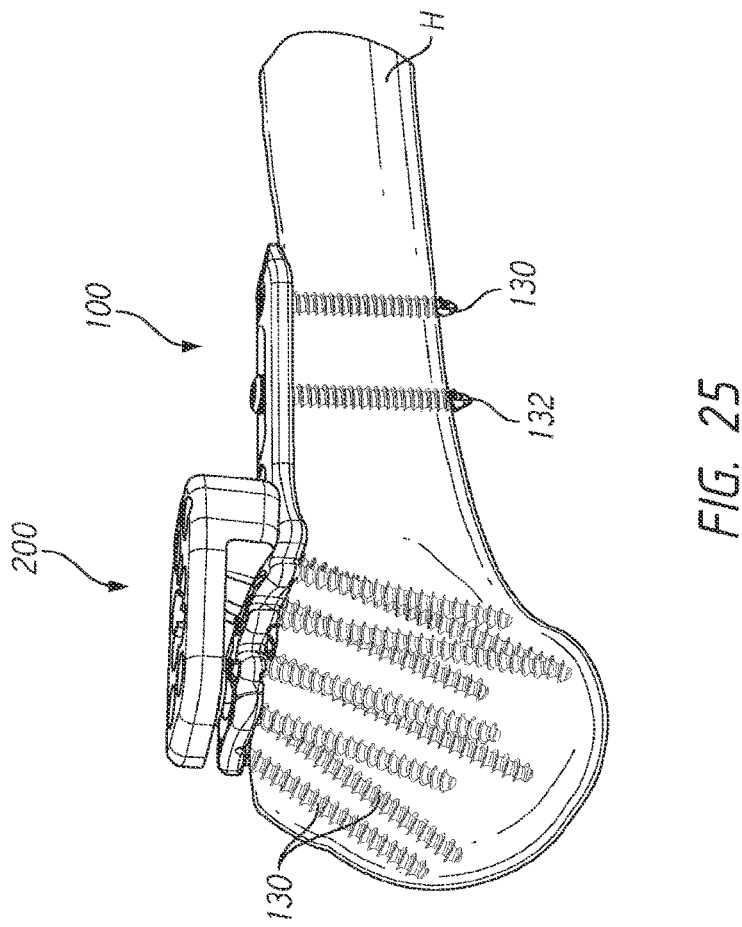
FIGS. 24 and 25 show lateral and perspective views of an assembly including the fixation plate and a plurality of screw anchors disposed through the fixation plate into the humerus with a medial side of the guide coupled with a lateral side of the fixation plate.
Figure 24:
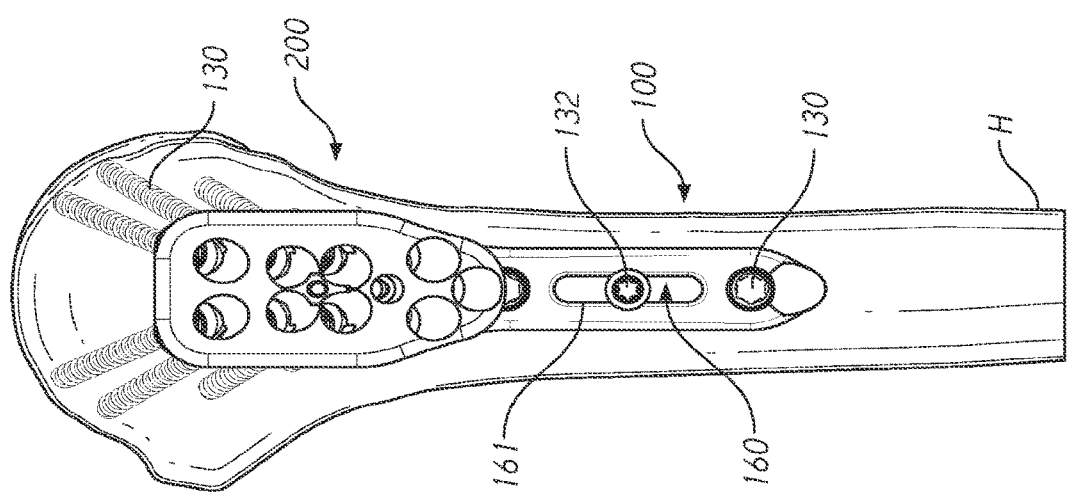

FIGS. 24 and 25 show that the processes of forming and probing the probe channels PC and selecting appropriate sized polyaxial anchors 130 and thereafter inserting the polyaxial anchor 130 into the humerus H can be continued until a sufficient number of polyaxial anchor 130 are implanted, e.g., more than half of the anchor aperture 134 and some cases all of the anchor aperture 134 have a polyaxial anchor 130 secured therein. Thereafter the anchor trajectory guide 200 can be undocked form the lateral side 108 of the fixation plate 100. In one embodiment, a screw is removed from coupling aperture 172 and the fastener aperture 237 and the locator 220 can be removed from the locating aperture 120 to permit the anchor trajectory guide 200 to be removed from the fixation plate 100.

Figure 26:
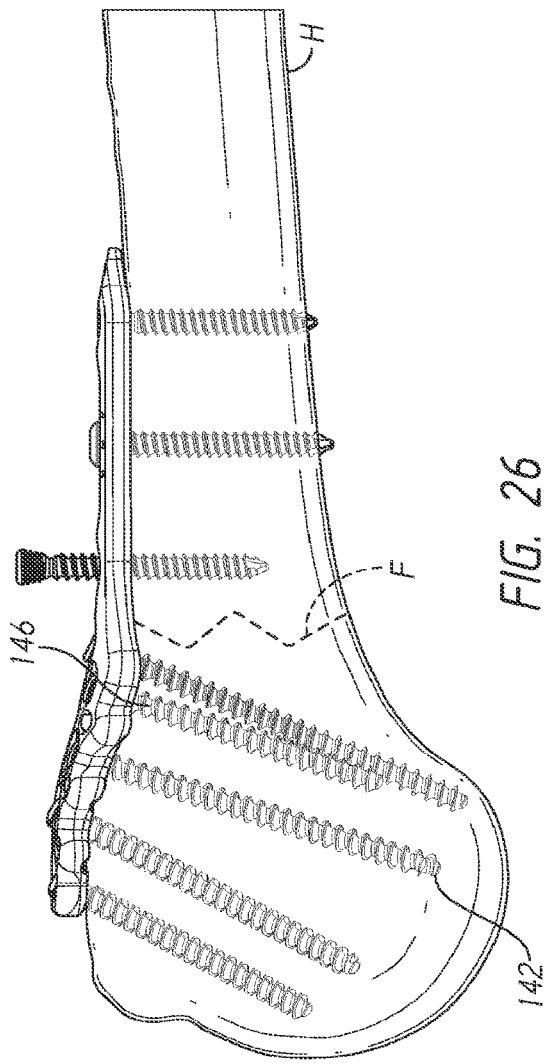
FIGS. 26 and 27 are posterior and medial side views that illustrates a part of a method of connecting the fixation plate to the humerus following the part of the method illustrated in FIGS. 24 and 25.

FIG. 26 shows that in some techniques at least one of the polyaxial anchors 130 can be implanted after the anchor trajectory guide 200 is removed. In one technique a polyaxial anchor 130 can be implanted on the distal side of the neck of the humerus H, e.g., distal of the fracture F without any guidance from the anchor trajectory guide 200.

FIG. 27 shows that in some techniques a great deal of splaying is provided among the polyaxial anchor 130. For example, some, more or all of the polyaxial anchor(s) 130 on an anterior side of the medial-lateral and proximal-distal plane PL can be oriented to diverge from the medial-lateral and proximal-distal plane PL at their medial tips. Some, more or all of the polyaxial anchor 130 on a posterior side of the medial-lateral and proximal-distal plane PL can be oriented to diverge from the medial-lateral and proximal-distal plane PL at their medial tips. Providing at least some splaying creates excellent security and force spreading to assure strong connection of the fixation plate 100 to bone portions located proximal and distal of the fracture F. Greater splaying also assures that the medial end 142 of the non-locking anchor 132 will be outside of or around the periphery of the articular surface of the head 10. This peripheral positioning of the medial end 142 provides an enhanced degree of safety for the patient.

As discussed above the anchor trajectory guide 200 can be provided in a range of sizes. For example, the anchor trajectory guide 200 can have a small size, a medium size, and a large size. The large size anchor trajectory guide 200 can provide a greater amount of splaying than illustrated in FIG. 27 such that the polyaxial anchor tips are secured in the cortical bone. In the larger size the medial ends 142 can be disposed outside of a boundary 500 that is more anterior on one of the medial-lateral and proximal-distal plane PL and more posterior on the opposite side of the medial-lateral and proximal-distal plane PL than is the illustrated by the medial ends 142 shown in FIG. 27. The smaller size anchor trajectory guide 200 can provide a lesser amount of splaying than illustrated in FIG. 27. In the smaller size, the medial ends 142 will be disposed inside a boundary 504 that is less anterior on one of the medial-lateral and proximal-distal plane PL and less posterior on the opposite side of the medial-lateral and proximal-distal plane PL than is the illustrated by the medial ends 142 shown in FIG. 27. Of course the bone will also be smaller for patient for which the boundary 504 is appropriate. As such the location of the medial ends 142 will generally stay peripheral of the articular surface of the humerus H regardless of the size of the anchor trajectory guide 200. The polyaxial anchor 130 enable the same fixation plate 100 to be used with a range of sizes, including enabling the medial end 142 to reach the position shown or either one of the boundaries 500, 504. This advantageously simplifies the number of kits and the inventory needed to provide great outcomes for a wide range, if not the entire population, of patients. As discussed above the anchor trajectory guide 200 can be patient specific to provide the maximal amount of splaying possible in the bone of the specific patient or to target maximal amount of splaying into good bone and minimize splaying into weakened bone. In that case, the amount of splaying is specific to the patient and can be different for each anchor aperture 134 and for each polyaxial anchor 130.

Figure 28:
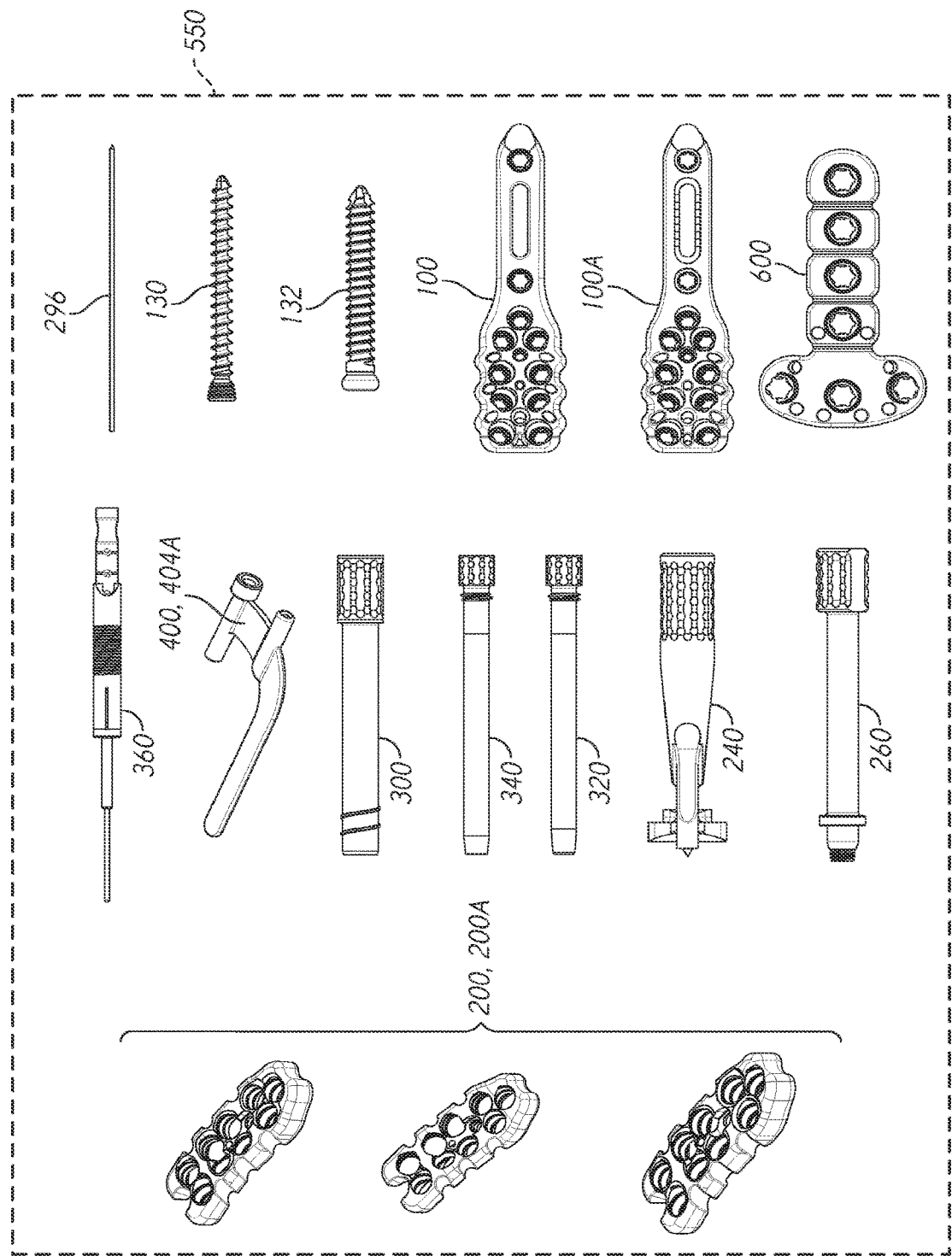
FIG. 28 illustrates a kit comprising a guide, a fixation plate and a plurality of anchors as well as instruments facilitating connection of the fixation plate to the humerus.

FIG. 28 shows an example of a kit 550 that can be provided in some embodiments. The kit 550 includes a plurality of anchor trajectory guides 200. Each of the anchor trajectory guide 200 can include a different size. For example, one of the anchor trajectory guide 200 can be suitable for an average size humerus, one of the anchor trajectory guide 200 can be suitable for larger humerus sizes, and one can be suitable for smaller humerus sizes. The periphery of the anchor trajectory guide 200 are generally not different, but the locations, positions, orientations, and/or trajectories of the guide apertures 232 through the anchor trajectory guide 200 will be different to assure the medial end 142 are splayed to an appropriate degree. The kit 550 can also include the fixation plate 100. The kit 550 also can include the humeral fixation plate 100A. The kit 550 also can include a tuberosity fracture plate 600 discussed further below. Further, the kit 550 can include a plurality of polyaxial anchor 130. The polyaxial anchor 130 will be provided in a range of sizes to facilitate the above methods which provide the distal (medial) tips of the anchors to be lodged in opposing cortical bone but not breaching the opposite (medial) side of the humerus while the proximal (lateral) ends of the polyaxial anchor 130 are engaged with the lateral side 108 of the fixation plate 100. This requires a range of sizes for the polyaxial anchor 130 disposed in the neck region and in various regions of the head 10 portion of the humerus H, as indicated by the probe 360. The kit 550 can also include one or a plurality of non-locking anchor 132 configured for engaging the slot 160 of the fixation plate 100. The kit 550 can also include a plurality of surgical tools, including K-wires 296, outer sleeves 300, inner K-wire sleeves 320, inner probe and screw sleeves 340, and probe 360. The kit 550 can comprise a kit of implantable components and a kit of surgical components.

IV. Tuberosity Plates and Methods

FIGS. 1B, 1C, and 29-30D illustrate a tuberosity fracture plate 600 and the use thereof to repair a tuberosity fracture TF in the humerus. The tuberosity fracture plate 600 includes a tuberosity end 604 and a distal portion 608. A distance between the tuberosity end 604 and the opposite end of the distal portion 608 can be between about 40 mm and about 70 mm. e.g., between 45 mm and 65 mm. The distance between the tuberosity end 604 and the opposite end of the distal portion 608 can be between 50 mm and 60 mm, e.g., about 53 mm. The tuberosity end 604 includes a first portion 612 and a second portion 616. The first portion 612 can be a portion that will overlay a first tuberosity, e.g., a greater tuberosity GT. The first portion 612 can be used to secure one side of a fractured first tuberosity OT to the rest of the humerus H. The second portion 616 can be used to secure the other side of a fractured first tuberosity CT to the rest of the humerus H.

The first portion 612 can be used to secure one side of a second tuberosity, e.g., a lesser tuberosity LT to the rest of the humerus H. The second portion 616 can be used to secure the other side of a fractured second tuberosity LT to the rest of the humerus H. A distance between a portion of the first portion 612 disposed opposite the longitudinal axis 648 and a portion of the second portion 616 disposed opposite the longitudinal axis 648 can be between about 15 mm and about 45 mm, e.g., between about 20 mm and about 40 mm. In some cases, a distance between a portion of the first portion 612 disposed opposite the longitudinal axis 648 and a portion of the second portion 616 disposed opposite the longitudinal axis 648 can be between about 25 mm and about 35 mm, e.g., about 29 mm.

The first portion 612 and the second portion 616 can both be used to secure a greater tuberosity, e.g., the first portion 612 can be used on a left humerus H to secure the greater tuberosity GT and the second portion 616 can be used on a right humerus H to secure the greater tuberosity GT of the right arm.

The tuberosity fracture plate 600 can have a plurality of screw holes. For instance, a first screw hole 624 can be provided on the tuberosity end 604. The first screw hole 624 can be disposed in the first portion 612 to hold a polyaxial screw 130 to secure a first tuberosity GT. A second screw hole 628 can be provided on the tuberosity fracture plate 600. For example the second screw hole 628 can be provided on the distal portion 608. The second screw hole 628 also can engage a polyaxial screw 130 to secure the tuberosity fracture plate 600 to the humerus H, e.g., to a portion of the humerus H not on fractured fragment, e.g., the fragment including the first tuberosity GT. The tuberosity fracture plate 600 can include additional screw holes, e.g., a screw hole 640 can be provided in the distal portion 608. A plurality of screw holes 640 can be provided in the distal portion 608. A screw hole 644 can be provided in the tuberosity end 604. A plurality of screw holes 644 can be provided in the tuberosity end 604. The screw hole or holes 644 can be disposed away from the first screw hole 624. The screw hole 644 can secure a portion of the humeral head when the first screw hole 624 is secured to the fractured and fragmented first tuberosity GT. Usually all of the screw holes 624, 644, will be engaged with a screw 130. FIG. 299 shows that screws 130 can be placed in each of the screw holes of the plate 600. FIG. 30A shows that the plate 600 can have a relief 625 formed in the screw holes 624, 644 that are off-set from the longitudinal axis 648. The relief 625 is formed to allow the screw 130 be inserted into the plate 600 along a trajectory that is perpendicular to a plane tangent to the lateral side of the plate 600 at the longitudinal axis 648. The relief 625 can enable a screw 139 to be disposed along a trajectory that is parallel to the trajectory of one or more screws 130 disposed through the screw holes that are on the longitudinal axis 648, e.g., extending perpendicular to the axis 648 through the holes 640. In other techniques the first screw hole 624 is used to secure the fragmented portion of the humerus H, e.g., the first tuberosity GT and the screw hole or holes 644 is left without any screws in it to minimize the invasiveness of the procedure in the humerus H.

The tuberosity fracture plate 600 can include a bend zone 632 disposed along the length there. The bend zone 632 can be a portion that is configured to preferentially bend. For example, when a load is applied to the ends of the tuberosity fracture plate 600 the plate bend in the bend zone 632. In one embodiment a bend zone 632 is provided between the tuberosity end 604 and the distal portion 608. In one embodiment, a plurality of bend zones 632 are provided along the length of the tuberosity fracture plate 600. A bend zone 632 can be provided between each pair of a plurality of adjacent screw holes 640. The bend zone 632 enable a plate that initially disposed along a straight longitudinal axis 648 to be shaped to match the shape of the lateral side of the humerus H. The shaped form of the tuberosity fracture plate 600 can be adjusted from straight along the longitudinal axis 648 to one or a plurality of curves along the length from the proximal to the distal end of the tuberosity fracture plate 600.

The bend zone 632 can be formed in any suitable way. For example, the tuberosity fracture plate 600 can have a portion with a first thickness 654 at one or all of the screw hole 640 and a second thickness 656 in the bend zone 632. The second thickness 656 can be less than the first thickness 654. The second thickness 656 can be less than 50% of the thickness of the tuberosity fracture plate 600 outside the bend zone 632. The thickness 656 can be between 0.5 mm and 1.5 mm, e.g., about 1 mm in various embodiments. The thickness 656 can be between 0.5 mm and 1.5 mm, e.g., about 1 mm. Without the bend zone 632 the location of the screw hole 640 would be the location most likely to localize bending. The location of the screw hole 640 would correspond to a bending location. However, because the bend zone 632 has a second thickness 656 that is less than the first thickness 654 the bending of the tuberosity fracture plate 600 is focused at the bend zone 632. The second thickness 656 can be one-half or less than the first thickness 654. The second thickness 656 can be about one-half the first thickness 654. The second thickness 656 can be about one-third the first thickness 654. The second thickness 656 can be about one-quarter the first thickness 654.

FIG. 30C shows that the tuberosity fracture plate 600 can be pre-formed with transverse curvature. The tuberosity fracture plate 600 can be curved in the tuberosity end 604 transverse to the longitudinal axis 648. The tuberosity fracture plate 600 can be curved in the distal portion 608 transverse to the longitudinal axis 648.

FIG. 30D shows that one or more of the first screw hole 624, the second screw hole 628, the screw holes 640, and the screw hole 644 can be threaded. The threaded holes 624, 628, 640, 644 can be configured to receive polyaxial screw 130. The threaded holes 624, 628, 640, 644 can thus enable the polyaxial screw 130 to be targeted to safe anatomy of the humerus H, e.g., away from the articular surface thereof.

Figure 29:
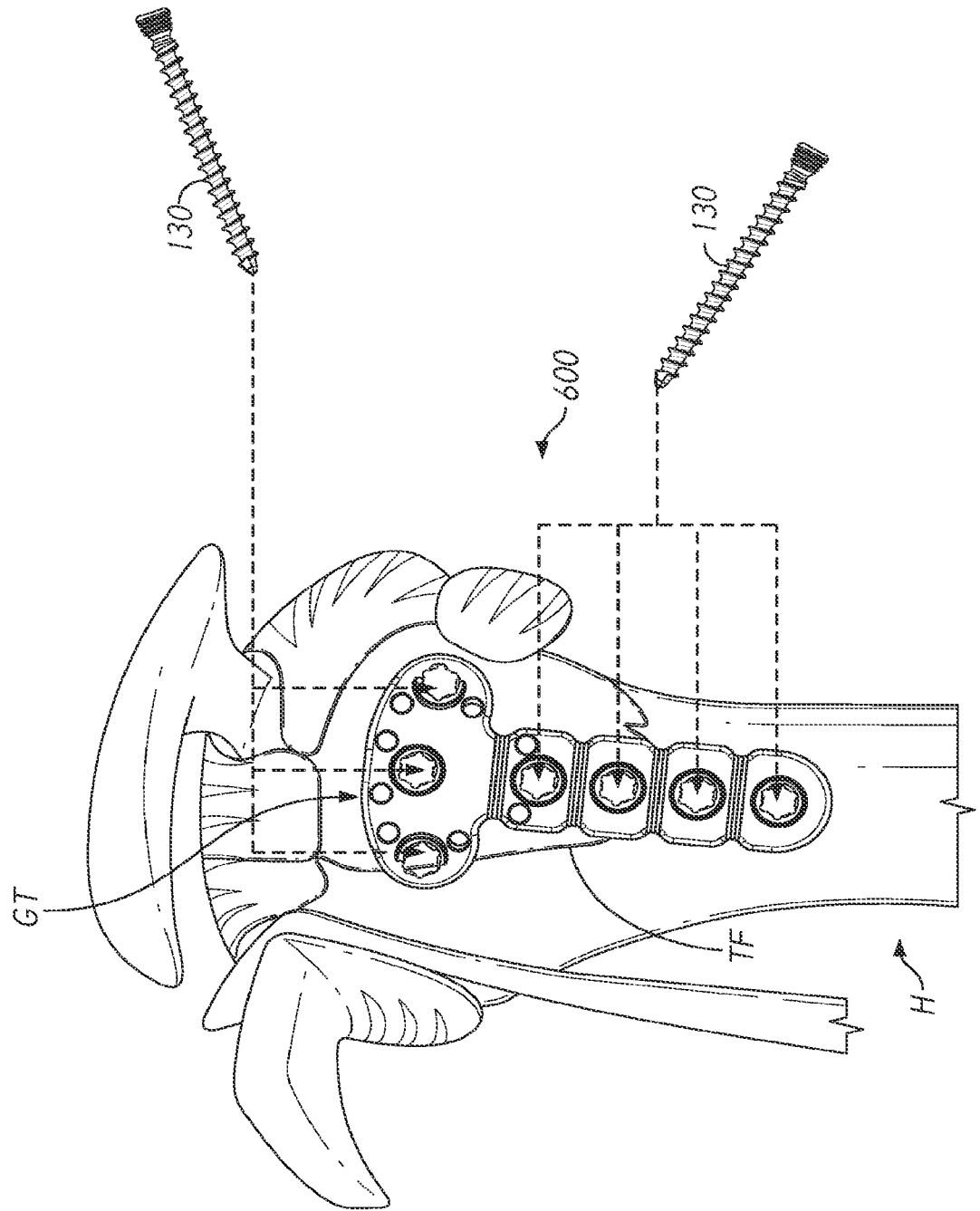
FIG. 29 is a perspective view of a tuberosity fracture plate coupled to a greater tuberosity by a plurality of screw anchors.

FIG. 29 illustrates the method of securing a fracture of a first, e.g., a greater tuberosity GT. The first tuberosity OT is brought into place on the remainder of the humerus H. The tuberosity fracture plate 600 is placed over the humerus H and the first tuberosity GT. A polyaxial screw 130 is advanced through the first screw hole 624 and into the first tuberosity GT. One or more, e.g., all of the screw hole 640 receive a polyaxial screw 130. Prior to placing some or all of the polyaxial screw 130 the tuberosity fracture plate 600 can be shaped to match the shape of the humerus H. The tuberosity fracture plate 600 can be bent along one or more of the bend zones 632 to create curvature along the longitudinal axis 648 that matches that of the particular patient's humerus H. The tuberosity fracture plate 600 can be fully secured to the one once shaped. In some methods, gross shaping is performed by the surgeon. The very act of advancing the polyaxial screw 130 into the tuberosity fracture plate 600 can cause additional bending to further match the tuberosity fracture plate 600 to the shape of the humerus H of the patient.

The tuberosity fracture plate 600 can have one or a plurality of suture apertures 652. The plurality of suture apertures 652 can receive a suture to secure one or more bone fragment to the tuberosity fracture plate 600. For example, in some cases the first tuberosity GT is too fragmented to allow the polyaxial screw 130 to secure the first tuberosity GT to the tuberosity fracture plate 600. In that case, one or more sutures can secure the fragment(s) of the first tuberosity GT to the tuberosity fracture plate 600 and/or to the rest of the humerus H.

Terminology

Although certain embodiments have been described herein, the implants and methods described herein can interchangeably use any articular component, as the context may dictate.

As used herein, the relative terms "proximal" and "distal" shall be defined from the perspective of the humerus. Thus, proximal refers to the direction of the end of the humerus adjacent to the scapula and forming part of the shoulder joint, which may be referred to herein as the superior direction, end or portion, and distal refers to the direction away from proximal, which can be the end of the humerus forming part of the elbow joint and which may be referred to herein as the inferior direction, end or portion of the humerus.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to." "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner, however, they can also include any third-party instruction of those actions, either expressly or by implication. For example, actions such as "inserting a humeral stem into a humerus" include "instructing insertion of a humeral head into a humerus."

What is claimed is:

1. A slot anchor guide, comprising:
   a medial portion and a lateral portion;
   the medial portion comprising an oval shaped medial projection wherein the medial projection is configured to mate with an oval shaped slot of a fixation plate establishing an interference fit such that the fixation plate is held on the slot anchor guide and the slot anchor guide can be used to manipulate the fixation plate;
   wherein the slot anchor guide is configured to guide an anchor through a predetermined position in the slot of the fixation plate and to mate with the fixation plate to allow the fixation plate to be configured to engage a bone surface by manipulating the lateral portion; and
   wherein the lateral portion includes an elongate cylinder that projects between a terminal lateral end of the slot anchor guide and the medial portion and a lumen therethrough the elongate cylinder that extends from the terminal lateral end through the lateral portion to an arched opening adjacent to the medial portion.

2. The slot anchor guide of claim 1, further comprising a handle coupled with the lateral portion, the handle extending transverse to the lateral portion to a free end.

3. The slot anchor guide of claim 1, wherein the medial projection further comprises one or more cleats configured to extend through a thickness of the fixation plate and mate with a bone surface to hold the slot anchor guide and the fixation plate coupled therewith in position against the bone surface.

4. The slot anchor guide of claim 3, wherein the cleats are configured as short spikes that project medially of the medial projection.

5. The slot anchor guide of claim 1, further comprising a superior-inferior projection comprising an anchor hole, the superior-inferior projection configured to align the anchor hole with an anchor aperture of the fixation plate when the medial projection is received in the slot of the fixation plate.

6. The slot anchor guide of claim 1, wherein inferior-superior extent of the medial projection is smaller than inferior-superior extent of the slot so that the medial projection can slip into the slot.

7. The slot anchor guide of claim 1, wherein the lateral portion includes an elongate cylinder that projects between a terminal lateral end of the slot anchor guide and the medial portion.

8. An assembly comprising:
   a slot anchor guide that comprises:
      a medial portion and a lateral portion;
      the medial portion comprising an oval shaped medial projection wherein the medial projection is configured to mate with an oval shaped slot of a fixation plate establishing an interference fit such that the fixation plate is held on the slot anchor guide and the slot anchor guide can be used to manipulate the fixation plate;
      wherein the slot anchor guide is configured to guide an anchor through a predetermined position in the slot of the fixation plate and to mate with the fixation plate to allow the fixation plate to be configured to engage a bone surface by manipulating the lateral portion;
   the fixation plate comprising an anchor aperture and the slot;
   a drill sleeve comprising an elongate cylinder and a lumen disposed therethrough, the drill sleeve including threads disposed on an external surface of a medial portion thereof; and
   an anchor trajectory guide that includes a guide groove located in an inferior terminal end and configured to receive a curved free end of the superior-inferior projection of the slot anchor guide so that the slot anchor guide and the anchor trajectory guide nest together when mated to the fixation plate;
   wherein the slot anchor guide can be secured to the fixation plate by engaging the threads of the drill sleeve with threads of the anchor aperture through a superior-inferior projection of the slot anchor guide.

9. The assembly of claim 8 wherein the fixation plate includes a superior anchor aperture and an inferior anchor aperture, the superior and inferior anchor apertures being located equal distances from an inferior-superior center of the slot, the slot anchor guide including a projection being positionable superiorly or inferiorly relative to the fixation plate such that an anchor hole can be aligned with the superior anchor aperture or the inferior anchor aperture.

\* \* \* \* \*